(12) United States Patent
Jewett et al.

(10) Patent No.: US 10,465,221 B2
(45) Date of Patent: Nov. 5, 2019

(54) GENOMICALLY RECODED ORGANISMS LACKING RELEASE FACTOR 1 (RF1) AND ENGINEERED TO EXPRESS A HETEROLOGOUS RNA POLYMERASE

(71) Applicant: Northwestern University, Evanston, IL (US)

(72) Inventors: Michael Christopher Jewett, Evanston, IL (US); Benjamin James Des Soye, Evanston, IL (US)

(73) Assignee: Northwestern University, Evanston, IL (US)

( * ) Notice: Subject to any disclaimer, the term of this patent is extended or adjusted under 35 U.S.C. 154(b) by 47 days.

(21) Appl. No.: 15/651,484

(22) Filed: Jul. 17, 2017

(65) Prior Publication Data

US 2018/0016614 A1 Jan. 18, 2018

Related U.S. Application Data

(60) Provisional application No. 62/362,988, filed on Jul. 15, 2016.

(51) Int. Cl.
| | |
|---|---|
| *C12P 21/02* | (2006.01) |
| *C12N 15/70* | (2006.01) |
| *C12N 9/12* | (2006.01) |
| *C07K 14/245* | (2006.01) |

(52) U.S. Cl.
CPC ............ *C12P 21/02* (2013.01); *C07K 14/245* (2013.01); *C12N 9/1247* (2013.01); *C12N 15/70* (2013.01)

(58) Field of Classification Search
None
See application file for complete search history.

(56) References Cited

U.S. PATENT DOCUMENTS

2016/0257946 A1* 9/2016 Zimmerman ............ C07K 1/02
2016/0362708 A1* 12/2016 Jewett ....................... C12P 7/16

OTHER PUBLICATIONS

Bremer, H. & Dennis, P. *Escherichia coli* and *Salmonella*: Cellular and Molecular Biology. 2 edn, vol. 1 1553-1569 (ASM Press, 1996).
Bryant, J. A., Sellars, L. E., Busby, S. J. & Lee, D. J. Chromosome position effects on gene expression in *Escherichia coli* K-12. Nucleic acids research 42, 11383-11392, doi:10.1093/nar/gku828 (2014).
Bundy, B. C. & Swartz, J. R. Site-specific incorporation of p-propargyloxyphenylalanine in a cell-free environment for direct protein-protein click conjugation. Bioconjugate chemistry 21, 255-263, doi:10.1021/bc9002844 (2010).
Carlson, E. D., Gan, R., Hodgman, C. E. & Jewett, M. C. Cell-free protein synthesis: applications come of age. Biotechnology advances 30, 1185-1194, doi:10.1016/j.biotechadv.2011.09.016 (2012).
Caschera, F. & Noireaux, V. Synthesis of 2.3 mg/ml of protein with an all *Escherichia coli* cell-free transcription-translation system. Biochimie 99, 162-168, doi:10.1016/j.biochi.2013.11.025 (2014).
Catherine, C. et al. Engineering Thermal Properties of Elastin-like Polypeptides by Incorporation of Unnatural Amino Acids in a Cell-free Protein Synthesis System. Biotechnology and Bioprocess Engineering 20, 417-422, doi:10.1007/s12257-015-0190-1 (2015).
Chappell, J., Jensen, K. & Freemont, P. S. Validation of an entirely in vitro approach for rapid prototyping of DNA regulatory elements for synthetic biology. Nucleic acids research 41, 3471-3481, doi:10.1093/nar/gkt052 (2013).
Chen, Y. J. et al. Characterization of 582 natural and synthetic terminators and quantification of their design constraints. Nature methods 10, 659-664, doi:10.1038/nmeth.2515 (2013).
Datsenko, K. A. & Wanner, B. L. One-step inactivation of chromosomal genes in *Escherichia coli* K-12 using PCR products. Proceedings of the National Academy of Sciences of the United States of America 97, 6640-6645, doi:10.1073/pnas.120163297 (2000).
Davanloo, P., Rosenberg, A. H., Dunn, J. J. & Studier, F. W. Cloning and expression of the gene for bacteriophage T7 RNA polymerase. Proceedings of the National Academy of Sciences of the United States of America 81, 2035-2039 (1984).
De Boer, H. A., Comstock, L. J. & Vasser, M. The tac promoter: a functional hybrid derived from the trp and lac promoters. Proceedings of the National Academy of Sciences of the United States of America 80, 21-25 (1983).
Des Soye, B. J., Patel, J. R., Isaacs, F. J. & Jewett, M. C. Repurposing the translation apparatus for synthetic biology. Current opinion in chemical biology 28, 83-90, doi:10.1016/j.cbpa.2015.06.008 (2015).
Dumas, A. e., Lercher, L., Spicer, C. D. & Davis, B. G. Designing logical codon reassignment—Expanding the chemistry in biology. Chemical Science 6, 50-69 (2014).
Ellinger, T. & Ehricht, R. Single-step purification of T7 RNA polymerase with a 6-histidine tag. BioTechniques 24, 718-720 (1998).
Espah Borujeni, A., Channarasappa, A. S. & Salis, H. M. Translation rate is controlled by coupled trade-offs between site accessibility, selective RNA unfolding and sliding at upstream standby sites. Nucleic acids research 42, 2646-2659, doi:10.1093/nar/gkt1139 (2014).

(Continued)

*Primary Examiner* — Nancy A Treptow
(74) *Attorney, Agent, or Firm* — Quarles & Brady LLP; M. Scott McBride

(57) ABSTRACT

Disclosed are methods, systems, components, and compositions related to genomically recoded and engineered organisms. The disclosed genomically recoded and engineered organisms may be used to prepare extracts for use in platforms and methods for preparing sequence defined biopolymers in vitro. In particular, the methods, systems, components, and compositions relate to genomically recoded and engineered organisms comprising a strain deficient in release factor 1 (RF-1) or a genetic homolog thereof, wherein the genomically recoded organisms have been engineered to express a heterologous RNA polymerase that may be utilized to express a target protein from a transcription template comprising a promoter for the heterologous RNA polymerase, such as bacteriophage T7 RNA polymerase.

20 Claims, 17 Drawing Sheets
Specification includes a Sequence Listing.

(56) References Cited

OTHER PUBLICATIONS

Fritz, B. R., Jamil, O. K. & Jewett, M. C. Implications of macromolecular crowding and reducing conditions for in vitro ribosome construction. Nucleic acids research 43, 4774-4784, doi:10.1093/nar/gkv329 (2015).

Gottesman, S. Proteases and their targets in *Escherichia coli*. Annual review of genetics 30, 465-506, doi:10.1146/annurev.genet. 30.1.465 (1996).

Grodberg, J. & Dunn, J. J. ompT encodes the *Escherichia coli* outer membrane protease that cleaves T7 RNA polymerase during purification. Journal of bacteriology 170, 1245-1253 (1988).

Heinzelman, P., Schoborg, J. A. & Jewett, M. C. pH responsive granulocyte colony-stimulating factor variants with implications for treating Alzheimer's disease and other central nervous system disorders. Protein engineering, design & selection : PEDS 28, 481-489, doi:10.1093/protein/gzv022 (2015).

Hong, S. H. et al. Cell-free protein synthesis from a release factor 1 deficient *Escherichia coli* activates efficient and multiple site-specific nonstandard amino acid incorporation. ACS synthetic biology 3, 398-409, doi:10.1021/sb400140t (2014).

Hong, S. H. et al. Improving Cell-Free Protein Synthesis through Genome Engineering of *Escherichia coli* Lacking Release Factor 1. Chembiochem : a European journal of chemical biology, doi:10.1002/cbic.201402708 (2015).

Hong, S. H., Kwon, Y. C. & Jewett, M. C. Non-standard amino acid incorporation into proteins using *Escherichia coli* cell-free protein synthesis. Frontiers in chemistry 2, 34, doi:10.3389/fchem.2014.00034 (2014).

Horton, R. M. PCR-mediated recombination and mutagenesis. SOEing together tailor-made genes. Molecular biotechnology 3, 93-99, doi:10.1007/BF02789105 (1995).

Hwang, B. Y. et al. Substrate specificity of the *Escherichia coli* outer membrane protease OmpP. Journal of bacteriology 189, 522-530, doi:10.1128/JB.01493-06 (2007).

Ikeda, R. A. & Richardson, C. C. Enzymatic properties of a proteolytically nicked RNA polymerase of bacteriophage T7. The Journal of biological chemistry 262, 3790-3799 (1987).

Ikeda, R. A. & Richardson, C. C. Interactions of a proteolytically nicked RNA polymerase of bacteriophage T7 with its promoter. The Journal of biological chemistry 262, 3800-3808 (1987).

Inouye, S. & Inouye, M. Up-promoter mutations in the lpp gene of *Escherichia coli*. Nucleic acids research 13, 3101-3110 (1985).

Jewett, M. C. & Swartz, J. R. Mimicking the *Escherichia coli* cytoplasmic environment activates long-lived and efficient cell-free protein synthesis. Biotechnology and bioengineering 86, 19-26, doi:10.1002/bit.20026 (2004).

Karim, A. S. & Jewett, M. C. A cell-free framework for rapid biosynthetic pathway prototyping and enzyme discovery. Metabolic engineering 36, 116-126, doi:10.1016/j.ymben.2016.03.002 (2016).

Kwon, Y. C. & Jewett, M. C. High-throughput preparation methods of crude extract for robust cell-free protein synthesis. Scientific reports 5, 8663, doi:10.1038/srep08663 (2015).

Lajoie, M. J. et al. Genomically recoded organisms expand biological functions. Science 342, 357-360, doi:10.1126/science.1241459 (2013).

Lederberg, J. & Lederberg, E. M. Replica plating and indirect selection of bacterial mutants. Journal of bacteriology 63, 399-406 (1952).

Li, J. et al. Cell-free protein synthesis enables high yielding synthesis of an active multicopper oxidase. Biotechnology Journal 11, 212-218, doi:10.1002/biot.201500030 (2016).

Liu, C. C. & Schultz, P. G. Adding new chemistries to the genetic code. Annual review of biochemistry 79, 413-444, doi:10.1146/annurev.biochem.052308.105824 (2010).

Martemyanov, K. A., Shirokov, V. A., Kurnasov, O. V., Gudkov, A. T. & Spirin, A. S. Cell-free production of biologically active polypeptides: application to the synthesis of antibacterial peptide cecropin. Protein expression and purification 21, 456-461, doi:10.1006/prep.2001.1400 (2001).

Mosberg, J. A., Lajoie, M. J. & Church, G. M. Lambda red recombineering in *Escherichia coli* occurs through a fully single-stranded intermediate. Genetics 186, 791-799, doi:10.1534/genetics.110.120782 (2010).

Muller, D. K., Martin, C. T. & Coleman, J. E. Processivity of proteolytically modified forms of T7 RNA polymerase. Biochemistry 27, 5763-5771 (1988).

Nehring, S., Budisa, N. & Wiltschi, B. Performance analysis of orthogonal pairs designed for an expanded eukaryotic genetic code. PloS one 7, e31992, doi:10.1371/journal.pone.0031992 (2012).

Petrov, A. S. et al. RNA-magnesium-protein interactions in large ribosomal subunit. The journal of physical chemistry. B 116, 8113-8120, doi:10.1021/jp304723w (2012).

Raucher, D. & Ryu, J. S. Cell-penetrating peptides: strategies for anticancer treatment. Trends in molecular medicine 21, 560-570, doi:10.1016/j.molmed.2015.06.005 (2015).

Renesto, P. & Raoult, D. From genes to proteins: in vitro expression of rickettsial proteins. Annals of the New York Academy of Sciences 990, 642-652 (2003).

Salis, H. M., Mirsky, E. A. & Voigt, C. A. Automated design of synthetic ribosome binding sites to control protein expression. Nature biotechnology 27, 946-950, doi:10.1038/nbt.1568 (2009).

Santoro, S. W., Wang, L., Herberich, B., King, D. S. & Schultz, P. G. An efficient system for the evolution of aminoacyl-RNA synthetase specificity. Nature biotechnology 20, 1044-1048, doi:10.1038/nbt742 (2002).

Shin, J. & Noireaux, V. An *E. coli* cell-free expression toolbox: application to synthetic gene circuits and artificial cells. ACS synthetic biology 1, 29-41, doi:10.1021/sb200016s (2012).

Shin, J. & Noireaux, V. Efficient cell-free expression with the endogenous *E. coli* RNA polymerase and sigma factor 70. Journal of biological engineering 4, 8, doi:10.1186/1754-1611-4-8 (2010).

Sousa, R. in Encyclopedia of Biological Chemistry vol. 4 (eds William J. Lennarz & M. Daniel Lane) (Elsevier, 2004).

Stefano, J. E. & Gralla, J. Lac UV5 transcription in vitro. Rate limitation subsequent to formation of an RNA polymerase-DNA complex. Biochemistry 18, 1063-1067 (1979).

Studier, F. W. & Moffatt, B. A. Use of bacteriophage T7 RNA polymerase to direct selective high-level expression of cloned genes. Journal of molecular biology 189, 113-130 (1986).

Sullivan, C. J. et al. A cell-free expression and purification process for rapid production of protein biologics. Biotechnology journal 11, 238-248, doi:10.1002/biot.201500214 (2016).

Swartz, J. R., Jewett, M. C. & Woodrow, K. A. Cell-free protein synthesis with prokaryotic combined transcription-translation. Methods in molecular biology (Clifton, N.J.) 267, 169-182, doi:10.1385/1-59259-774-2:169 (2004).

Takahashi, M. K. et al. Characterizing and prototyping genetic networks with cell-free transcription-translation reactions. Methods 86, 60-72, doi:10.1016/j.ymeth.2015.05.020 (2015).

Tunitskaya, V. L. & Kochetkov, S. N. Structural-functional analysis of bacteriophage T7 RNA polymerase. Biochemistry. Biokhimiia 67, 1124-1135 (2002).

Wang, H. H. & Church, G. M. Multiplexed genome engineering and genotyping methods applications for synthetic biology and metabolic engineering. Methods in enzymology 498, 409-426, doi:10.1016/B978-0-12-385120-8.00018-8 (2011).

Wang, H. H. et al. Programming cells by multiplex genome engineering and accelerated evolution. Nature 460, 894-898, doi:10.1038/nature08187 (2009).

Wang, L., Zhang, Z., Brock, A. & Schultz, P. G. Addition of the keto functional group to the genetic code of *Escherichia coli*. Proceedings of the National Academy of Sciences of the United States of America 100, 56-61, doi:10.1073/pnas.0234824100 (2003).

Watanabe, M. et al. Cell-free protein synthesis for structure determination by X-ray crystallography. Methods in molecular biology 607, 149-160, doi:10.1007/978-1-60327-331-2_13 (2010).

Wu, I. L. et al. Multiple site-selective insertions of noncanonical amino acids into sequence-repetitive polypeptides. Chembiochem : a European journal of chemical biology 14, 968-978, doi:10.1002/cbic.201300069 (2013).

(56) References Cited

OTHER PUBLICATIONS

Xu, Z., Chen, H., Yin, X., Xu, N. & Cen, P. High-level expression of soluble human beta-defensin-2 fused with green fluorescent protein in *Escherichia coli* cell-free system. Applied biochemistry and biotechnology 127, 53-62 (2005).

Yang, W. C. et al. Cell-free production of transducible transcription factors for nuclear reprogramming. Biotechnology and bioengineering 104, 1047-1058, doi:10.1002/bit.22517 (2009).

Young, T. S., Ahmad, I., Yin, J. A. & Schultz, P. G. An enhanced system for unnatural amino acid mutagenesis in *E. coli*. Journal of molecular biology 395, 361-374, doi:10.1016/j.jmb.2009.10.030 (2010).

Young, T. S. & Schultz, P. G. Beyond the canonical 20 amino acids: expanding the genetic lexicon. The Journal of biological chemistry 285, 11039-11044, doi:10.1074/jbc.R109.091306 (2010).

Zawada, J. F. et al. Microscale to manufacturing scale-up of cell-free cytokine production—a new approach for shortening protein production development timelines. Biotechnology and bioengineering 108, 1570-1578, doi:10.1002/bit.23103 (2011).

Zawada, J. & Swartz, J. Effects of growth rate on cell extract performance in cell-free protein synthesis. Biotechnology and bioengineering 94, 618-624, doi:10.1002/bit.20831 (2006).

\* cited by examiner

GENOMICALLY RECODED ORGANISMS LACKING RELEASE FACTOR 1 (RF1) AND ENGINEERED TO EXPRESS A HETEROLOGOUS RNA POLYMERASE

CROSS-REFERENCED TO RELATED PATENT APPLICATIONS

The present application claims the benefit of priority under 35 U.S.C. 119(e) to U.S. Provisional Patent Application No. 62/362,988, filed on Jul. 15, 2016, the content of which is incorporated herein by reference in its entirety.

BACKGROUND

The field of the invention relates to in vitro synthesis of proteins. In particular, the field of the invention relates to one-pot systems for incorporating non-standard amino acids into cell-free synthesized proteins.

Cell-free protein synthesis (CFPS) using extracts from prokaryotic source strains such as E. coli has undergone a transformational shift from an exploratory platform used in the discovery of the genetic code to a present-day, high-yielding protein production platform [1]. This shift is fueled by the open nature of this system, allowing for rapid combination, supplementation, and optimization of the physiochemical environment for increasing protein yields and batch reaction duration [2, 3]. Now, cell-free systems are seen as a complement to in vivo protein expression and can be used as both a prototyping platform due to its simplicity, easiness, and modular design for protein expression [4-6] as well as a large-scale production platform for difficult to express proteins in vivo [7]. The transition from exploratory platform to high-yielding protein production platform has come about, at least in part, by complex strain engineering to stabilize biological substrates in the cell-free reaction mixtures [8, 9]. These genetic modifications targeted the deletion of proteins known to affect the stability of DNA [10], mRNA [8, 11], protein [12], energy [13], and amino acids [14, 15] in the cell-free reaction. In addition to strain engineering efforts, activation of multiple biological pathways [16], decreases in cost [17], and improved understanding of reaction contents makes CFPS an attractive platform for the production of new kinds of high-value proteins.

One area of great interest for the application of cell-free systems is the production of modified proteins containing non-standard amino acids. Incorporating non-standard amino acids or unnatural amino acids (NSAAs) allows for the production of proteins with novel structures and functions that are difficult or impossible to create using the 20 canonical amino acids [18, 19]. Recently, cell-free protein synthesis (CFPS) systems have been employed to increase yields of proteins bearing NSAAs [20, 21], achieve direct protein-protein conjugation [22], explore drug discovery [23], and enhance enzyme activity [24, 25].

Typically, NSAA incorporation systems use amber suppression technology to insert NSAAs into proteins, a method by which an in-frame amber (TAG) stop codon is utilized as a sense codon for assigning NSAAs [26, 27]. Amber suppression technology, however, has limited efficiency for NSAA incorporation because of the presence of release factor 1 (RF1). RF1 naturally binds the amber stop codon (TAG) [28] and prematurely terminates protein translation. Methods to counteract this competitive termination of the TAG stop codon include increasing the addition of competing tRNA [21], tagging and purifying out RF1 [29], release factor engineering [30], and genomically recoding strains to remove RF1 and reassigning all occurrences to the synonymous TAA codon [31]. High-yield protein production with multiple-site incorporation of NSAAs still remains a critical challenge.

In addition, cell-free protein synthesis systems may involve coupled transcription and translation of a target protein. Such systems generally utilize a transcription template for synthesis of mRNA encoding the target protein. The transcription template typically will include a strong heterologous promoter for a heterologous RNA polymerase, such as the promoter for the bacteriophage T7 RNA polymerase. Such systems either need to be supplemented exogenously with the heterologous RNA polymerase in order to transcribe the target protein mRNA or the source strain that provides the cell extract for the cell-free protein synthesis system must be engineered to express the heterologous RNA polymerase. Unfortunately, source strains that have been engineered to express a heterologous RNA polymerase may not express the heterologous RNA polymerase at sufficient levels and/or native proteinases of the source strain may recognize and cleave the heterologous RNA polymerase at cryptic cleavage sites, rendering the heterologous RNA polymerase non-functional. In addition, an extract from a source strain that has been engineered to express a heterologous RNA polymerase otherwise may not function as well when utilized in cell-free protein synthesis as an extract from the native source strain. Therefore, optimized strains that express heterologous RNA polymerases, protein production platforms, and methods for producing modified proteins containing NSAAs in high yields are needed.

SUMMARY

Disclosed are methods, systems, components, and compositions for cell-free synthesis of proteins. The methods, systems, components, and compositions may be utilized for incorporating non-standard amino acids into cell-free synthesized proteins.

In some embodiments, the methods, systems, components, and compositions relate to genomically recoded and engineered organisms. The disclosed genomically recoded and engineered organisms may be used to prepare extracts for platforms and methods for preparing sequence defined biopolymers in vitro. In particular, the methods, systems, components, and compositions relate to genomically recoded and engineered organisms comprising a strain deficient in release factor 1 (RF-1) or a genetic homolog thereof, wherein the genomically recoded organisms have been engineered to express a heterologous RNA polymerase that may be utilized to express a target protein from a transcription template comprising a promoter for the heterologous RNA polymerase, such as bacteriophage T7 RNA polymerase.

In other embodiments, the methods, systems, components, and compositions relate to a platform for preparing a sequence defined biopolymer or a protein in vitro, the platform comprising a cellular extract from the genomically recoded and engineered organisms disclosed herein. In certain embodiments, a cellular extract prepared from the strain of the genomically recoded and engineered organism is capable of preparing a sequence defined biopolymer or a protein utilized coupled in vitro transcription/translation in greater yield and/or purity than a strain that is not deficient in release factor 1 (RF-1) and/or that does not express a heterologous RNA polymerase. The cellular extract prepared from the strain of the genomically recoded and engineered organisms generally does not need to be supplemented with an exogenous polymerase accordingly.

In some embodiments, the platform further comprises an orthogonal translation system component configured to incorporate unnatural amino acids. In certain embodiments, the orthogonal translation system component is expressed from a plasmid present in the genomically recoded organism, expressed from an integration site in the genome of the genetically recoded organism, co-expressed from both a plasmid present in the genomically recoded organism and an integration site in the genome of the genetically recoded organism, express in an in vitro transcription and translation reaction, or added exogenously. In some embodiments, the cellular extract from the genomically recoded organism is a component in a reaction mixture.

In some embodiments, the sequence defined biopolymer or protein prepared from the disclosed platforms and methods includes at least one unnatural amino acid. In further embodiments, the sequence defined biopolymer or protein includes at least 5 unnatural amino acids. In even further embodiments, the sequence defined biopolymer or protein comprises includes a plurality of unnatural amino acids. In some embodiments, the sequence defined biopolymer or protein encodes a therapeutic product, a diagnostic product, a biomaterial product, an adhesive product, a biocomposite product, or an agricultural product.

DETAILED DESCRIPTION

Figure 1:
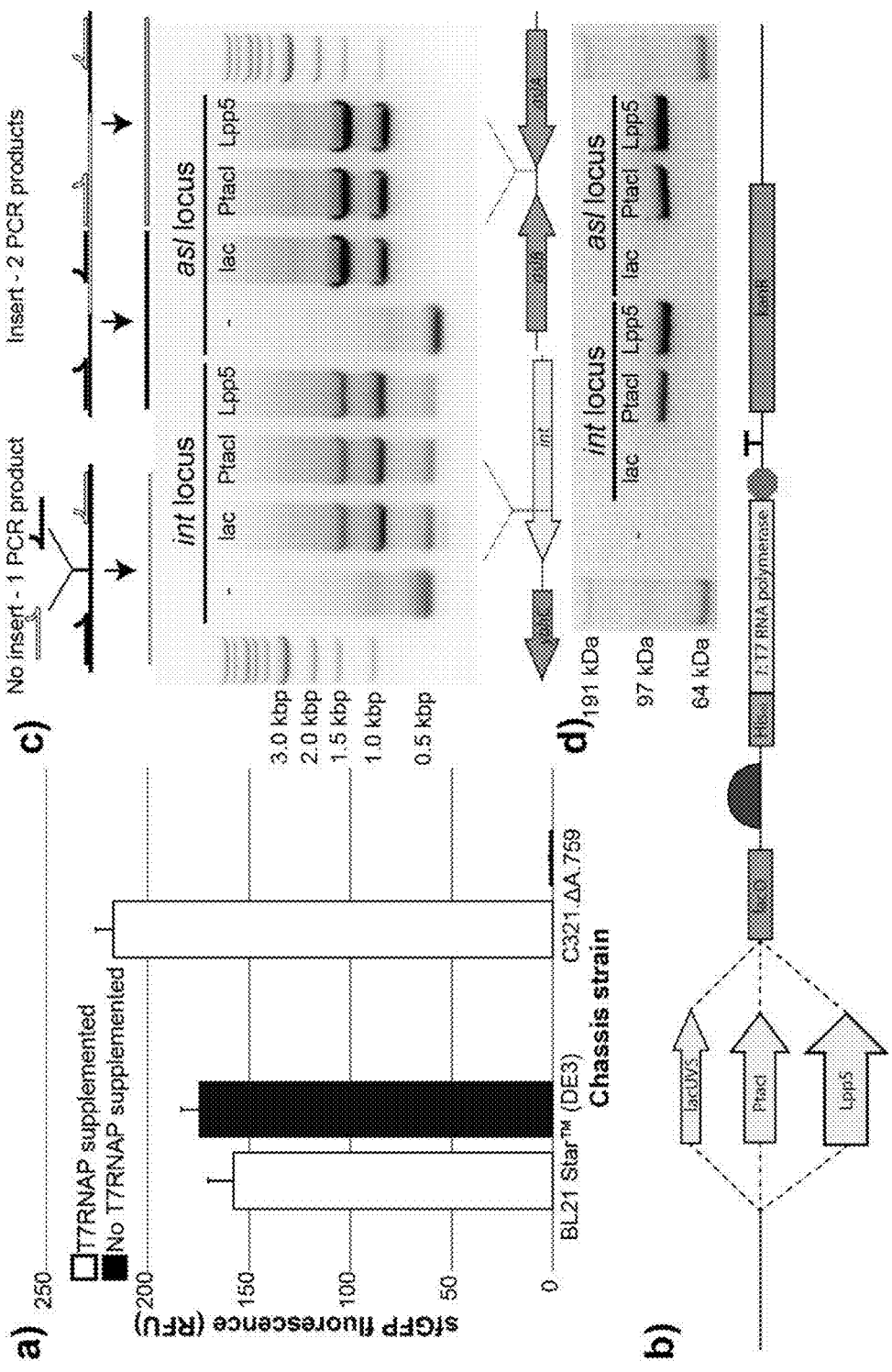
FIG. 1. Engineering a recoded E. coli strain for T7 RNA polymerase overexpression. (a) sfGFP fluorescence in vitro from cell extracts derived from induced BL21 Star™ (DE3) cells as well as C321.ΔA.759 cells, both with and without supplementation with purified T7 RNAP. (b) Schematic of the synthetic genomic insert used in this study to insert the gene encoding the T7RNAP into the genome of C321.ΔA.759. (c) Top: Diagram illustrating the PCR-based detection scheme for successful genomic integration of the synthetic T7RNAP cassette. Shown are the MASC-PCR products generated from C321.ΔA.759 and the six T7 RNAP-expressing strains generated in this study. Bottom: Depiction of the two insertion loci used. (d) α-His Western blot analysis of protein samples derived from induced populations of C321.ΔA.759 and the six T7RNAP-expressing strains generated in this study. The His-tagged T7RNAP version used has a molecular weight of ~100 kDa. The results indicate that C321.ΔA.759 is a highly productive CFPS platform ideal for NSAA incorporation, but is dependent on supplemental purified T7 RNA polymerase for transcription. The synthetic T7RNAP cassette features synthetic N-terminally His-tagged version of 1 gene under the control of a series of IPTG-inducible promoters and a synthetic RBS MASC-PCR used to detect successful integration of T7 cassette. With the insert absent, flanking primers generate a single product, and with the insert present, instead 2 products are generated. Western blot confirms that strains synthesize polymerase, and band intensity increases with increasing promoter strength.

Described herein are genomically recoded and engineered organisms, platforms for preparing sequence defined biopolymers in vitro comprising a cellular extract from genomically recoded and engineered organisms, and methods for preparing sequence defined biopolymers in vitro. The organisms and platforms described herein allow for multi-site NSAA incorporation into sequence defined biopolymers prepared in vitro at high yield and purity. The organisms have been optimized by genome engineering to express a heterologous RNA polymerase. As such, extracts prepared from the organisms need not be supplemented with the heterologous RNA polymerase to permit use of the extract in cell-free transcription/translation of a target protein that is expressed from a promoter for the heterologous RNA polymerase. The use of a cellular extract from the organisms results in a surprisingly high yield for protein production. Moreover, the use of the cellular extract resulted in surprisingly high quantities of modified protein incorporating one or more NSAAs product at high purity. Extracts produced from these genomically modified organisms show surprising promise for production of new-kinds of sequence defined biopolymers or proteins.

The presently disclosed subject matter is described herein using several definitions, as set forth below and throughout the application.

Definitions

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Unless otherwise specified or indicated by context, the terms "a", "an", and "the" mean "one or more." For example, "a component" should be interpreted to mean "one or more components."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

Ranges recited herein include the defined boundary numerical values as well as sub-ranges encompassing any non-recited numerical values within the recited range. For example, a range from about 0.01 mM to about 10.0 mM includes both 0.01 mM and 10.0 mM. Non-recited numerical values within this exemplary recited range also contemplated include, for example, 0.05 mM, 0.10 mM, 0.20 mM, 0.51 mM, 1.0 mM, 1.75 mM, 2.5 mM 5.0 mM, 6.0 mM, 7.5 mM, 8.0 mM, 9.0 mM, and 9.9 mM, among others. Exemplary sub-ranges within this exemplary range include from about 0.01 mM to about 5.0 mM; from about 0.1 mM to about 2.5 mM; and from about 2.0 mM to about 6.0 mM, among others.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target, "target sequence", "target region", and "target nucleic acid," as used herein, are synonymous and refer to a region or sequence of a nucleic acid which is to be amplified, sequenced, or detected.

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar, or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Letters 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; Wetmur, 1991, Critical Review in Biochem. and Mol. Biol. 26(3/4):227-259; and Owczarzy et al., 2008, Biochemistry, 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)$_n$ sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, bacteriophage polymerases such as, but not limited to, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, the term "sequence defined biopolymer" refers to a biopolymer having a specific primary sequence. A sequence defined biopolymer can be equivalent to a genetically-encoded defined biopolymer in cases where a gene encodes the biopolymer having a specific primary sequence.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

As used herein, "translation template" refers to an RNA product of transcription from an expression template that can be used by ribosomes to synthesize polypeptide or protein.

As used herein, coupled transcription/translation ("Tx/Tl"), refers to the de novo synthesis of both RNA and a sequence defined biopolymer from the same extract. For example, coupled transcription/translation of a given sequence defined biopolymer can arise in an extract containing an expression template and a polymerase capable of generating a translation template from the expression template. Coupled transcription/translation can occur using a cognate expression template and polymerase from the organism used to prepare the extract. Coupled transcription/translation can also occur using exogenously-supplied expression template and polymerase from an orthogonal host organism different from the organism used to prepare the extract. In the case of an extract prepared from a yeast organism, an example of an exogenously-supplied expression template includes a translational open reading frame operably coupled a bacteriophage polymerase-specific promoter and an example of the polymerase from an orthogonal host organism includes the corresponding bacteriophage polymerase.

The term "reaction mixture," as used herein, refers to a solution containing reagents necessary to carry out a given reaction. An "amplification reaction mixture", which refers to a solution containing reagents necessary to carry out an amplification reaction, typically contains oligonucleotide primers and a DNA polymerase in a suitable buffer. A "PCR reaction mixture" typically contains oligonucleotide primers, a DNA polymerase (most typically a thermostable DNA polymerase), dNTPs, and a divalent metal cation in a suitable buffer.

Cell-Free Protein Synthesis (CFPS)

The disclosed subject matter relates in part to methods, systems, components, and compositions for cell-free protein synthesis. Cell-free protein synthesis (CFPS) is known and has been described in the art. (See, e.g., U.S. Pat. Nos.

6,548,276; 7,186,525; 8,734,856; 7,235,382; 7,273,615; 7,008,651; 6,994,986 7,312,049; 7,776,535; 7,817,794; 8,298,759; 8,715,958; 9,005,920; U.S. Publication No. 2014/0349353, and U.S. Publication No. 2016/0060301, the contents of which are incorporated herein by reference in their entireties). A "CFPS reaction mixture" typically contains a crude or partially-purified yeast extract, an RNA translation template, and a suitable reaction buffer for promoting cell-free protein synthesis from the RNA translation template. In some aspects, the CFPS reaction mixture can include exogenous RNA translation template. In other aspects, the CFPS reaction mixture can include a DNA expression template encoding an open reading frame operably linked to a promoter element for a DNA-dependent RNA polymerase. In these other aspects, the CFPS reaction mixture can also include a DNA-dependent RNA polymerase to direct transcription of an RNA translation template encoding the open reading frame. In these other aspects, additional NTP's and divalent cation cofactor can be included in the CFPS reaction mixture. A reaction mixture is referred to as complete if it contains all reagents necessary to enable the reaction, and incomplete if it contains only a subset of the necessary reagents. It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

Genomically Recoded Organisms

An aspect of the present invention is a genomically recoded organism (GRO) comprising a strain deficient in release factor 1 (RF1) or a genetic homolog thereof, wherein the GRO further has been engineered to express a heterologous RNA polymerase. GRO comprising a strain deficient in RF1 or a genetic homolog thereof may be prepared by any method of strain engineering. In certain embodiments the strain deficient in RF1 is prepared in which all instances of the UAG codon have been removed, permitting the deletion of release factor 1 (RF1; terminates translation at UAG and UAA) and, hence, eliminating translational termination at UAG codons. This GRO allows for the reintroduction of UAG codons, along with orthogonal translation machinery to permit efficient and site-specific incorporation of NSAAs into proteins. That is, UAG may be transformed from a nonsense codon (terminates translation) to a sense codon (incorporates amino acid of choice), provided the appropriate translation machinery is present.

The strain may comprise a prokaryote strain. In some embodiments, the strain is an *E. coli* strain. In certain specific embodiments, the strain is *E. coli* strain C321.ΔprfA, *E. coli* strain rec13.ΔprfA, or a derivative of either *E. coli* strain C321.ΔprfA or *E. coli* strain rec13.ΔprfA. Other suitable strains are disclosed in U.S. Published Application No. 2016/0060301, the content of which is incorporated herein by reference in its entirety.

GROs Engineered to Express a Heterologous RNA Polymerase

In another aspect of the invention, the GRO comprising a strain deficient in RF1 or a genetic homolog thereof further comprises an additional engineered modification in that the GRO is engineered to express a heterologous RNA polymerase. Suitable RNA polymerases may include, but are not limited to, bacteriophage RNA polymerases.

Suitable bacteriophage RNA polymerases for the disclosed methods, systems, components and compositions may include the bacteriophage T7 RNA polymerase or variants thereof. The amino acid sequence of T7 RNA polymerase is provided herein as SEQ ID NO:1 and a DNA sequence encoding 17 RNA polymerase is provided as SEQ ID NO:2. The promoter sequence for T7 RNA polymerase is provided as SEQ ID NO:3 (which may be present on a transcription template for expressing a target protein in the cell-free protein synthesis systems disclosed herein). In some embodiments of the disclosed methods, systems, components and compositions, variants of 17 RNA polymerase may include polymerases having at least about 50%, 60%, 70%, 80%, 90%, 95%, 96%, 97%, 98%, or 99% amino acid sequence identity to SEQ ID NO:1 and/or polymerases encoded by a DNA having at least about 50%, 60%, 70%, 80%, 90%, 95%, 96%, 97%, 98%, or 99% nucleotide sequence identity to SEQ ID NO:2. In some embodiments, variants of 17 RNA polymerase are resistant to cleavage by a host protease of a recombinantly engineered source strain in which the variant T7 RNA polymerase is expressed. For example, a variant of T7 RNA polymerase may include a deletion of 1 or more amino acids, an insertion of one or more amino acids, and/or one or more amino acid substitutions that make the variant resistant to cleavage by a host protease of a recombinantly engineered source strain in which the variant 17 RNA polymerase is expressed. Amino acid substitutions may include replacing one or more basic amino acids (e.g., K172, R173, K179, and/or K180) with an amino acid that is not basic (e.g., a replacement amino acid for K172, R173, K179, and/or K180 selected from A, G, I, and L).

Suitable bacteriophage RNA polymerases for the disclosed methods, systems, components and compositions may include the bacteriophage T3 RNA polymerase or variants thereof. The amino acid sequence of T3 RNA polymerase is provided herein as SEQ ID NO:4 and a DNA sequence encoding T3 RNA polymerase is provided as SEQ ID NO:5. The promoter sequence for T3 RNA polymerase is provided as SEQ ID NO:6 (which may be present on a transcription template for expressing a target protein in the cell-free protein synthesis systems disclosed herein). In some embodiments of the disclosed methods, systems, components and compositions, variants of T3 RNA polymerase may include polymerases having at least about 50%, 60%, 70%, 80%, 90%, 95%, 96%, 97%, 98%, or 99% amino acid sequence identity to SEQ ID NO:4 and/or polymerases encoded by a DNA having at least about 50%, 60%, 70%, 80%, 90%, 95%, 96%, 97%, 98%, or 99% nucleotide sequence identity to SEQ ID NO:5. In some embodiments, variants of T3 RNA polymerase are resistant to cleavage by a host protease of a recombinantly engineered source strain in which the variant T3 RNA polymerase is expressed. For example, a variant of T3 RNA polymerase may include a deletion of 1 or more amino acids, an insertion of one or more amino acids, and/or one or more amino acid substitutions that make the variant resistant to cleavage by a host protease of a recombinantly engineered source strain in which the variant T3 RNA polymerase is expressed. Amino acid substitutions may include replacing one or more basic amino acids (e.g., K173, R174, K180, and/or K181) with an amino acid that is not basic (e.g., a replacement amino acid for K173, R174, K180, and/or K181 selected from A, G, I, and L).

Suitable bacteriophage RNA polymerases for the disclosed methods, systems, components and compositions may include the bacteriophage SP6 RNA polymerase or variants thereof. The amino acid sequence of SP6 RNA polymerase is provided herein as SEQ ID NO:7 and a DNA sequence encoding SP6 RNA polymerase is provided as SEQ ID NO:8. The promoter sequence for SP6 RNA polymerase is provided as SEQ ID NO:9 (which may be present on a transcription template for expressing a target protein in the cell-free protein synthesis systems disclosed herein). In some embodiments of the disclosed methods, systems, components and compositions, variants of SP6 RNA polymerase may include polymerases having at least about 50%, 60%, 70%, 80%, 90%, 95%, 96%, 97%, 98%, or 99% amino acid sequence identity to SEQ ID NO:7 and/or polymerases encoded by a DNA having at least about 50%, 60%, 70%, 80%, 90%, 95%, 96%, 97%, 98%, or 99% nucleotide sequence identity to SEQ ID NO:8. In some embodiments, variants of SP6 RNA polymerase are resistant to cleavage by a host protease of a recombinantly engineered source strain in which the variant SP6 RNA polymerase is expressed. For example, a variant of SP6 RNA polymerase may include a deletion of 1 or more amino acids, an insertion of one or more amino acids, and/or one or more amino acid substitutions that make the variant resistant to cleavage by a host protease of a recombinantly engineered source strain in which the variant SP6 RNA polymerase is expressed. Amino acid substitutions may include replacing one or more of basic amino acids with an amino acid that is not basic (e.g., a replacement amino acid for a basic amino acid selected from A, G, I, and L).

The GRO may be modified to express the heterologous RNA polymerase by methods known in the art including recombination methods known in the art and as disclosed herein. In some embodiments, the GRO is modified to express the heterologous RNA polymerase by recombining a cassette that expresses the heterologous RNA polymerase into the genome of the GRO, the cassette including the coding sequence for the heterologous RNA polymerase (e.g., any of SEQ ID NOs:2, 5, 8 or a variant thereof) operably linked to a suitable promoter for expressing the RNA polymerase. Suitable promoters may include inducible promoters or constitutive promoters. Preferably, the promoter is characterized as a "strong" promoter as described herein.

Additional GRO Modifications Including Knock-Out Mutations

Optionally, the GRO comprising a strain deficient in RF1 or a genetic homolog thereof and engineered to express a heterologous RNA polymerase further comprises at least one additional genetic knock-out mutation. The at least one additional genetic knock-out mutation is preferably a knock-out mutation that downregulates or eliminates a negative protein effector for CFPS. In certain embodiments, the at least one additional genetic knock-out mutation improves DNA stability, RNA stability, protein stability, amino acid stability, energy supply, or any combination thereof. In certain embodiments, the at least one additional genetic knock-out mutation comprises 1, 2, 3, 4, or more than 4 genetic knock-out mutations. In embodiments where the strain comprises 2 or more genetic knock-out mutations, at least 2 of the genetic knock-out mutations may both improve the same attribute, improved DNA stability, improved RNA stability, improved protein stability, improved amino acid stability, improved energy supply, or may both improve different attributes.

To improve DNA or RNA stability, the at least one additional genetic knock-out mutation may target the functional inactivation of nucleases. In vivo, nucleases play important roles in regulating DNA and mRNA turnover. However, their presence in crude cell extracts is expected to be deleterious, leading to template instability and reaction termination. A nonexhaustive list of potential negative effectors follow: RNase A (encoded by rna) degrades RNA by catalyzing the cleavage of phosodiester bonds, and identification of strains (e.g., MRE600, A19) lacking rna was important for early studies in in vitro translation. RNase II (encoded by rnb) is responsible for mRNA decay by 3' to 5' exonuclease activity, and cell extracts lacking RNase II exhibit a 70% increase in CFPS efficiency. RNase E (encoded by rne) is part of a cold shock degradosome that induces mRNA decay in cold shock, which the cells experience during harvest prior to extract generation. MazF (encoded by mazF) is a toxin that degrades mRNA by sequence-specific (ACA) endoribonuclease activity, which could affect transcript stability. CsdA (encoded by csdA) is part of a cold shock degradosome along with RNase E and induces mRNA decay in cold shock, which the cells experience during harvest prior to extract generation. DNA-specific endonuclease I (encoded by endA) breaks double-stranded DNA, and its deletion has previously shown to be important for extending the duration of CFPS reactions. These and other nucleases may be functionally inactivated by the at least on additional genetic knock-out mutation.

To improve protein stability, the at least one additional genetic knock-out mutation may target the functional inactivation of proteases. In vivo, these proteases play important roles in regulating protein turnover. However, their presence in CFPS reactions is expected to be deleterious, leading to protein instability issues. A nonexhaustive list of potential negative effectors follow: Glutathione reductase (encoded by gor) reduces oxidized glutathione to maintain a reducing environment in the cytoplasm of a cell, making synthesis of disulfide-bonded proteins problematic. Lon (encoded by lon) is an ATP-dependent protease that demonstrated improved protein production in cell-free systems in BL21 strains upon transcriptional down regulation. Outer membrane protease VII (encoded by ompT) demonstrates specificity for paired basic residues and has been shown to stabilize proteins during CFPS upon removal. These and other proteases may be functionally inactivated by the at least on additional genetic knock-out mutation.

The at least one additional genetic knock-out mutation may target proteins known to negatively affect amino acid or energy supply. In vivo, these proteins play important roles in metabolism and substrate turnover. However, their presence in crude cell extracts is expected to be deleterious, leading to decreased amino acid and energy supply to support translation. A nonexhaustive list of potential negative effectors follow: Glutamate dehydrogenase (encoded by gdhA) catalyzes the deamination of glutamate, which may affect glutamate's stability. Glutamate-cysteine-ligase (encoded by gshA) catalyzes the first step of glutathione synthesis and may decrease the stability of cysteine. Serine deaminase I (encoded by sdaA) and serine deaminase II (encoded by sdaB) are two of the three enzymes involved in serine degradation. Arginine decarboxylase (encoded by speA) consumes arginine in the biosynthetic production of putrescine. Tryptophanase (encoded by tnaA) consumes tryptophan in the production of indole. Lastly, glycerol kinase (encoded by glpK) consumes ATP to phosphorylate glycerol, which could help deplete the energy supply required for cell-free reactions. These and other proteins may be functionally inactivated by the at least on additional genetic knock-out mutation.

Strains having at least one additional genetic knock-out mutation, may be prepared by any method of engineering a strain to functionally inactivate the negative effector to lessen or eliminate the negative effector from a lysate prepared from the strain. In certain embodiments, the genetic knock-out mutations may be prepared by inserting either a nonsense mutation and/or a frameshift mutation into the genome of the strain as well as deleting a vital portion of a gene coding sequence. In certain embodiments, the genetic knock-out mutations may be prepared by removing regulatory sequences (i.e. promoter, ribosome binding site) or otherwise changing these sequences in the genome as to render them non-functional. In certain embodiments, negative effectors can be functionally knocked out in lysates by introducing a unique affinity tag and subsequently using the tag to selectively remove the effector protein from the lysates. In certain embodiments a strain having at least one additional genetic knock-out mutation may be prepared by multiplex automated genome engineering (MAGE), λ-Red recombinase-mediated recombination (Datsenko-Wanner), zinc-finger nucleases (ZFNs), transcription activator-like effector nucleases (TALENs), clustered regularly interspaced short palindromic repeats (CRISPR)-associated protein-9 nuclease (Cas9), and any other commonly used recombineering and genome engineering tools.

Additional GRO Modifications Including Upregulated Gene Products

Optionally, the GRO comprising a strain deficient in RF1 or a genetic homolog thereof further and engineered to express a heterologous RNA polymerase further comprises at least one additional upregulated gene product. In certain embodiments the GRO comprising a strain deficient in RF1 or a genetic homolog thereof further comprises at least one additional upregulated gene product and at least one additional genetic knock-out mutation. The at least one additional upregulated gene product is preferably an upregulated gene product that is a positive effector for CFPS. In certain embodiments, the at least one additional upregulated gene product improves energy supply, chaperone levels, translations function, ribosome recycling, or any combination thereof. In certain embodiments, the at least on additional upregulated gene product comprises 1, 2, 3, 4, or more than 4 upregulated gene products. In embodiments where the strain comprises 2 or more upregulated gene products, at least 2 of the upregulated gene products may both improve the same attribute, improved energy supply, improved chaperone levels, improved translation function, or improved ribosome recycling, or may both improve different attributes.

To improve energy supply, the at least one additional upregulated gene product may target the upregulation of kinases. In vivo, these proteins play important roles in metabolism and the transfer of phosphate groups. The upregulated presence in crude cell extracts is expected to improve energy supply to support translation. A nonexhaustive list of potential positive effectors follow: Acetate kinase (encoded by ackA) increases the overall metabolic flux of metabolites toward substrate-level ATP generation. Nucleoside-diphosphate kinase (encoded by ndk) facilitate the synthesis of NTPs from their corresponding NDPs. Pyruvate kinase monomer (encoded by pykF) helps drive ATP generation. These and other kinases may be the at least one additional upregulated gene product.

To improve energy supply, the at least one additional upregulated gene product may target the upregulate of deaminases. In vivo, these proteins may play important roles in metabolism and preparing metabolites. A nonexhaustive list of potential positive effectors follow: Cytidine deaminase (encoded by cdd) initiates the deamination of cytidine which may lead to the synthesis of UTP. These and other deaminases may be the at least one additional upregulated gene product To improve chaperone levels, the at least one upregulated gene product may target the upregulation of isomerases, foldases and/or holdases. In vivo, these proteins may play important roles in the assisting proteins to adopt functionally active conformations. The upregulated presence in crude cell extracts is expected to improve chaperone levels to support protein production into soluble and/or active confirmations. A nonexhaustive list of potential positive effectors follow: Disulfide bond isomerase (encoded by dsbC) shuffles disulfide bonds into correct positions. Chaperone protein DnaK (encoded by dnaK) aids the folding of nascent polypeptide chains and the rescue of misfolded proteins. Chaperone protein DnaJ (encoded by danJ) stimulates the ATPase activity of DnaK. Protein GrpE (encoded by grpE) stimulates the ATPas activity of DnaK. Trigger Factor (encoded by tig) aids the folding of nascent polypeptides. The 10 kDa chaperonin subunit (encoded by groS) forms part of the GroEL-GroES chaperonin complex that aids in protein folding. The 60 kDa chaperonin subunit (encoded by groL) forms part of the GroEL-GroES chaperonin complex that aids in protein folding. These and other isomerases, foldases, and/or holdases may be the at least one additional upregulated gene product.

To improve translation function, the at least one upregulated gene product may target the upregulation of initiation factors and/or elongation factors. In vivo, these proteins play important roles in the translation function. The upregulated presence in crude cell extracts is expected to improve translation function. A nonexhaustive list of potential positive effectors follow: Translation initiation factor IF-1 (encoded by infA) interacts with the 30S ribosomal subunit to initiate translations. Translation initiation faction IF-2 (encoded by infB) has a role in the proper placement of the charged initiator fMet-tRNA via a GTP-dependent mechanism. Elongations factor G (encoded by fusA) facilitates translocation of the ribosome by one codon along a mRNA. Elongation factor P (encoded by efp) stimulates the synthesis of peptide bonds. Elongation factor 4 (encoded by lepA) can alter the rate of translation, leading to increases in the rate of translation under certain stress conditions. Elongation factor TU 2 (encoded by tufB) helps shuttle charge tRNAs to ribosomes. These and other initiation factors and/or elongation factors may be the at least one additional upregulated gene product.

To improve translation function, the at least one upregulated gene product may target the upregulation of recycling factors. In vivo, these proteins play important roles in the ribosome recycling. The upregulated presence in crude cell extracts is expected to improve ribosome recycling. A nonexhaustive list of potential positive effectors follow: Heat shock protein 15 (encoded by hslR) is involved with the recycling of free 50S ribosomal subunits. Ribosome-recycling factor (encoded by frr) promotes rapid recycling of ribosomal subunits after the release of the polypeptide chain. These and other recycling factors may be the at least one additional upregulated gene product.

Strains having at least one additional genetic knock-out mutation, may be prepared by any method of engineering a strain to functionally increase a positive effector to increase the presence of the positive effector in the lysate prepared from the strain. In certain embodiments, the upregulated gene product is expressed from a plasmid present in the GRO and/or expressed from an integration site in GRO genome. Additionally, gene upregulation may be enhanced by engineering the promoter and/or ribosome binding site in front of your gene of interest located either on a plasmid or on the genome. A stronger promoter/ribosome binding site would lead to an increase in transcriptional activity. Techniques commonly employed to integrate a plasmid overexpressing a positive effector into a strain includes transformation. Techniques commonly employed to integrate a gene cassette containing a positive effector into the genome for overexpression includes X-Red recombinase-mediated recombination (Datsenko-Wanner).

Platforms for Preparing Sequence Defined Biopolymers

An aspect of the invention is a platform for preparing a sequence defined biopolymer of protein in vitro. The platform for preparing a sequence defined polymer or protein in vitro comprises a cellular extract from the GRO organism as described above. Because CFPS exploits an ensemble of catalytic proteins prepared from the crude lysate of cells, the cell extract (whose composition is sensitive to growth media, lysis method, and processing conditions) is the most critical component of extract-based CFPS reactions. A variety of methods exist for preparing an extract competent for cell-free protein synthesis, including U.S. patent application Ser. No. 14/213,390 to Michael C. Jewett et al., entitled METHODS FOR CELL-FREE PROTEIN SYNTHESIS, filed Mar. 14, 2014, and now published as U.S. Patent Application Publication No. 2014/0295492 on Oct. 2, 2014, and U.S. patent application Ser. No. 14/840,249 to Michael C. Jewett et al., entitled METHODS FOR IMPROVED IN VITRO PROTEIN SYNTHESIS WITH PROTEINS CONTAINING NON STANDARD AMINO ACIDS, filed Aug. 31, 2015, and now published as U.S. Patent Application Publication No. 2016/0060301, on Mar. 3, 2016, the contents of which are incorporated by reference.

The platform may comprise an expression template, a translation template, or both an expression template and a translation template. The expression template serves as a substrate for transcribing at least one RNA that can be translated into a sequence defined biopolymer (e.g., a polypeptide or protein). The translation template is an RNA product that can be used by ribosomes to synthesize the sequence defined biopolymer. In certain embodiments the platform comprises both the expression template and the translation template. In certain specific embodiments, the platform may be a coupled transcription/translation ("Tx/Tl") system where synthesis of translation template and a sequence defined biopolymer from the same cellular extract.

The platform may comprise one or more polymerases capable of generating a translation template from an expression template. The polymerase may be supplied exogenously or may be supplied from the organism used to prepare the extract. In certain specific embodiments, the polymerase is expressed from a plasmid present in the organism used to prepare the extract and/or an integration site in the genome of the organism used to prepare the extract.

The platform may comprise an orthogonal translation system. An orthogonal translation system may comprise one or more orthogonal components that are designed to operate parallel to and/or independent of the organism's orthogonal translation machinery. In certain embodiments, the orthogonal translation system and/or orthogonal components are configured to incorporation of unnatural amino acids. An orthogonal component may be an orthogonal protein or an orthogonal RNA. In certain embodiments, an orthogonal protein may be an orthogonal synthetase. In certain embodiments, the orthogonal RNA may be an orthogonal tRNA or an orthogonal rRNA. An example of an orthogonal rRNA component has been described in Application No. PCT/US2015/033221 to Michael C. Jewett et al., entitled TETHERED RIBOSOMES AND METHODS OF MAKING AND USING THEREOF, filed 29 May 2015, and now published as WO2015184283, and U.S. patent application Ser. No. 15/363,828, to Michael C. Jewett et al., entitled RIBOSOMES WITH TETHERED SUBUNITS, filed on Nov. 29, 2016, and now published as U.S. Patent Application Publication No. 2017/0073381, on Mar. 16, 2017, the contents of which are incorporated by reference. In certain embodiments, one or more orthogonal components may be prepare in vivo or in vitro by the expression of an oligonucleotide template. The one or more orthogonal components may be expressed from a plasmid present in the genomically recoded organism, expressed from an integration site in the genome of the genetically recoded organism, co-expressed from both a plasmid present in the genomically recoded organism and an integration site in the genome of the genetically recoded organism, express in the in vitro transcription and translation reaction, or added exogenously as a factor (e.g., a orthogonal tRNA or an orthogonal synthetase added to the platform or a reaction mixture).

Altering the physicochemical environment of the CFPS reaction to better mimic the cytoplasm can improve protein synthesis activity. The following parameters can be considered alone or in combination with one or more other components to improve robust CFPS reaction platforms based upon crude cellular extracts (for examples, S12, S30 and S60 extracts).

The temperature may be any temperature suitable for CFPS. Temperature may be in the general range from about 10° C. to about 40° C., including intermediate specific ranges within this general range, include from about 15° C. to about 35° C., form about 15° C. to about 30° C., form about 15° C. to about 25° C. In certain aspects, the reaction temperature can be about 15° C., about 16° C., about 17° C., about 18° C., about 19° C., about 20° C., about 21° C., about 22° C., about 23° C., about 24° C., about 25° C.

The CFPS reaction can include any organic anion suitable for CFPS. In certain aspects, the organic anions can be glutamate, acetate, among others. In certain aspects, the concentration for the organic anions is independently in the general range from about 0 mM to about 200 mM, including intermediate specific values within this general range, such as about 0 mM, about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM and about 200 mM, among others.

The CFPS reaction can also include any halide anion suitable for CFPS. In certain aspects the halide anion can be chloride, bromide, iodide, among others. A preferred halide anion is chloride. Generally, the concentration of halide anions, if present in the reaction, is within the general range from about 0 mM to about 200 mM, including intermediate specific values within this general range, such as those disclosed for organic anions generally herein.

The CFPS reaction may also include any organic cation suitable for CFPS. In certain aspects, the organic cation can be a polyamine, such as spermidine or putrescine, among others. Preferably polyamines are present in the CFPS reaction. In certain aspects, the concentration of organic cations in the reaction can be in the general about 0 mM to about 3 mM, about 0.5 mM to about 2.5 mM, about 1 mM to about 2 mM. In certain aspects, more than one organic cation can be present.

The CFPS reaction can include any inorganic cation suitable for CFPS. For example, suitable inorganic cations can include monovalent cations, such as sodium, potassium, lithium, among others; and divalent cations, such as magnesium, calcium, manganese, among others. In certain aspects, the inorganic cation is magnesium. In such aspects, the magnesium concentration can be within the general range from about 1 mM to about 50 mM, including intermediate specific values within this general range, such as about 1 mM, about 2 mM, about 3 mM, about 5 mM, about 6 mM, about 7 mM, about 8 mM, about 9 mM, about 10 mM, among others. In preferred aspects, the concentration of inorganic cations can be within the specific range from about 4 mM to about 9 mM and more preferably, within the range from about 5 mM to about 7 mM.

The CFPS reaction includes NTPs. In certain aspects, the reaction use ATP, GTP, CTP, and UTP. In certain aspects, the concentration of individual NTPs is within the range from about 0.1 mM to about 2 mM.

The CFPS reaction can also include any alcohol suitable for CFPS. In certain aspects, the alcohol may be a polyol, and more specifically glycerol. In certain aspects the alcohol is between the general range from about 0% (v/v) to about 25% (v/v), including specific intermediate values of about 5% (v/v), about 10% (v/v) and about 15% (v/v), and about 20% (v/v), among others.

Methods for Preparing Proteins and Sequence Defined Biopolymers

An aspect of the invention is a method for cell-free protein synthesis of a sequence defined biopolymer or protein in vitro. The method comprises contacting a RNA template encoding a sequence defined biopolymer with a reaction mixture comprising a cellular extract from a GRO as described above. Methods for cell-free protein synthesis of a sequence defined biopolymers have been described [1, 18, 26].

In certain embodiments, a sequence-defined biopolymer or protein comprises a product prepared by the method or the platform that includes an amino acids. In certain embodiments the amino acid may be a natural amino acid. As used herein a natural amino acid is a proteinogenic amino acid encoded directly by a codon of the universal genetic code. In certain embodiments the amino acid may be an unnatural amino acid. As used here an unnatural amino acid is a nonproteinogenic amino acid. An unnatural amino acids may also be referred to as a non-standard amino acid (NSAA) or non-canonical amino acid. In certain embodiments, a sequence defined biopolymer or protein may comprise a plurality of unnatural amino acids. In certain specific embodiments, a sequence defined biopolymer or protein may comprise a plurality of the same unnatural amino acid. The sequence defined biopolymer or protein may comprise at least 5, at least 10, at least 15, at least 20, at least 25, at least 30, at least 35, or at least 40 or the same or different unnatural amino acids.

Examples of unnatural, non-canonical, and/or non-standard amino acids include, but are not limited, to a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenyl-alanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, 24ufa24hor, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an a-hydroxy containing acid; an amino thio acid; an α,α disubstituted amino acid; a β-amino acid; a γ-amino acid, a cyclic amino acid other than proline or histidine, and an aromatic amino acid other than phenylalanine, tyrosine or tryptophan.

The methods described herein allow for preparation of sequence defined biopolymers or proteins with high fidelity to a RNA template. In other words, the methods described herein allow for the correct incorporation of unnatural, non-canonical, and/or non-standard amino acids as encoded by an RNA template. In certain embodiments, the sequence defined biopolymer encoded by a RNA template comprises at least 5, at least 10, at least 15, at least 20, at least 25, at least 30, at least 35, or at least 40 unnatural, non-canonical, and/or non-standard amino acids and a product prepared from the method includes at least 80%, at least 85%, at least 90%, at least 95%, or 100% of the encoded unnatural, non-canonical, and/or non-standard amino acids.

The methods described herein also allow for the preparation of a plurality of products prepared by the method. In certain embodiments, at least 80%, at least 85%, at least 90%, at least 95%, or at least 98% of a plurality of products prepared by the method are full length. In certain embodiments, the sequence defined biopolymer encoded by a RNA template comprises at least 5, at least 10, at least 15, at least 20, at least 25, at least 30, at least 35, or at least 40 unnatural, non-canonical, and/or non-standard amino acids and at least 80%, at least 85%, at least 90%, at least 95%, or at least 98% of a plurality of products prepared by the method include 100% of the encoded unnatural, non-canonical, and/or non-standard amino acids.

In certain embodiments, the sequence defined biopolymer or the protein encodes a therapeutic product, a diagnostic product, a biomaterial product, an adhesive product, a biocomposite product, or an agricultural product.

Miscellaneous

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Examples

The following Examples are illustrative and are not intended to limit the scope of the claimed subject matter.

Title: A Highly Productive One-Pot System for the Incorporation of Non-Standard Amino Acids into Cell-Free Synthesized Proteins Abstract The incorporation of non-standard amino acids (NSAAs) into proteins via amber (TAG codon) suppression provides access to novel protein properties, structures, and functions. Such efforts have historically been opposed by endogenous release factor 1 (RF1). Addressing this limitation, a genomically-recoded strain of Escherichia coli lacking RF1 was recently developed and engineered to improve its productivity in cell-free protein synthesis (CFPS) reactions. While this strain demonstrates high productivity and superior NSAA incorporation in vitro, it is limited by its dependence on the addition of purified 17 DNA-directed RNA polymerase (T7RNAP) to catalyze transcription. Here, we describe further development of this system to create a high-yielding, one-pot CFPS platform particularly suited for the synthesis of proteins bearing NSAAs. We optimized the system design by leveraging λ-Red mediated homologous recombination to genomically integrate six variants of a synthetic cassette encoding the T7RNAP. The resulting strains were assessed in CFPS for the ability to perform protein synthesis using only the polymerase synthesized inside the cells rather than supplemental T7RNAP. Lysates derived from the top strain identified in the initial round of development were, in the absence of purified T7RNAP, capable of synthesizing ~85% as much superfolder green fluorescent protein (sfGFP) as polymerase-supplemented reactions. To further develop the strain, we applied multiplex automated genome engineering (MAGE) to install mutations into the T7RNAP gene to render the polymerase resistant to proteolysis during cell lysis. Extracts derived from our final strain demonstrate superior productivity in vitro, synthesizing ~2.2 g/L sfGFP with and ~1.6 g/L sfGFP without supplementation with purified polymerase. The extracts also demonstrate high incorporation efficiency of the NSAA p-acetylphenylalanine (pAcF), yielding 50 mg/L of elastin-like polymer containing up to 40 pAcFs. Our work has implications for CFPS strain development via genome editing, expanding the chemistry of biological systems, and cell-free synthetic biology.

Introduction

A burst of technological development in recent years has transformed cell-free protein synthesis (CFPS) from a niche tool into a competitive production platform[1]. This rapid advancement has been spurred by the desire to take advantage of the beneficial features unique to CFPS systems, which include easy system access and manipulation, the elimination of competition with cellular prerogatives, and a dilute reaction environment that can facilitate folding of complex eukaryotic protein products[2,3]. Batch CFPS reactions now persist for up to twenty hrs with yields exceeding 1.5 g/L[3], and improvements in scalability culminated recently with the successful completion of a 100 L reaction[4]. These impressive advances can be largely attributed to extensive efforts to engineer CFPS systems via chassis organism development, usually by the targeted genetic deletion of genes whose products are known to destabilize key biological substrates (e.g. DNA, mRNA, amino acids, protein, and energy) in cell-free reaction[5,6]. As a result of these transformative efforts, CFPS platforms can now be used to complement protein overexpression in vivo, with particular utility in rapid prototyping[7-9], synthesis of cytotoxic products[10-13], and the production of proteins that are difficult to solubly express in vivo[4,14-16].

While native bacterial RNA polymerases and associated sigma factors can be used to catalyze transcription in CFPS reactions[17,18], the viral T7 DNA-directed RNA polymerase (T7RNAP) is often preferred due to its extremely high productivity, orthogonality, and strong sequence preference[17,19]. Most strains of E. coli do not express T7RNAP, and CFPS reactions performed with these strains require that polymerase be directly supplemented in a purified form—a requirement that demands laborious T7RNAP overexpression and purification or purchase[2,5]. Conversely, extracts derived from T7RNAP-expressing strains (most notably BL21 (DE3)[19] and its derivatives) are innately enriched in polymerase activity and generally do not require (or even benefit from) supplementation[20]. These "one-pot" CFPS systems, containing all of the biological components necessary to support transcription and translation, are highly attractive due to their convenient, "plug-and-play" nature.

One appealing application of cell-free biology is the production of proteins containing non-standard amino acids (NSAAs)[5,21,22]. To date, more than 150 different NSAAs have been incorporated into peptides[23], enabling the synthesis of proteins featuring novel structures and functions that would otherwise be difficult or even impossible to obtain using only the twenty canonical amino acids. The gold standard for site-specific NSAA incorporation is amber suppression, whereby the amber stop codon (TAG) is hijacked and recoded as a sense codon designating a NSAA of interest[24]. This process is mediated by orthogonal translation systems (OTSs), which generally consist of the NSAA, an orthogonal suppressor tRNA (o-tRNA) that has been modified to associate with TAG in the ribosomal A-site, and a NSAA-specific aminoacyl-tRNA synthetase (NSAARS) that has been evolved to covalently load the NSAA onto the o-tRNA[21,25]. The cytotoxicity of many OTSs[26], membrane impermeability of some NSAAs[27], and the ability to overcome the relatively poor incorporation efficiencies of OTSs via direct supplementation with OTS components[5,21,22] makes CFPS an attractive method for the synthesis of peptides featuring NSAAs.

Efforts to apply amber suppression to the incorporation of NSAAs have long been opposed by the activities of release factor 1 (RF1), which is responsible for terminating translation in response to the ribosome encountering a TAG codon[28]. In attempting amber suppression, functional RF1 often outcompetes NSAA-bearing o-tRNAs at TAG codons leading to the production of errant truncated products[22,29]. Addressing this significant limitation of the technology, a genomically-recoded strain of Escherichia coli (E. coli) was recently generated in which all native instances of the amber codon were changed to the synonymous ochre codon (TAA) followed by elimination of RF1 from the genome (C321.ΔA)[30]. In a follow-up effort, C321.ΔA was further engineered to augment its productivity in vitro. Extracts derived from the resulting strain (C321.ΔA.759) comprise a highly-active CFPS platform specifically designed for NSAA incorporation, and in the presence of purified supplemental T7RNAP achieves yields higher than lysates derived from state-of-the-art protein expression strain BL21 Star™ (DE3). In the synthesis of proteins bearing NSAAs, C321.ΔA.759 significantly outperforms BL21 Star™ (DE3) by virtue of its RF1 deficiency. However, C321.ΔA.759 does not overexpress T7RNAP, adding another step to reaction assembly and increasing the cost of the system by requiring the addition of purified polymerase to catalyze robust transcription.

In this study, we describe the development of a high-yielding one-pot CFPS platform for NSAA incorporation derived from a genomically-recoded RF1-deficient strain of E. coli that has been optimized for productivity in CFPS (C321.ΔA.759). Since C321.ΔA.759 does not express T7RNAP, we applied λ-Red mediated homologous recombination[31,32] (λHR) to genomically integrate a series of synthetic constructs featuring the T7RNAP-encoding 1 gene[19] and then assessed the ability of extracts derived from the resulting transformants to catalyze CFPS in the absence of exogenous polymerase supplementation. Two different genomic loci were targeted for integration, with 1 placed under the regulation of three promoters of different strengths. A high-performing strain, C321.ΔA.759.T7 was capable of synthesizing ~1.4 g/L of superfolder green fluorescent protein (sfGFP) without purified T7RNAP supplementation. We next exploited MAGE[33] to install mutations in the 1 gene of C321.ΔA.759.T7 to make it resistant to proteolytic cleavage during lysate preparation. The resulting strain C321.ΔA.759.T7.D yielded ~1.6 g/L sfGFP without T7RNAP supplementation and ~2.2 g/L with. Using an optimized system, we were able to synthesize proteins (elastin-like polypeptide, ELP) bearing up to 40 NSAAs with yields up to ~30 mg/L in the absence of supplemental T7RNAP. As opposed to BL21 (DE3) and its derivative strains, one-pot CFPS systems derived from C321.ΔA.759.T7 are exceptionally productive and superior for applications involving NSAAs.

Results and Discussion

CFPS Activity of C321.ΔA.759 and BL21 Star™ (DE3) with and without Supplemental T7RNAP.

We first set out to establish the extent to which C321.ΔA.759 lysates could perform T7-based transcription. To test this, we prepared batches of crude S30 lysates from C321.ΔA.759 as well as BL21 Star™ (DE3) which had T7RNAP expression induced with 1 mM isopropyl β-D-1-thiogalactopyranoside (IPTG). Batch CFPS reactions were performed using these lysates, directed to synthesize sfGFP both with and without direct supplementation of 16 μg/mL of purified T7RNAP (FIG. 1A). As expected, the yield from C321.ΔA.759 lysates with T7RNAP added was ~30% higher than either BL21 Star™ (DE3) condition. There was no observable benefit to supplementing additional T7RNAP into reactions utilizing polymerase-enriched BL21 Star™ (DE3) lysates. Unsurprisingly, essentially no sfGFP was synthesized by the C321.ΔA.759 lysates when no T7RNAP was supplemented. Thus, we hypothesized that introducing the 1 gene into C321.ΔA.759 would imbue the strain with the ability to synthesize T7RNAP and eliminate its dependence on supplemental polymerase in vitro.

T7RNAP Insert Design and Integration.

A large body of work has explored various ways of enabling bacteria to produce T7RNAP. Plasmid-based approaches are simple and effective, but expression levels are high enough to impair plasmid maintenance or otherwise place a significant metabolic burden on host cells manifesting itself in the form of drastically increased doubling time[19]. As increases in doubling time are often indicative of reduced ribosome abundance, this phenomenon is extremely undesirable for CFPS chassis strains[34,35]. Another common scheme for 1 gene introduction is via lysogenization with synthetic DE3 bacteriophage (as in BL21 (DE3) and its derivatives)[19], but as phage insertion occurs site-specifically at a fixed genomic locus and the viral 1 gene is under the control of a fixed set of cis-regulatory sequences, this approach suffers from a lack of tunability and control. An attractive alternative method for genomic integration is λ-Red mediated homologous recombination (λHR), which site-specifically integrates linear DNA constructs into target genomes using flanking sequence homology to direct insertion at the desired site[31,32]. As C321.ΔA.759 natively expresses the requisite λ-Red recombination machinery[30], we elected to proceed via λHR.

A challenge in protein expression is tuning the expression level—enough protein must be synthesized to adequately perform the desired function, but aggressive overexpression can place too high of a metabolic strain on the host organism and/or lead to production of inhibitory levels of the protein. Lacking a priori knowledge as to how to achieve an ideal level of T7RNAP production in C321.ΔA.759, we decided to test a variety of different expression levels. We designed a series of synthetic constructs that placed the 1 gene under the regulation of IPTG-inducible promoters of varying transcriptional strengths, with lacUV5[36], PtacI[37], and Lpp5[38] representing relatively low, medium, and high strength respectively (FIG. 1B). Promoter-specific synthetic ribosome binding sites (RBSs) designed for maximal translation were employed for the regulation of translation initiation—in this way, any differences in T7RNAP expression between strains could be predominantly attributed to differences in transcription[39,40]. In the interest of easy visualization via western blotting, we added a 6-His tag to the N-terminus of the polymerase (a modification that has previously been shown to have no effect on polymerase activity[41]). Each construct also included the kanamycin kinase (kanR) gene from pKD4[31] (which confers resistance to the antibiotic kanamycin) for selection of successful integrants. Finally, to explore influences of genome position on expression, each construct was designed with 50 bp of flanking sequence homology at each end to facilitate integration at one of two genomic loci: the asl locus, selected because it was previously identified as a highly-expressing locus in the E. coli genome[42], and the int locus, selected because it is analogous to the DE3 lysogenization site in BL21 (DE3)[19].

A total of six T7RNAP-expressing constructs were assembled (int.lacUV5, int.PtacI, int.Lpp5, asl.lacUV5, asl.PtacI, asl.Lpp5) and transformed individually into C321.ΔA.759 for site-specific genomic integration. Potential integrants were identified by the ability to survive in the presence of kanamycin and verified via screening by multiplex allele-specific colony PCR (FIG. 1C). Sanger sequencing of all insert loci confirmed that each construct was integrated at the correct locus, fully intact and free of any unwanted mutations. Finally, western blotting with antibodies against the polymerase's N-terminal 6-His tag verified that each insert was indeed promoting expression of T7RNAP (FIG. 1D). Polymerase expression as determine by blot band intensity tracked as expected with promoter strength.

Characterization of T7RNAP-Expressing Strains in CFPS.

Figure 2:
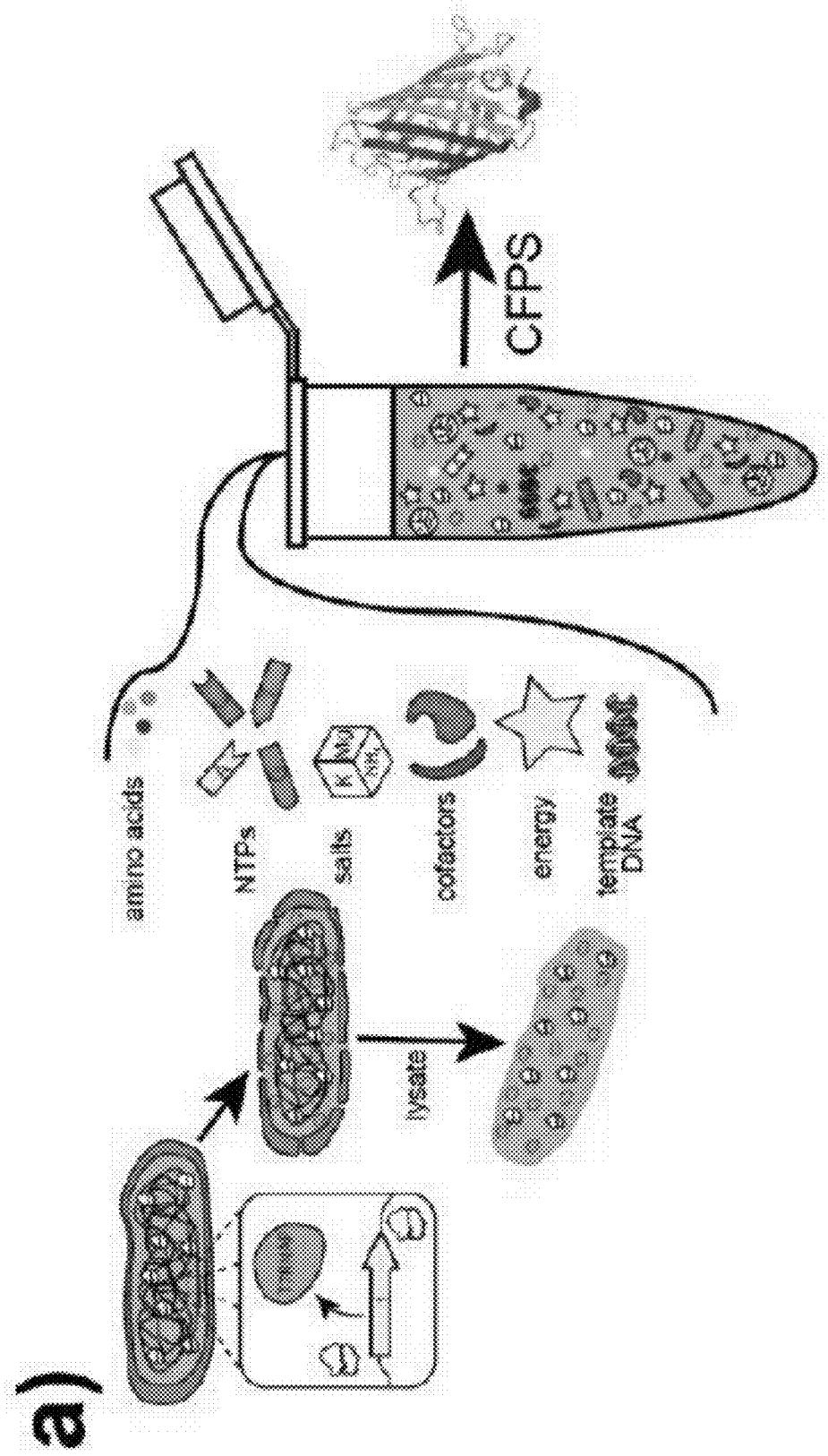
FIG. 2. Characterization of C321.ΔA.759 T7 RNAP-expressing variants. (a) Simplified schematic of the production and utilization of crude lysates from E. coli cells to catalyze cell-free protein synthesis (CFPS). Reactions are supplemented with enzymatic cofactors, energy, and other substrates required for protein synthesis as well as plasmid DNA template directing the system towards the production of a product of interest. (b) Characterization of the six C321.ΔA.759 T7 RNAP-expressing variants generated in this study. Extracts derived from C321.ΔA.759 and its T7 RNAP-expressing derivatives were directed to synthesize sfGFP in CFPS both with and without supplementation with purified T7 RNAP, and fluorescence was measured after incubation for 20 hours at 30 C. Three independent CFPS reactions were performed for each condition, and one standard deviation is shown. (c) α-His western blot characterization of C321.ΔA.759.T7. The results indicate that the insert strains behave as expected, with fluorescence increasing with increasing promoter strength and the stronger asl locus generating more fluorescence for each promoter. Insert strains putatively synthesizing the most polymerase (asl.Lpp5) perform best absent supplemental T7RNAP and were selected as the "winner" at this stage of analysis. T7RNAP synthesized by C321.ΔA.759.T7 is cleaved to yield a ~21 kDa N-terminal fragment during lysate preparation.
Figure 2:
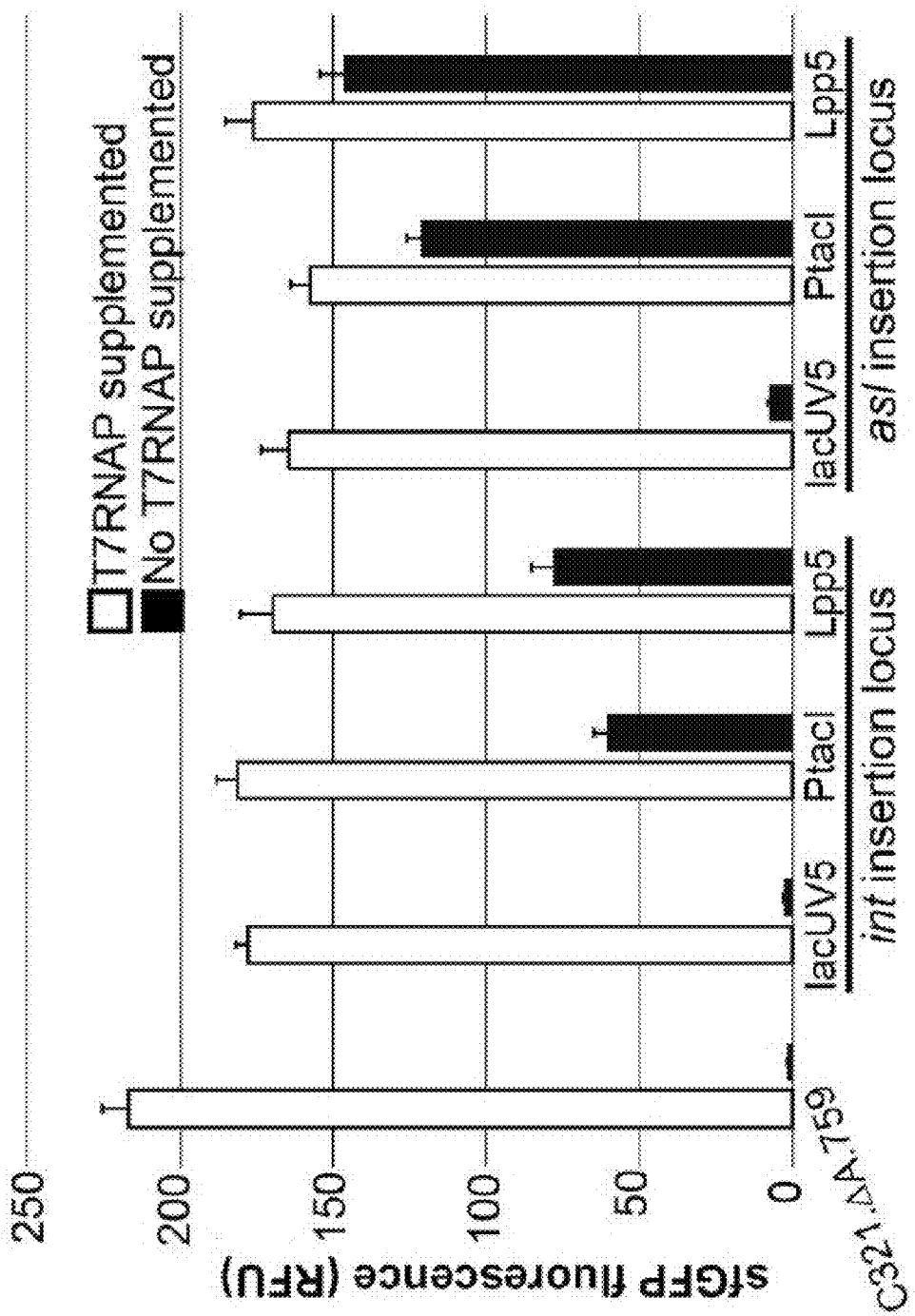
Figure 2:
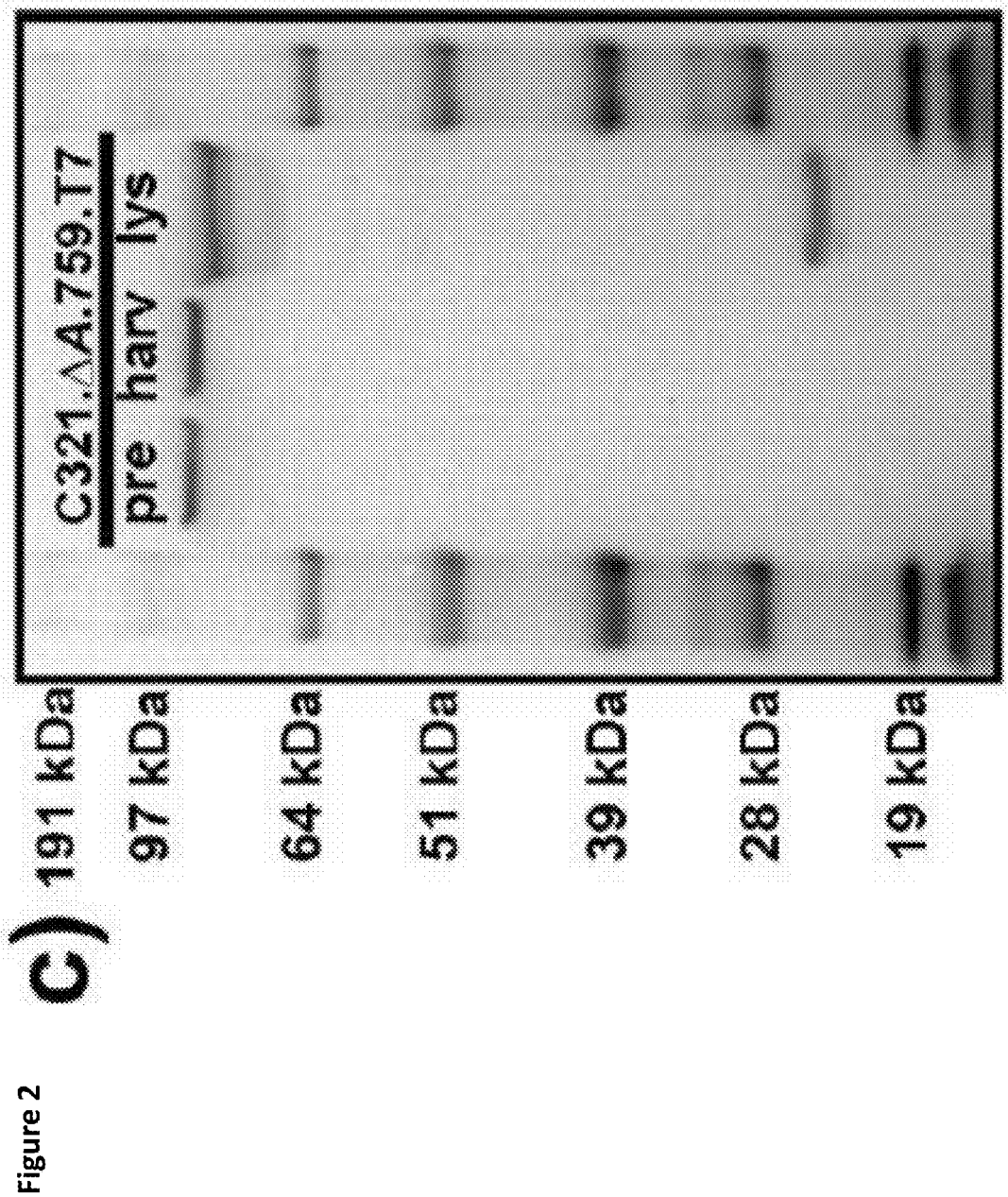

To assess the ability of these strains to independently catalyze transcription in CFPS, we prepared crude S30 lysates for all six strains for use in cell-free reactions (FIG. 2A). To promote robust T7RNAP overexpression, all strains were induced with 1 mM IPTG during exponential cell growth. Batch CFPS reactions using each lysate were directed to synthesize sfGFP over 20 h at 30° C. both with and without addition of 16 μg/mL of purified T7RNAP to the reactions (FIG. 2B). With polymerase supplemented, lysates from all six strains performed within 15% of one another. The strains featuring PtacI- and Lpp5-driven T7RNAP expression demonstrated the ability to perform transcription using only the polymerase expressed by the chassis strain. Not surprisingly, the amount of sfGFP fluorescence appears to be related to the amount of T7RNAP produced in the cells (FIG. 2B). At both insertion loci, the amount of fluorescence increases with increasing promoter strength, and for each promoter more fluorescence was observed from the strains featuring inserts at the highly-expressing asl locus. The strain capable of generating the most sfGFP fluorescence without T7RNAP supplementation, C321.ΔA.759.asl.Lpp5, achieved ~85% as much sfGFP production without supplementation as with. This strain, hereafter referred to as C321.ΔA.759.T7, was selected for further characterization and development.

Figure 8:
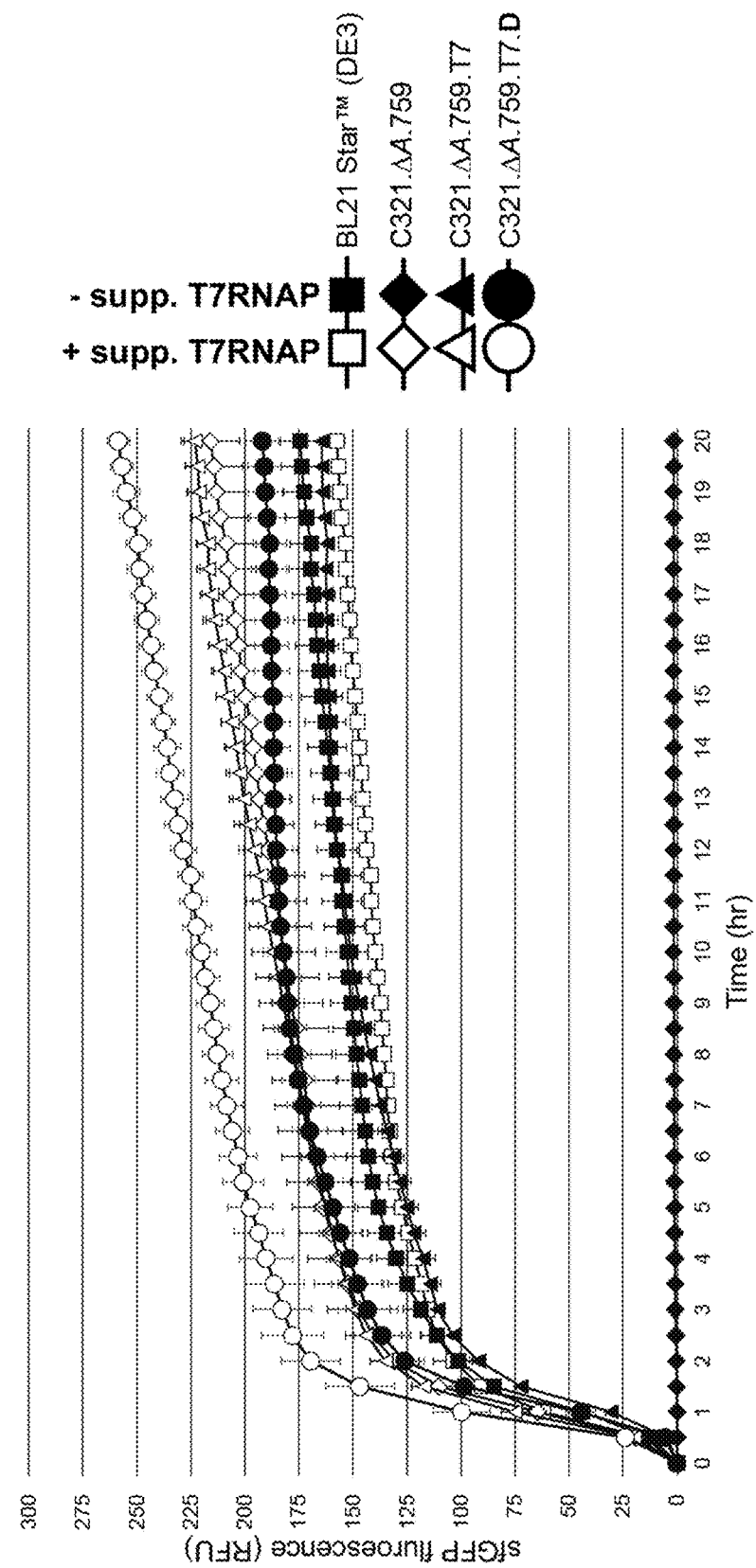
FIG. 8. Characterization of protein synthesis kinetics using lysates from the strain C321.ΔA.759.T7.D. Comparison between BL21 Star™ (DE3), C321.ΔA.759, C321.ΔA.759.T7, and C321.ΔA.759.T7.D. Extracts derived from the listed strains were directed to synthesize sfGFP with and without supplementation with purified T7RNAP. sfGFP fluorescence was measured at various timepoints over the course of a 20 hr incubation at 30° C. Three independent CFPS reactions were performed for each condition, and one standard deviation is shown. The results indicate that most protein synthesis occurs during the first 4-6 hours of the CFPS reaction, consistent with previously published results. The performance of strain C321.ΔA.759.T7.D without supplemental polymerase is better than both BL21 Star™ (DE3) conditions and comparable to other C321-derived strains with supplemental polymerase.
Figure 9:
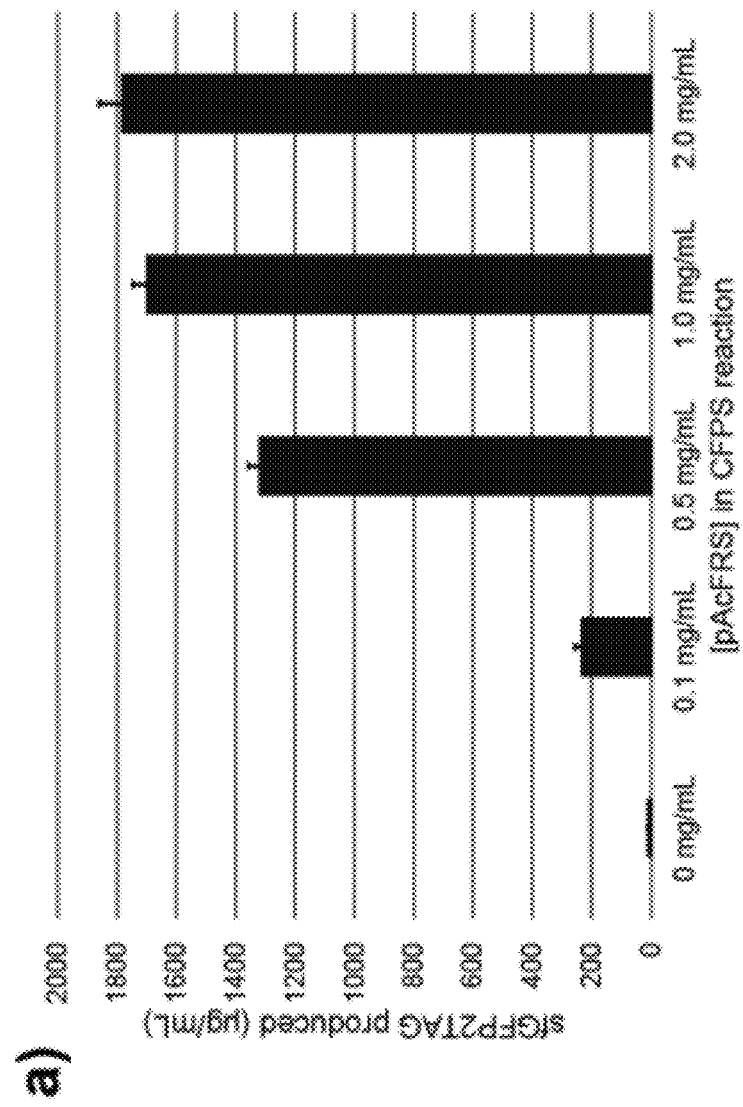
FIG. 9. Optimization of OTS component supplementation for performing amber suppression using C321.ΔA.759.T7.D lysates. These lysates were directed to synthesize sfGFP2TAG in CFPS with T7RNAP supplemented. Concentrations of pAcF OTS components (pAcFRS, (a); pAcF, (b); o-tz-tRNA LET, (c)) were titrated to identify the optimal concentration of each component. 3 independent reactions were performed per condition, and one standard deviation is shown. The results indicate that significant increases in the amount of OTS components yielded almost negligible increases in amber suppression. Standard concentrations (1.0 mg/mL pAcFRS, 2 mM pAcF, and 10 ng/μL o-tz-tRNA) chosen for use in further experiments FIG. 10. C321.ΔA.759.T7.D is a highly-efficient platform for one-pot NSAA incorporation. (a) sfGFP produced in vitro from cell extracts derived from induced BL21 Star™ (DE3) cells as well as C321.ΔA.759.T7.D cells, both with and without supplementation with purified 17 RNAP. The indicated sfGFP amber mutant variants were synthesized in the presence of the complete pAcF OTS. At least 3 independent reactions were performed per condition, and one standard deviation is shown. (b) Illustration of both the wild type (WT) and amber mutant (TAG) ELP monomer used in this study. (c) Autoradiogram of ELPmers produced by C321.ΔA.759.T7.D lysates under the indicated reaction conditions. (d) Radioactive count quantification of ELPmers produced by C321.ΔA.759.T7.D lysates under the indicated conditions. At least 3 independent reactions were performed per condition, and one standard deviation is shown. The results indicate that C321.ΔA.759.T7.D outperforms BL21 Star™ (DE3) both with and without T7RNAP supplementation as the number of NSAA incorporations increases. pAcF is required for visible production of ELPmer constructs, speaking to the fidelity of the pAcF OTS and suggesting that most amber codons are suppressed by pAcF. C321.ΔA.759.T7.D produces high titers of ELPmer (up to 100 μg/mL) and can produce respectable amounts of amber mutant protein even in the absence of supplemental polymerase.
Figure 9:
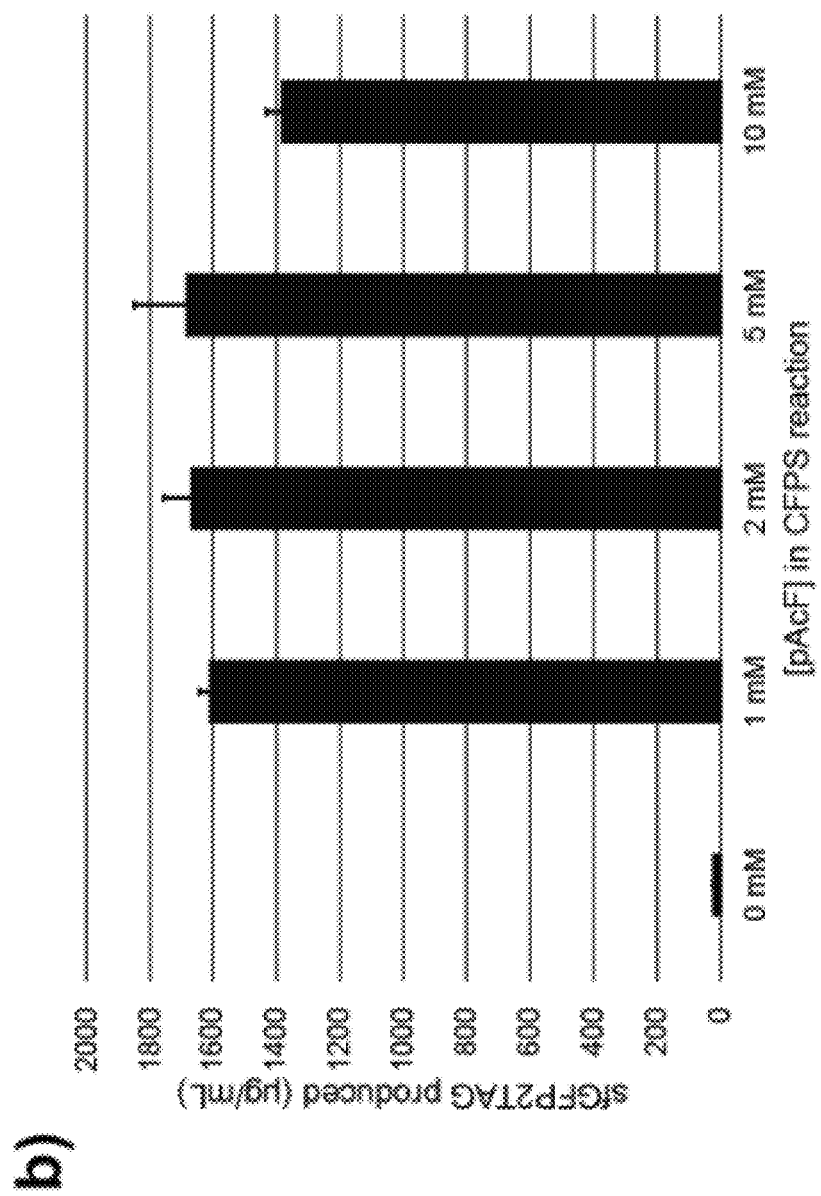
Figure 9:
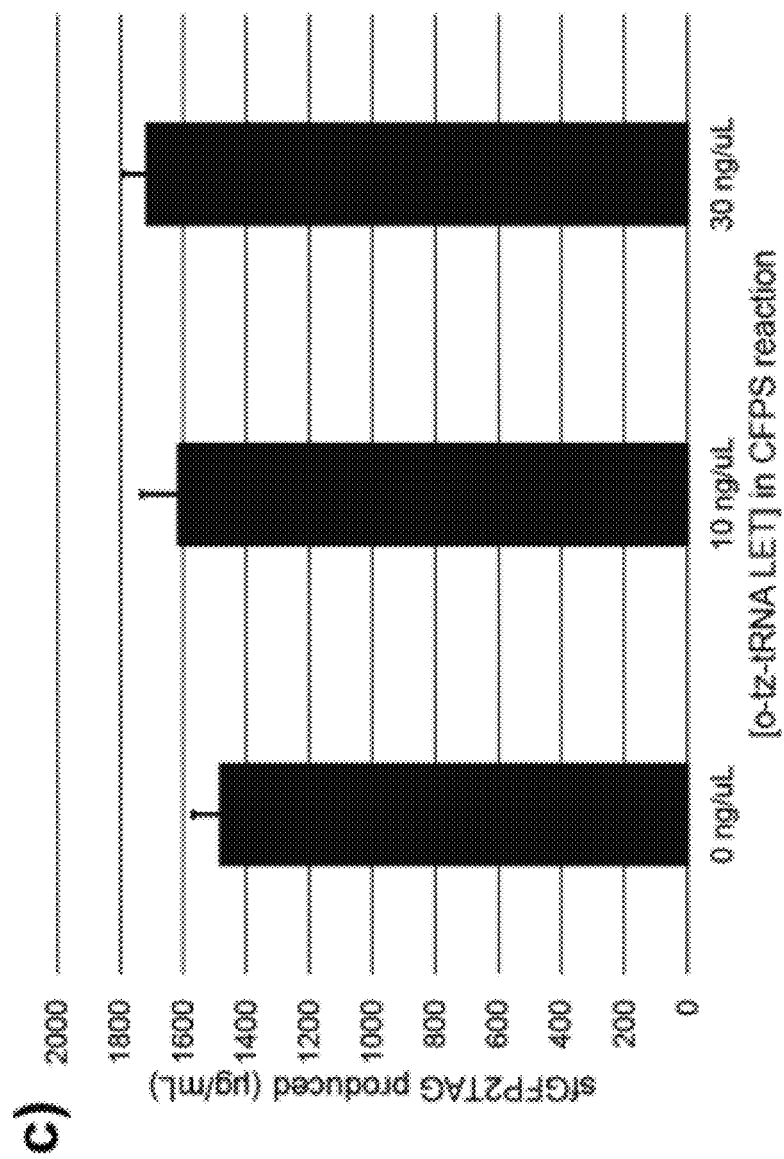

We next investigated the kinetics of the system and compared it with established CFPS platforms. Batch CFPS reactions using lysates derived from IPTG-induced populations of C321.ΔA.759, BL21 Star™ (DE3) (Invitrogen, Carlsbad, Calif.), and C321.ΔA.759.T7 were performed over 20 h at 30° C., directed to synthesize sfGFP both with and without T7RNAP supplementation. Samples from each condition were collected over the course of the reaction for analysis, with mRNA quantification determined by measuring $^3$H-labeled UTP incorporation (FIG. 3C) and protein quantification determined by the emergence of sfGFP fluorescence (FIG. 8). All systems demonstrated rapid protein production during the first four hrs of the CFPS reaction, which is consistent with previous observations. Consistent with endpoint measurements, C321.ΔA.759 and C321.ΔA.759.T7 lysates with supplemental T7RNAP eventually overtake the other conditions to produce high levels of sfGFP fluorescence. C321.ΔA.759.T7 lysate fluorescence without additional polymerase trended similarly to both BL21 Star™ (DE3) conditions, while C321.ΔA.759 lysate without T7RNAP added produced no fluorescence at all. mRNA quantification revealed that BL21 Star™ (DE3) lysates are exceptionally transcriptionally active, with peak mRNA levels significantly higher than those produced in lysates from either C321.ΔA-derived strain even with T7RNAP supplemented. Conversely, the innate transcriptional capacity of C321.ΔA.759.T7 lysate is fairly low despite the relatively aggressive overexpression of T7RNAP in the strain. Western blot analysis of samples derived from C321.ΔA.759.T7 revealed that the T7RNAP produced by the strain is cleaved near the N-terminus to yield a ~21 kDa fragment (FIG. 2C). This cleavage is well documented, and previous work has identified the membrane-bound periplasmic protease OmpT as the responsible agent in *E. coli*[43]. The cleaved polymerase itself has been heavily characterized, and prior work has concluded that the nicked enzyme is significantly impaired by a loss in polymerase activity and efficiency[44-46]. Thus, we reasoned that OmpT-mediated proteolysis of the T7RNAP expressed by C321.ΔA.759.T7 during cell lysis contributed to the reduced capacity of the resulting lysates to support transcription independent of supplemental T7RNAP.

ompT Inactivation to Protect T7RNAP During C321.ΔA.759.T7 Crude Lysate Preparation.

BL21 (DE3) and its derivative strains all feature a deletion at the ompT locus which presumably prevents the proteolytic degradation of the T7RNAP produced by those strains[47]. Based on this, we hypothesized that a deletion at the ompT locus of C321.ΔA.759.T7 would similarly protect strain-synthesized T7RNAP and thus eliminate the strain's partial dependence on supplemental polymerase in CFPS. To test this, we first "looped" kanR out of the C321.ΔA.759.T7 genome using multiplex advanced genome engineering (MAGE)[33]. Next, we applied λHR to replace a ~12 kbp region of the C321.ΔA.759.T7 genome analogous to the spontaneous ompT deletion in BL21 (DE3) with a kanR cassette to select for successful integrants. MASC-PCR verified the knockout, yielding strain C321.ΔA.759.T7.ΔompT.

Figure 3:
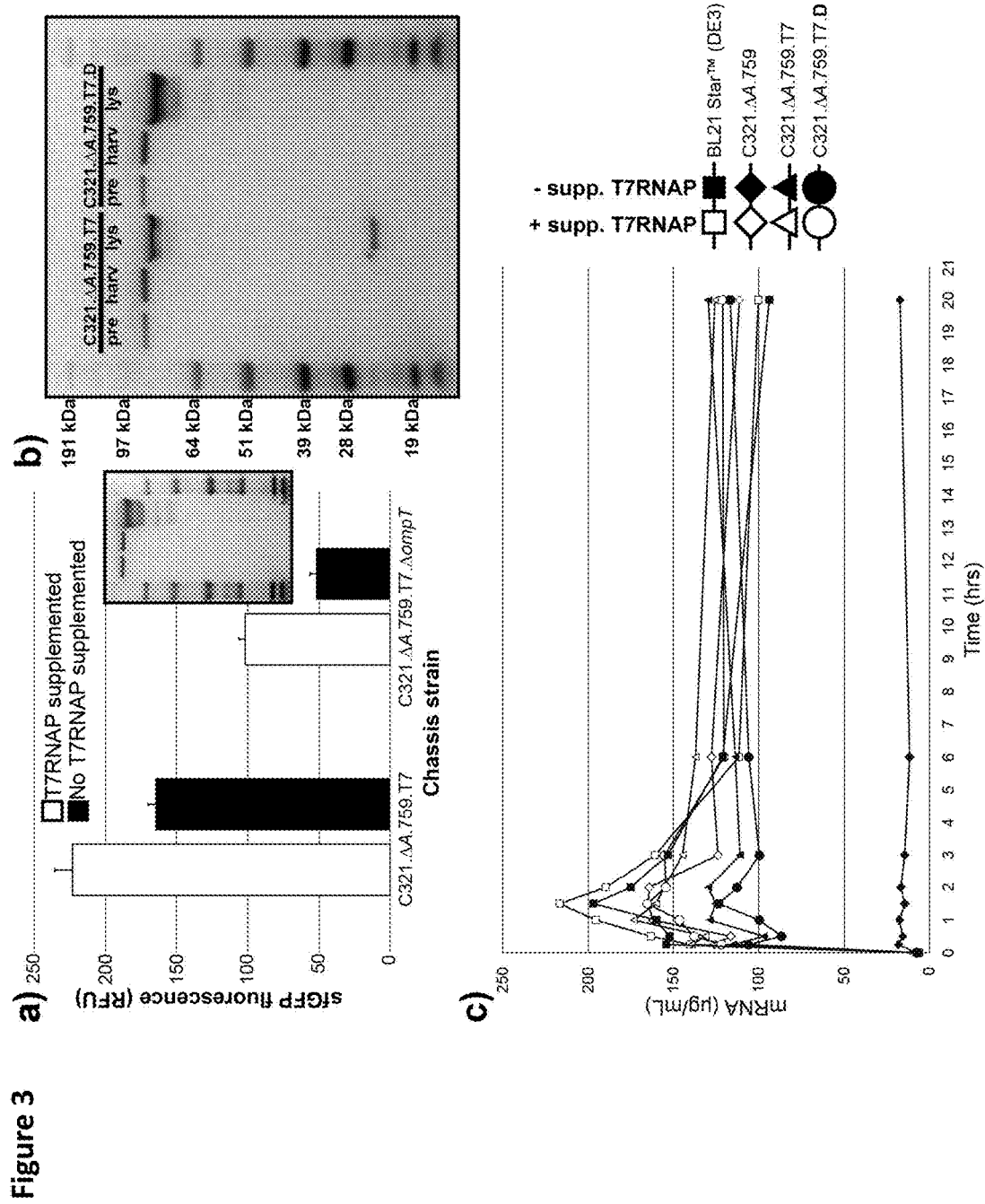
FIG. 3. Engineering an OmpT-resistant T7 polymerase. (a) Characterization of C321.ΔA.759.T7 and C321.ΔA.759.T7.ΔompT. Extracts from each strain were directed to synthesize sfGFP in CFPS both with and without supplementation with purified T7 RNAP, and fluorescence was measured after incubation for 20 hours at 30 C. Three independent CFPS reactions were performed for each condition, and one standard deviation is shown. Inset: α-His western blot characterization of C321.ΔA.759.T7.ΔompT. (b) α-His western blot comparison of C321.ΔA.759.T7 and C321.ΔA.759.T7.D. (c) mRNA and protein synthesis timecourse comparison between BL21 Star™ (DE3), C321.ΔA.759, C321.ΔA.759.T7 and C321.ΔA.759.T7.D. Extracts derived from these strains were directed to synthesize the sfGFP in vitro. Reactions were performed in both the presence (+T7RNAP) and absence (−T7RNAP) of supplemental T7 RNA polymerase. mRNA abundance (via $^3$H-UTP detection) was measured over the course of 20 hours at 30° C. Two independent reactions were performed for each condition. The results indicate that removal of functional ompT from the strain eliminates proteolytic cleavage of the polymerase, but significantly reduces the overall productivity of the strain in CFPS. Mutation of 2 lysine residues generates a T7RNAP mutant that can no longer be acted on by OmpT and remains intact even in the presence of active protease. The strain C321.ΔA.759.T7.D eventually synthesizes more protein than any progenitor strain, though the mRNA timecourse suggests that the uncleaved mutant polymerase is not much more productive than the cleaved wildtype polymerase.

To assess the cell-free capabilities of the ompT-deficient strain, we prepared crude S30 extracts from culture induced with 1 mM IPTG for analysis via both Western blot and batch CFPS reactions. As expected, a Western blot revealed that in the absence of OmpT the T7RNAP is no longer cleaved (FIG. 3A, inset). Unfortunately, batch sfGFP CFPS reactions demonstrated that the strain's ability to perform CFPS suffered significantly overall in response to the ompT knockout (FIG. 3A). As compared to C321.ΔA.759.T7 lysate, C321.ΔA.759.T7.ΔompT lysates show a 2-3 fold reduction in CFPS yields both with and without T7RNAP supplementation. This is consistent with earlier work demonstrating that functional OmpT is critical for robust protein synthesis in lysates derived from C321.ΔA and its descendants. We concluded that this was not a viable strategy for improving C321.ΔA.759.T7 and discontinued our pursuit of this scheme for preventing T7RNAP cleavage during cell lysis.

Engineering a Protease-Resistant T7RNAP.

We next considered a chemical biology approach to protecting the T7RNAP produced by C321.ΔA.759.T7 from proteolysis during lysate preparation. We reasoned that since the source of the degradation could not be removed without deleterious effects on the strain's productivity in vitro, perhaps the T7RNAP could be mutated such that it would no longer be an efficient substrate for OmpT. OmpT binds its substrates at pairs of adjacent basic residues and catalyzes hydrolysis of the amide bond linking them[48]. The requirement of basic residues for OmpT activity at the cleavage site is fairly rigid—in particular, the 1' residue residing immediately upstream of the polypeptide cut site must be basic in order for OmpT to facilitate hydrolysis. In T7RNAP, two such sites have been identified proximal to the enzyme's N terminus at K172/R173[45] (site A, K183/R184 in His-tagged mutant polymerase) and K179/K180[44] (site B, K190/K191 in His-tagged mutant polymerase). These sites are relatively close together such that OmpT proteolysis at either would liberate a ~21 kDa N-terminal fragment, consistent with what was observed on our C321.ΔA.759.T7 western blot.

Figure 4:
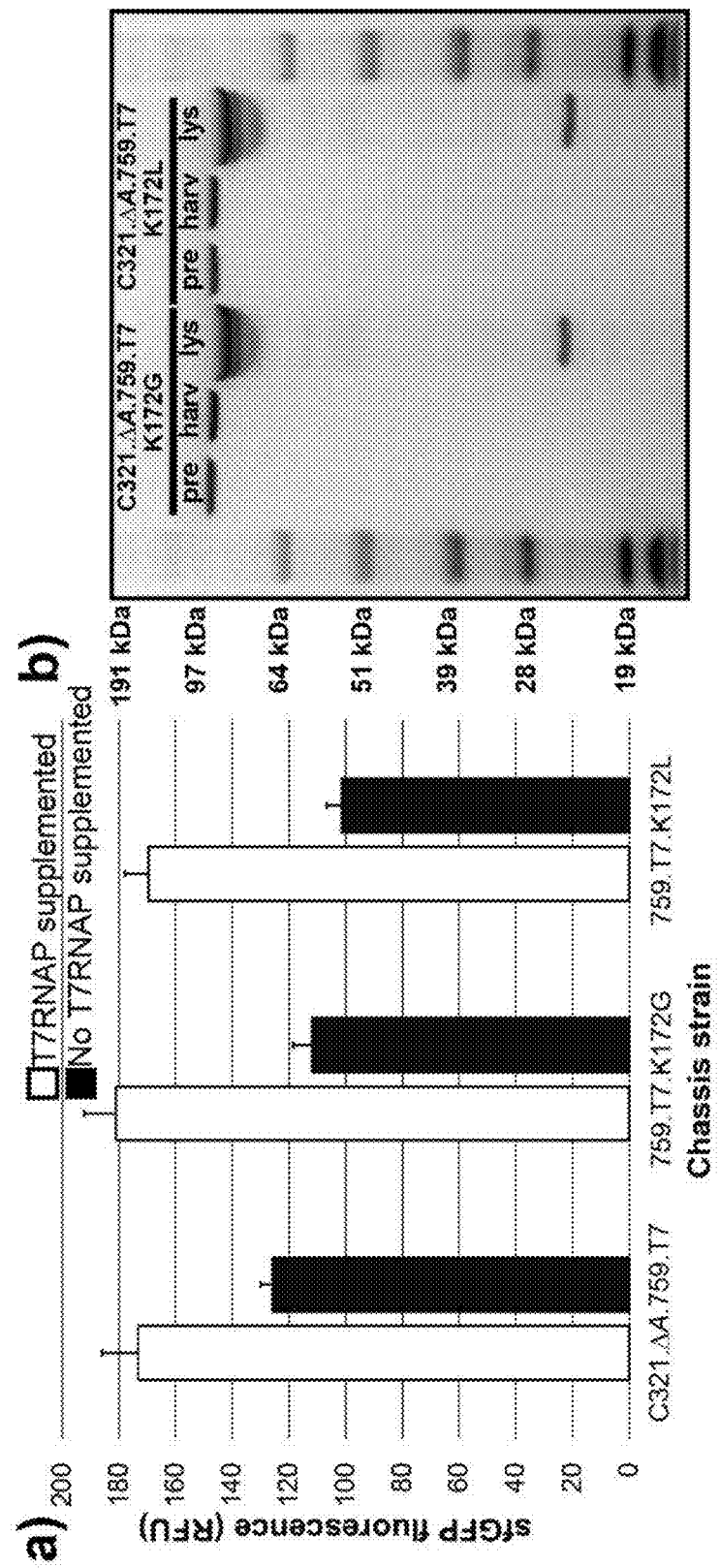
FIG. 4. Single lysine mutations are insufficient to confer resistance to OmpT proteolysis. Comparison between C321.ΔA.759.T7 and mutant strains in which K172 has been mutated to glycine (C321.ΔA.759.T7.K172G) or leucine (C321.ΔA.759.T7.K172L). (a) Characterization of the K172 mutants in CFPS. Lysates derived from C321.ΔA.759.T7 and the K172 mutant strains were directed to synthesize sfGFP in CFPS both with and without supplementation with purified T7 RNAP, and fluorescence was measured after incubation for 20 hours at 30° C. Three independent CFPS reactions were performed for each condition, and one standard deviation is shown. (b) α-His western blot comparison of the K172 mutant strains. The results indicate that K172 mutants are functional but do not perform better than the wildtype T7RNAP. CFPS productivity is comparable if not a bit worse than the wildtype. OmpT is still able to recognize and cleave the polymerase and release a ~20 kDa N-terminal fragment. A single lysine mutation is insufficient to confer complete protection from the activity of OmpT.

Because site A was previously identified as the primary site of OmpT activity in T7RNAP[45], we hypothesized that mutating K183 to a non-basic residue would abolish the target site and thus protect the polymerase from proteolysis despite the presence of fully functional OmpT in the lysate. To test this, we used MAGE to edit the sequence of the 1 gene on the genome of C321.ΔA.759.T7 to mutate K183 to either glycine or leucine, as these mutants had previously been shown to retain robust polymerase activity[49]. Mutations were detected using allele-specific primers in MASC-PCR and confirmed by Sanger sequencing. Analysis of crude extracts prepared from each mutant strain revealed that despite the installed mutations, the polymerase was still being cleaved during cell lysis (FIG. 4B). When the extracts were directed to synthesize sfGFP in batch CFPS reactions both with and without supplemental T7RNAP, neither performed better than C321.ΔA.759.T7 (FIG. 4A).

Figure 5:
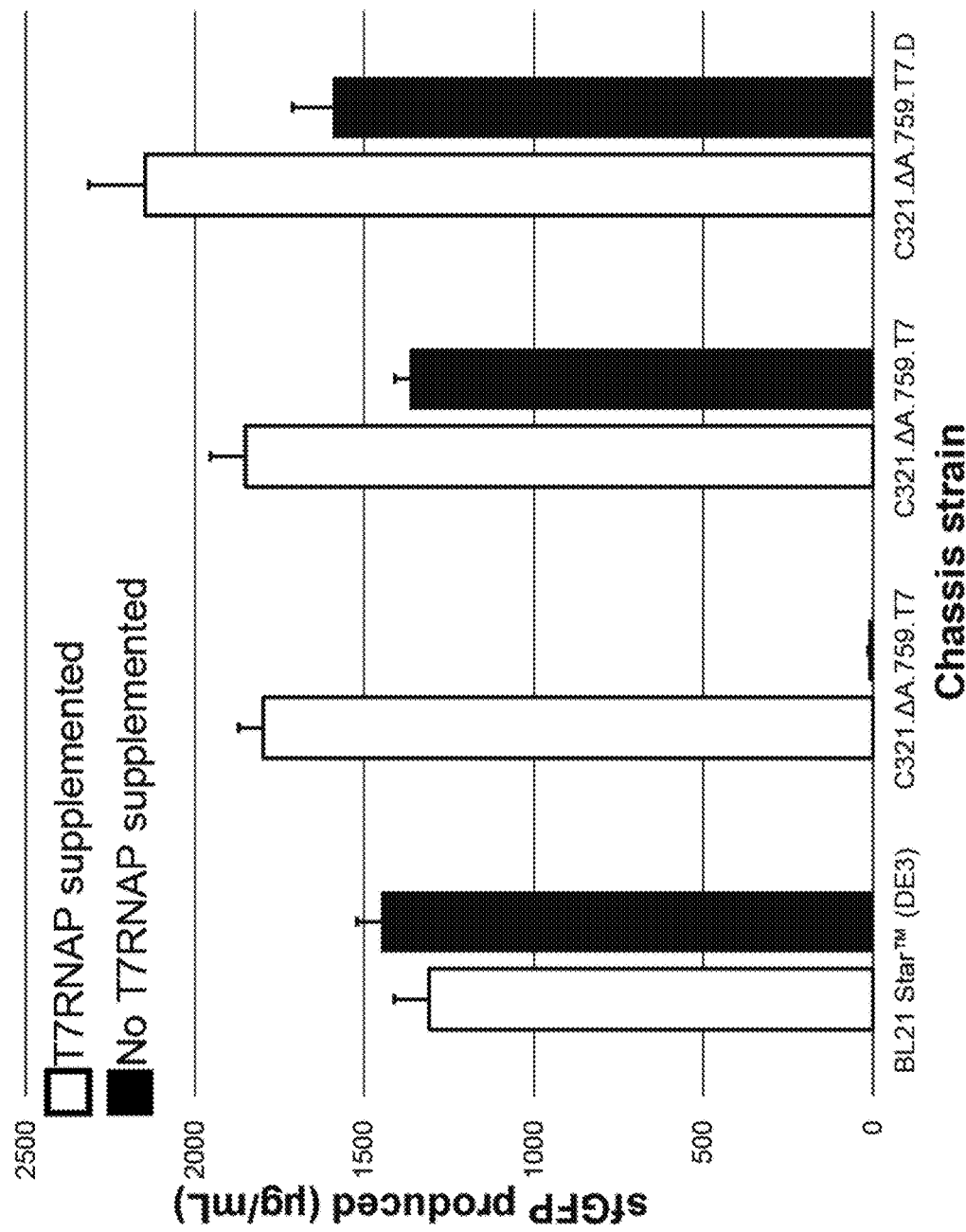
FIG. 5. The strain C321.ΔA.759.T7.D is a highly-productive, one-pot CFPS system. A side-by-side comparison of sfGFP produced in CFPS using crude lysates derived from IPTG-induced BL21 Star™ (DE3), C321.ΔA.759, C321.ΔA.759.T7, and C321.ΔA.759.T7.D cells. Shown are results from CFPS reactions performed both with and without supplementation with purified T7RNAP. At least 3 independent reactions were performed per condition, and one standard deviation is shown. The results indicate that the strain C321.ΔA.759.T7.D has higher productivity in CFPS than CFPS systems derived from state-of-the-art protein expression strain BL21 Star™ (DE3). Tde strain C321.ΔA.759.T7.D is capable of robust CFPS without supplementation with purified T7RNAP, a significant improvement on C321.ΔA.759 which is completely dependent upon exogenous polymerase to perform CFPS.

Next, we reasoned that while site A may be the preferential site for proteolysis when both sites are present, in the absence of a functional site A OmpT may simply cleave at site B instead. We hypothesized that the simultaneous elimination of both sites may be necessary to fully prevent the ability of OmpT to bind and cleave the polymerase. To test this, we again exploited MAGE to edit the sequence of 1 on the C321.ΔA.759.T7 genome and install the mutations K183G and K190L. Mutations were detected using allele-specific primers in MASC-PCR and confirmed via Sanger sequencing. We prepared crude cell lysates from the resulting strain, C321.ΔA.759.T7.D, for Western blot and CFPS analysis. The western blot revealed that the double mutant T7RNAP expressed by C321.ΔA.759.T7.D is not cleaved despite the presence of active OmpT in the cellular lysate (FIG. 3B). In batch mode CFPS reactions, C321.ΔA.759.T7.D lysates exhibit a ~15% increase in productivity over C321.ΔA.759.T7, producing ~2.2 g/L and ~1.6 g/L of sfGFP with and without T7RNAP supplementation respectively (FIG. 5). C321.ΔA.759.T7.D lysates also significantly outperform both BL21 Star™ (DE3) and C321.ΔA.759 lysates regardless of T7RNAP supplementation, establishing it as a robust one-pot CFPS system and one of the most productive CFPS platforms developed to date.

Characterization of C321.ΔA.759.T7.D Lysates In Vitro.

Figure 6:
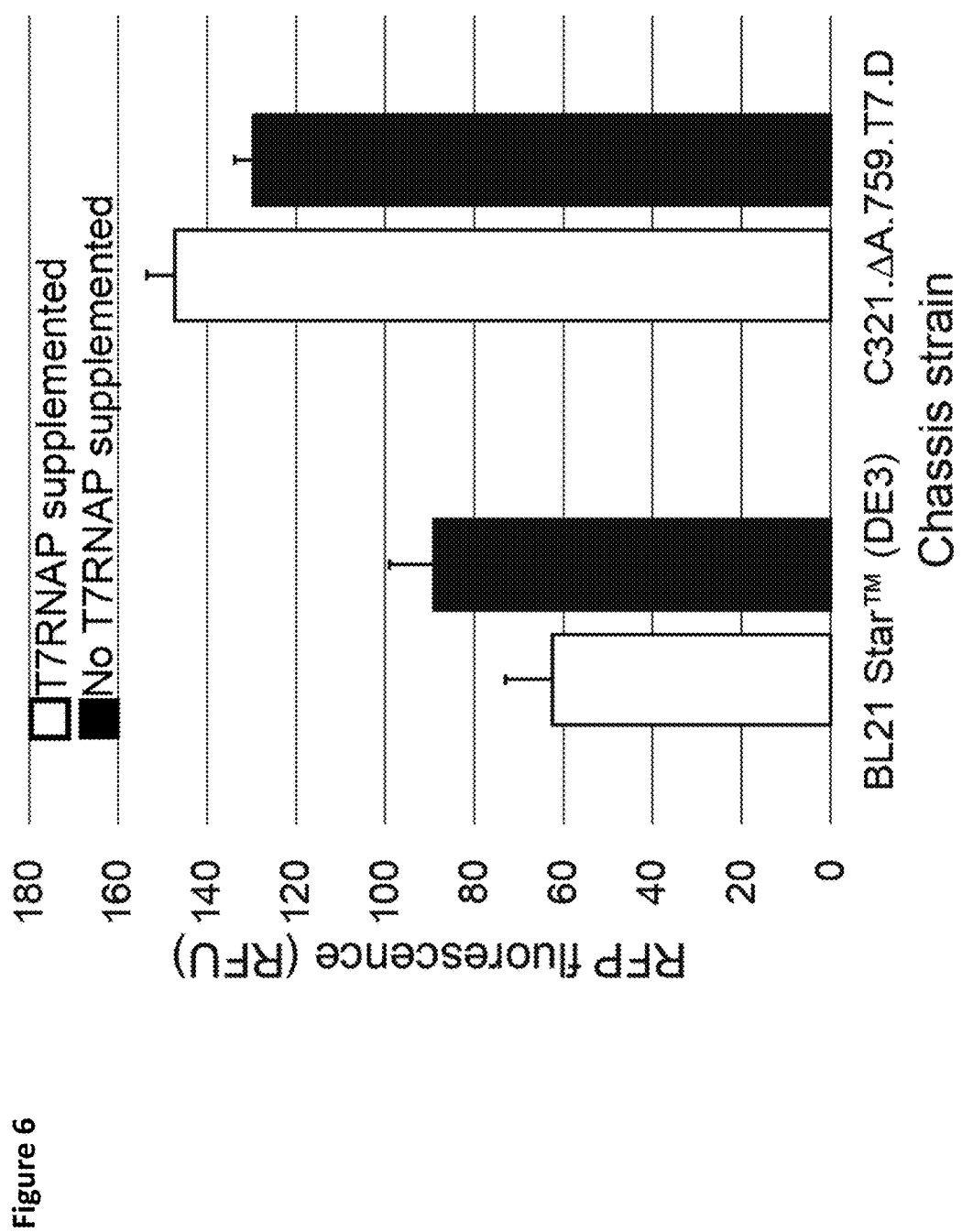
FIG. 6. C321.ΔA.759.T7.D is a highly-productive, one-pot system for general protein synthesis. Comparison of general protein synthesis using BL21 Star™ (DE3) and C321.ΔA.759.T7.D. Extracts derived from the listed strains were directed to synthesize RFP with and without supplementation with purified T7RNAP. RFP fluorescence was measured following a 20 hr incubation at 30° C. Three independent CFPS reactions were performed for each condition, and one standard deviation is shown. The results indicate that strain C321.ΔA.759.T7.D significantly outperforms BL21 Star™ (DE3) in the synthesis of a protein other than sfGFP, supporting the notion that the effect is not sfGFP-specific.
Figure 7:
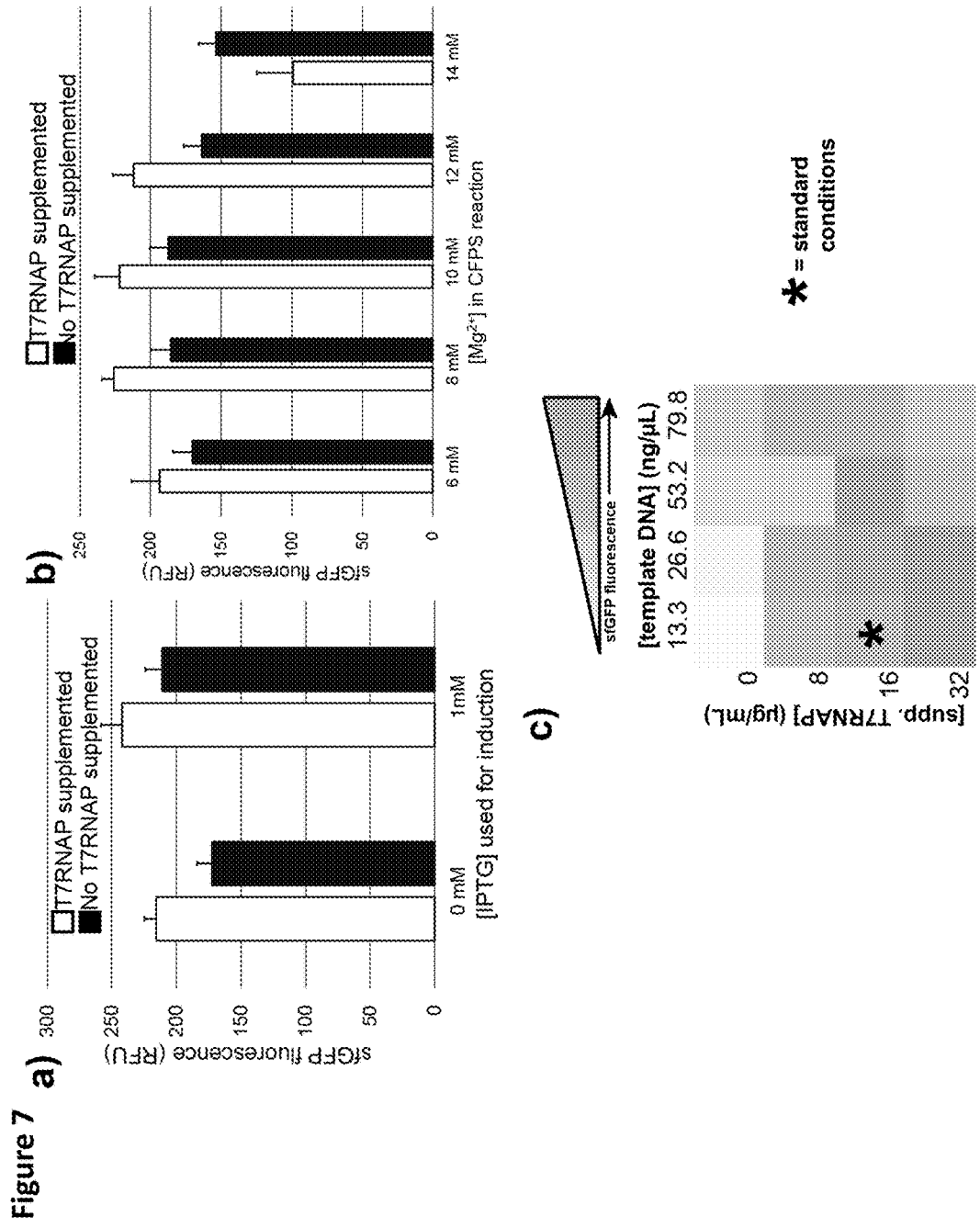
FIG. 7. Optimization of CFPS reactions conditions for C321.ΔA.759.T7.D lysates. (a) Characterization of C321.ΔA.759.T7.D lysates derived from cell cultures induced with 0 mM or 1 mM IPTG. These extracts were directed to synthesize sfGFP in CFPS both with and without supplementation with purified T7 RNAP, and fluorescence was measured after incubation for 20 hours at 30° C. Three independent CFPS reactions were performed for each condition, and one standard deviation is shown. (b) Optimization of [Mg$^{2+}$] in C321.ΔA.759.T7.D CFPS reactions. Reactions containing the indicated concentrations of Mg$^{2+}$ were performed, with the extract directed to synthesize sfGFP in CFPS both with and without supplementation with purified T7 RNAP. Fluorescence was measured after incubation for 20 hours at 30 C. Three independent CFPS reactions were performed for each condition, and one standard deviation is shown. (c) Optimization of [supplemental T7RNAP] and [template DNA] in C321.ΔA.759.T7.D reactions. The results indicate that the strain C321.ΔA.759.T7.D yields a potent one-pot CFPS platform even without IPTG induction of additional TRNAP expression. The results also indicate that C321.ΔA.759.T7.D lysates have a lower demand for Mg$^{2+}$ than other C321-derived strains. Finally, the results indicate that lysates from the strain C321.ΔA.759.T7.D benefit marginally from addition of significantly increased levels of supplemental polymerase and template DNA, but that the increases are negligible.

We next set out to characterize the system. To demonstrate generality, batch CFPS reactions were performed using C321.ΔA.759.T7.D and BL21 Star™ (DE3) lysates directed to synthesize red fluorescent protein (mRFP) over 20 h at 30° C. both with and without T7RNAP supplementation. Under both conditions, C321.ΔA.759.T7.D generated significantly higher levels of RFP fluorescence (FIG. 6). To explore the induction response of the IPTG-inducible T7RNAP expression cassette, we harvested cell populations of C321.ΔA.759.T7.D induced during exponential growth phase with either 0 mM or 1 mM IPTG and prepared lysates from each for testing in CFPS reactions. While these experiments confirmed that maximum IPTG induction yielded the most productive lysates, we observed that even in the complete absence of IPTG induction C321.ΔA.759.T7.D lysates still synthesize enough polymerase to facilitate robust protein synthesis in vitro (FIG. 7A). As $Mg^{2+}$ is a critical factor for both ribosome assembly[50] and T7RNAP function[51], we also optimized the $Mg^{2+}$ content of the cell-free reaction environment (FIG. 7B). Exploratory CFPS reactions featuring increased levels of supplemental T7RNAP and plasmid DNA template revealed that even significant increases in the concentrations of these components in the cell-free environment provided negligible benefit to the amount of protein produced (FIG. 7C). Finally, we investigated the kinetics of the translational components as compared to the progenitor C321.ΔA.759.T7 strain. As above, batch CFPS reactions using lysates derived from IPTG-induced populations of C321.ΔA.759.T7.D were performed over 20 h at 30° C., directed to synthesize sfGFP both with and without T7RNAP supplementation. Samples from each condition were collected over the course of the reaction for analysis, with mRNA quantification determined by measuring $^3$H-labeled UTP incorporation (FIG. 3C) and protein quantification determined by the emergence of sfGFP fluorescence (FIG. 8). Consistent with endpoint measurements, C321.ΔA.759.T7.D lysates generated more sfGFP fluorescence than C321.ΔA.759.T7 both with and without polymerase supplemented. Unexpectedly, the mRNA synthesis time course results suggest that both lysates drive essentially the same amount of transcription despite the polymerase remaining intact during C321.ΔA.759.T7.D lysate preparation. It is possible that the protective mutations installed in the polymerase expressed by C321.ΔA.759.T7.D impair the activity of the enzyme by other means, with the net result being no improvement to polymerase performance. Alternatively, it may be the case that at least in the context of CFPS, any impairment suffered by the T7RNAP as a result of OmpT-mediated proteolysis has no effect on the total amount of protein produced by the system. In any case, the tangible increases in protein yield by C321.ΔA.759.T7.D lysates as compared to C321.ΔA.759.T7 lysates are likely not a result of improved T7RNAP function, and may be attributable to the occurrence of random beneficial mutations during strain engineering.

Demonstration of Capacity for Multiple NSAA Incorporations Using T7RNAP-Expressing Strains.

Finally, we assessed the capacity for C321.ΔA.759.T7.D lysates to produce proteins featuring NSAAs. Because the parent strain had RF1 removed[30], we expected NSAA incorporation via amber suppression would be highly efficient—indeed, a previous effort using a recoded strain confirmed up to 40 NSAA incorporations in a single peptide. Both C321.ΔA.759.T7.D and BL21 Star™ (DE3) were transformed with a pEVOL plasmid encoding the orthogonal translation system (OTS) components for the NSAA p-acetyl-L-phenylalanine (pAcF)[52], namely the pAcF-specific aminoacyl-tRNA synthetase (pAcFRS) and an orthogonal suppressor tRNA engineered to decode the amber codon (o-tRNA)[53]. pEVOL-pAcF features two copies of the pAcFRS gene—one regulated by the constitutive glnS promoter to establish a basal amount of synthetase expression, as well as one regulated by the arabinose-inducible araBAD promoter to drive robust overexpression during exponential cell growth. The transformed strains were cultured, with 1 mM IPTG added during exponential growth to induce expression of T7RNAP. However, we decided not to induce the second copy of the pAcFRS gene, as previous work in our group using pEVOL-pAcF demonstrated that while the amount of pAcFRS produced off of the constitutive copy of the synthetase gene is insufficient to catalyze robust pAcF incorporation in CFPS, further synthetase overexpression via arabinose induction typically leads to increases in cell doubling time accompanied by significant reductions in lysate productivity as a result of the enzyme's cytotoxicity. Instead, pAcF incorporation using these lysates was enabled by supplementing purified pAcFRS enzyme directly to CFPS reactions.

Figure 10:
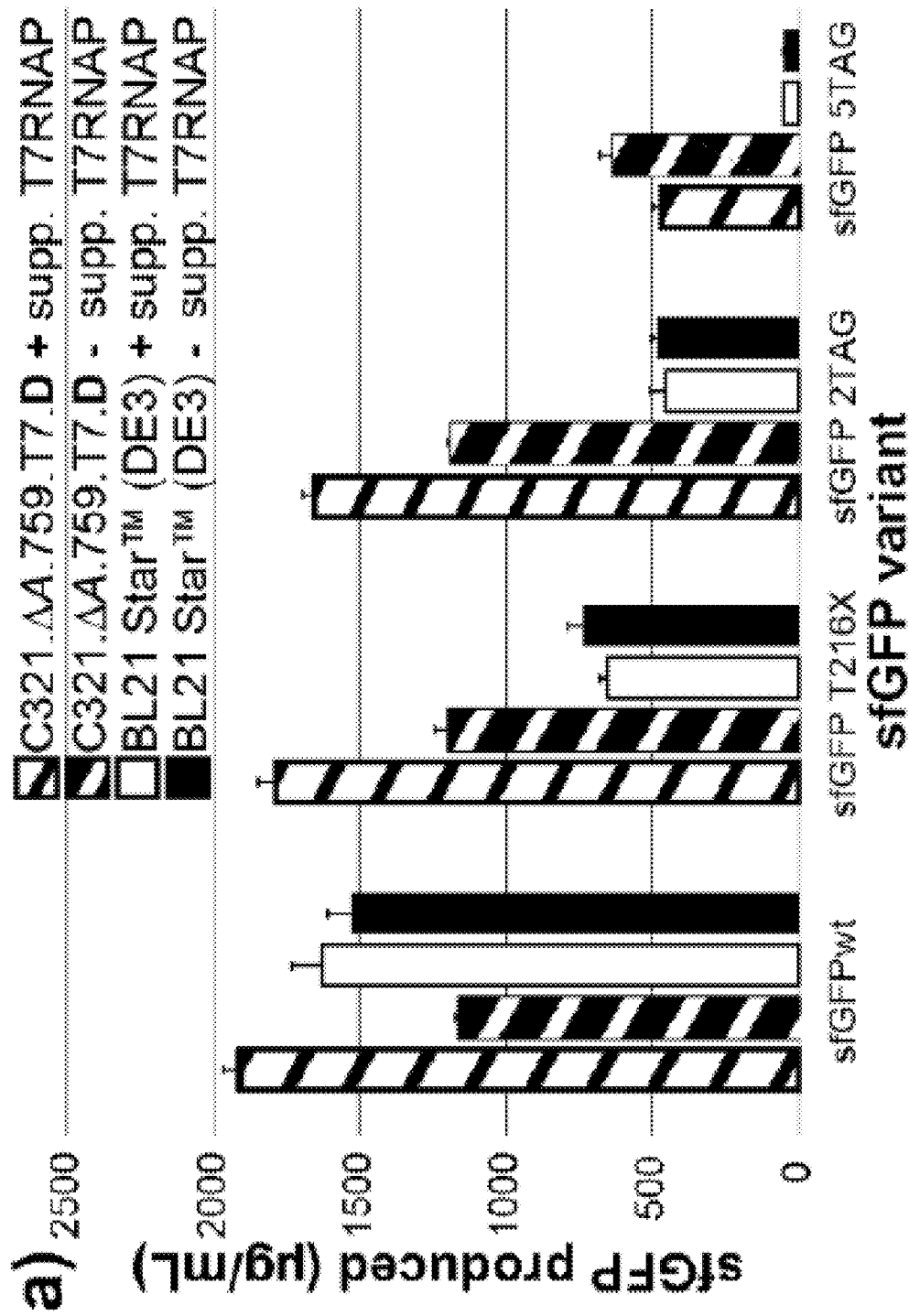
Figure 10:
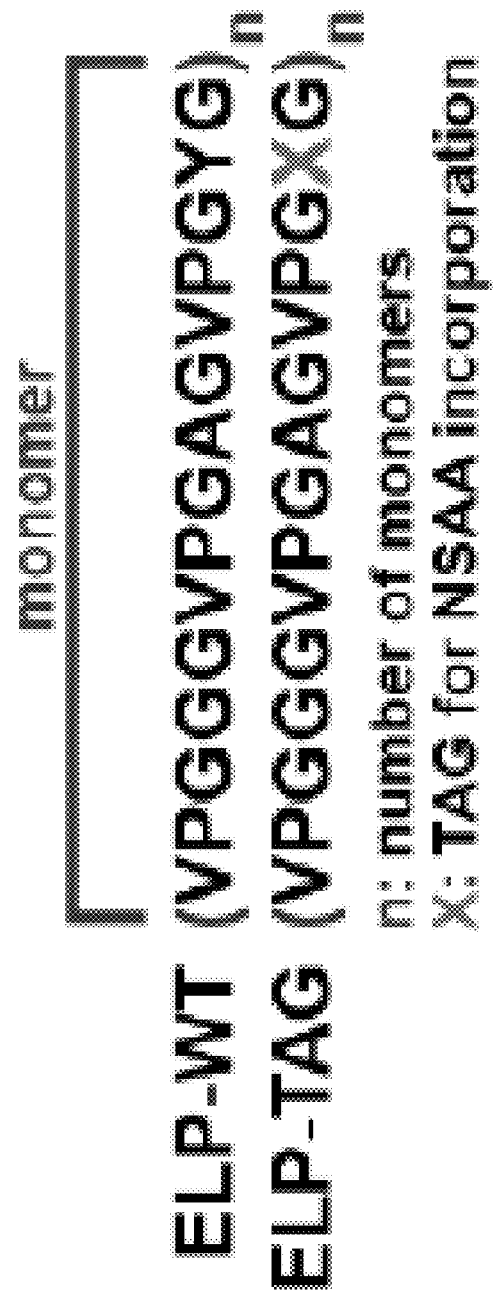
Figure 10:
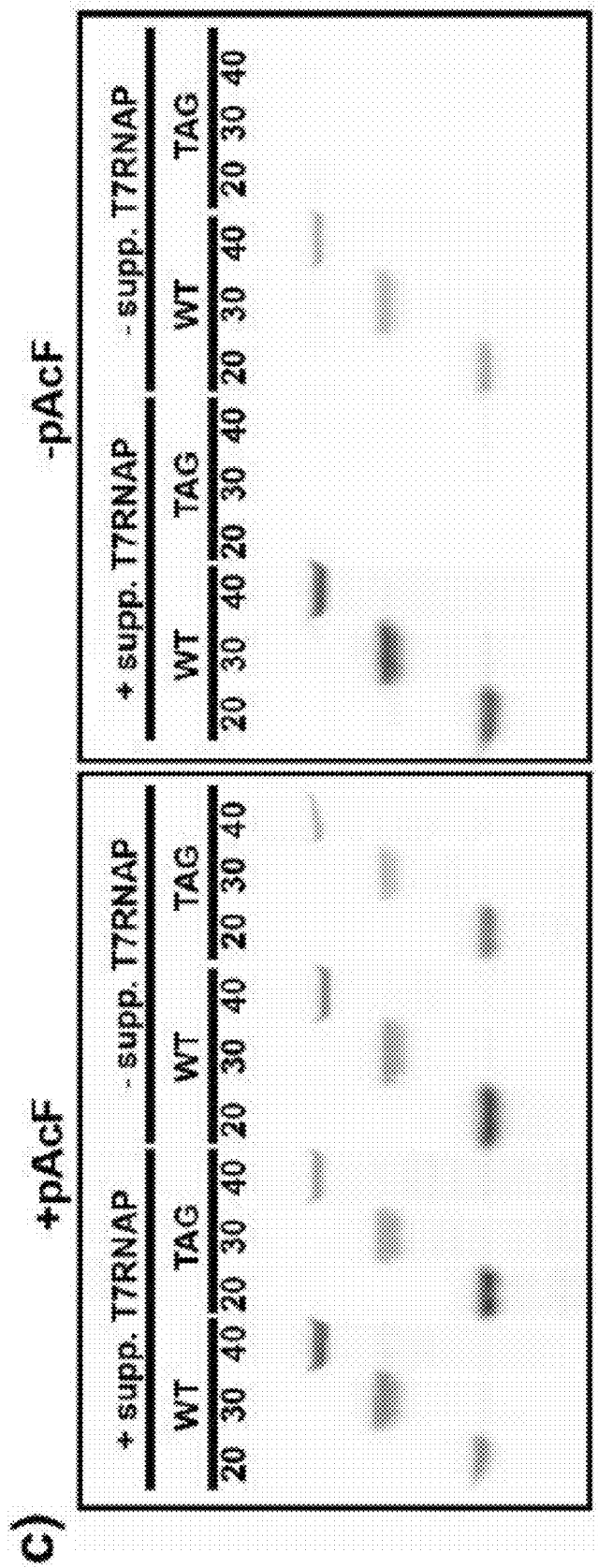
Figure 10:
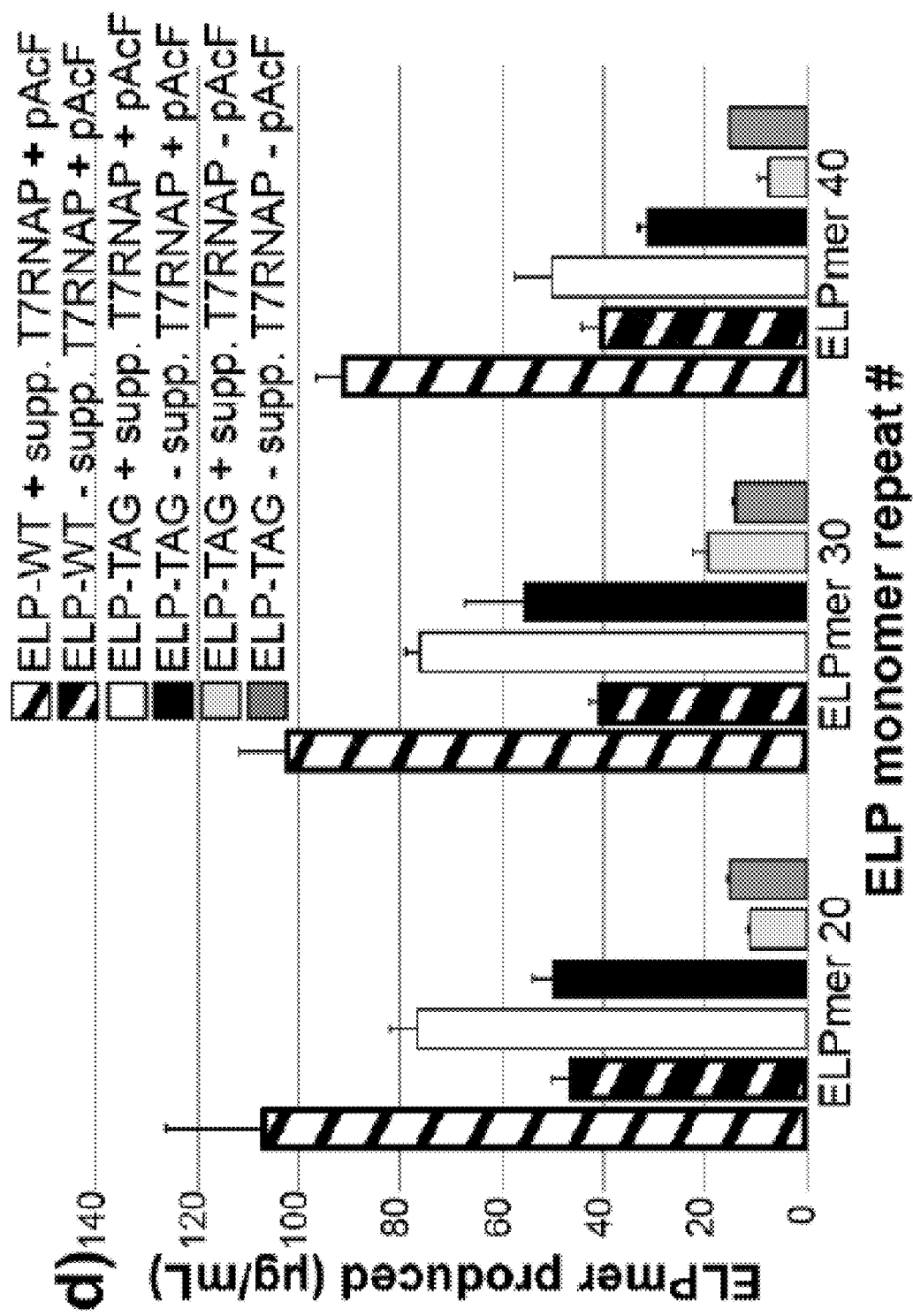

As an initial demonstration of NSAA incorporation, we directed the lysates derived from these pEVOL-bearing strains to synthesize amber mutant variants of sfGFP. We first established the optimal concentrations of pAcF OTS components to be supplied to these CFPS reactions via a series of CFPS reactions directed to synthesize a sfGFP variant featuring two amber codons (sfGFP-2TAG) (FIG. 10). Using these conditions, the C321.ΔA.759.T7.D and BL21 Star™ (DE3) pEVOL-pAcF lysates were used in CFPS to synthesize wild type sfGFP (sfGFPwt), sfGFP with a single amber codon (sfGFP-T216X), sfGFP with two amber codons (sfGFP-2TAG), or sfGFP with five amber codons (sfGFP-5TAG). Reactions were performed both with and without supplementation with purified T7RNAP (FIG. 10A). As expected, regardless of T7RNAP supplementation the RF1-deficient C321.ΔA.759.T7.D lysates exhibit a significantly higher capacity for pAcF incorporation than the BL21 Star™ (DE3) lysates, with the difference becoming more pronounced as the number of pAcF incorporations increases. Indeed, C321.ΔA.759.T7.D yields ~500 μg/mL of sfGFP-5TAG both with and without T7RNAP supplementation whereas BL21 Star™ (DE3) yields essentially none. C321.ΔA.759.T7.D lysates remain highly productive for sfGFP variants bearing up to two pAcFs, yielding >1.6 g/L with and >1.2 g/L without T7RNAP supplementation for sfGFPwt, sfGFP-T216X, and sfGFP-2TAG.

We next explored the synthesis of large peptides containing multiple identical NSAAs utilizing our one-pot CFPS platform derived from C321.ΔA.759.T7.D. Elastin-like polypeptides (ELPs) are biocompatible, stimuli-responsive biopolymers that can be applied for drug delivery and tissue engineering[54]. Typically composed of repeated monomers of the pentapeptide VPGVG (a key component of elastin), ELPs exhibit self-assembly behavior, transitioning from random coil to helical configurations above transition temperature. In each monomer, the second valine residue can be replaced with any amino acid except proline while still preserving the elastin-like properties of the ELP, which opens up the possibility of modifying the temperature-sensitive features of the peptide by incorporation of NSAAs. To this end, NSAAs have been incorporated into ELPs by the replacement of canonical amino acids with non-standard mimetics[55], via amber suppression in a strain with attenuated RF1 activity[56], and via amber suppression in recoded RF1-deficient strains.

Here, we sought to produce ELPs containing NSAAs using C321.ΔA.759.T7.D lysates. Our ELP construct consisted of three pentapeptide repeats per monomer unit with a single valine codon per monomer changed to TAG in amber mutants (FIG. 10B). Lysates derived from pEVOL-bearing C321.ΔA.759.T7.D were directed to synthesize wild type (ELP-WT) and amber mutant (ELP-TAG) ELPs with 20, 30, and 40 monomer units in the presence of pAcF, both with and without supplementation with purified T7RNAP. Products were visualized using an autoradiogram, demonstrating that a high percentage of the protein produced under each condition is full-length (FIG. 10C, left). When the experiments were repeated without the addition of pAcF to reactions, synthesis of full-length ELP-WT species was unaffected but full-length ELP-TAG protein was no longer observed (FIG. 10C, right). These results demonstrate the relatively high fidelity of the pAcF OTS and suggest that the full-length ELP-TAG protein observed when pAcF is present truly feature a pAcF at the majority of amber codons. Absolute yields for each of the various ELPs were quantified via $^{14}$C-glycine radioactive scintillation counting (FIG. 10D). The lysates generated >90 mg/L and >40 mg/L of each ELP-WT with and without T7RNAP supplementation, respectively. For the ELP-TAG constructs featuring up to 30 amber codons, the C321.ΔA.759.T7.D lysates yielded >70 mg/L and >40 mg/L with and without T7RNAP supplementation, respectively. Yields from reactions not containing pAcF were extremely low (<20 mg/L), suggesting that the ELP-TAG species quantified when pAcF is present is composed of a high percentage of full-length protein featuring pAcF at the majority of TAG codons. Taken together, these results demonstrate that C321.ΔA.759.T7.D lysates are capable of catalyzing the production of proteins bearing up to 40 NSAAs independent of supplementation with T7RNAP.

Conclusions

A major limitation in the use of CFPS systems for large scale synthesis of useful, high value products is the cost associated with supplementing the reaction contents with all of the biological components required to catalyze TX/TL. One-pot systems, such as those derived from the state-of-the-art protein overexpression strain BL21 Star™ (DE3), are highly desirable due to their enrichment with critical enzymes such as T7RNAP. While extremely robust and versatile, these existing platforms struggle with the production of peptides containing NSAAs due to the competitive action of RF1 in the reaction environment. In this study, we describe the generation and utilization of a highly productive one-pot CFPS platform beginning with C321.ΔA.759, a genomically recoded RF1-deficient strain that was previously optimized for CFPS. We integrated a series of DNA constructs into the genome of C321.ΔA.759, each of which featured the T7RNAP-encoding gene 1 under the control of one of three different promoter sequences of varying potency. The construct featuring 1 regulated by strong promoter Lpp5 integrated at a previously identified high-expression genomic locus yielded C321.ΔA.759.T7, which was capable of supporting in vitro transcription independent of supplementation with purified T7RNAP. When used in CFPS, C321.ΔA.759.T7 lysates yielded ~85% as much sfGFP without T7RNAP supplementation as with. In an effort to address the continuing partial dependence of the system on polymerase supplementation, we explored different strategies to protect the T7RNAP expressed in C321.ΔA.759.T7 from OmpT-mediated proteolysis during lysate preparation. By mutating two lysine residues proximal to the N-terminus of 1, we were able to abolish the putative OmpT target sites and establish an OmpT-resistant mutant version of T7RNAP in our final strain C321.ΔA.759.T7.D. C321.ΔA.759.T7.D lysates are highly productive, yielding ~2.2 g/L sfGFP with and ~1.6 g/L sfGFP without T7RNAP supplementation. We also demonstrated the merits of RF1-deficient systems for NSAA incorporation, highlighting the significantly increased capacity for amber suppression in C321.ΔA.759.T7.D lysates as compared to BL21 Star™ (DE3). Furthermore, we were able to confirm the synthesis of full-length peptides containing up to 40 NSAAs without the addition of purified T7RNAP using C321.ΔA.759.T7.D lysates.

Looking forward, one intriguing avenue for future efforts is the continued development of C321.ΔA.759.T7.D for improved productivity and enhanced functionality in CFPS. This might be achieved by correcting some of the potentially-harmful off-target mutations incurred during the initial recoding of the strain. Additionally, upregulation of other positive effectors of CFPS (chaperones, elongation factors, energy regeneration enzymes, etc.) could be achieved via genomic integration using a strategy similar to that employed in this study. In particular, the development of orthogonal synthetases with improved kinetics and substrate specificity is a critical hurdle that must be overcome before these enzymes can be overexpressed in CFPS chassis strains without deleterious effects on cellular health and lysate performance[26].

Developing efficient CFPS systems specialized for NSAA incorporation is important for synthetic biology for various emerging applications. Powerful one-pot production platforms will support the large-scale synthesis of protein products featuring novel structures and functions, in turn promoting the mass production of potent therapeutics and materials. We anticipate that CFPS platforms such as that derived from C321.ΔA.759.T7.D are exceptionally promising for these and other synthetic biology applications.

Methods

Strains and Plasmid Maintenance.

Carbenicillin (50 µg/mL) was used for culturing C321.ΔA.759, kanamycin (50 µg/mL) was used for culturing C321.ΔA.759 T7RNAP linear insert transformants and maintaining pY71/pJL1-based plasmids, and chloramphenicol (34 µg/mL) was used to maintain the pEVOL-pAcF plasmid.

DNA Gel Electrophoresis.

Unless otherwise stated, all DNA electrophoresis was done in 1% agarose gels stained with SYBR® Safe (Thermo Fisher Scientific, Inc., Waltham, Mass.). Samples were run at 100V for 30-60 minutes on a Mini Gel II Complete Electrophoresis System (VWR, Radnor, Pa.). 100 bp and 1 kb Quick-Load® DNA Ladders (New England Biolabs, Ipswich, Mass.) were used for fragment size reference.

T7RNAP Linear Insert Construction.

The six T7RNAP-encoding inserts used in this study were assembled from PCR products obtained using designed primers. The insert loci were at coordinates 3,986,255 (asl) and 805,473 (int) in the genome of C321.ΔA.759. In brief, each insert was assembled from four segments of linear DNA—a promoter segment featuring 50 base pairs of sequence homology to the genome of C321.ΔA.759 upstream of the targeted insert site, a T7RNAP segment containing the 1 gene, a terminator segment encoding the synthetic terminator sequence L3S2P21[57], and a kanR segment featuring the kanamycin resistance cassette from pKD4[31] as well as 50 bp of sequence homology to the genome of C321.ΔA.759 downstream of the targeted insert site. All constructs were designed such that coding strand would be integrated into the leading strand during genome replication. Adjacent segments featured at least 20 bp of sequence homology to one another to facilitate their assembly into a single unit of DNA, and novel sequence elements (e.g. 6His-tag and synthetic RBS sequences) were built into the 5' tails of primers. Inserts featuring the promoter Lpp5 were assembled via overlap assembly PCR (SOEing)[58] and amplified with end primers. End primer PCR reactions for these species generated a large number of off-target sequences, so full-length insert DNA was separated from other products via electrophoresis and extracted from 1% agarose gel using a DNA gel extraction kit (Product No. D2500; Omega Bio-tek, Norcross, Ga.). Inserts featuring promoters PtacI and lacUV5 were assembled together with plasmid origins of replication (p15a and pUC, respectively) via Gibson assembly to yield plasmid DNA, and these plasmids were used as template with end primers to yield the linear insert DNA. We found that the PCR products generated using this approach had a significant reduction in the prevalence of offproducts observed for the other inserts and dramatically accelerated our workflow.

Strain Transformation and Insert Verification.

The T7RNAP cassettes were inserted into the genome of C321.ΔA.759 via λHR following the protocol of Datsenko and Wanner[31]. In brief, 5 mL cultures of C321.ΔA.759 were grown in LB media (10 g/L tryptone, 5 g/L yeast extract and 10 g/L NaCl)[59] to an $OD_{600}$ of 0.6. 1.5 mL of this culture was washed twice in ice cold, sterile nuclease-free water and resuspended in 30 µL of insert DNA at a concentration of 70 ng/µL. The cell suspension was transferred to a 2 mL electroporation cuvette and DNA was introduced into cells using a Micropulse electroporator (Bio-Rad, Hercules, Calif.). Immediately following electroporation, cells were resuspended in 1 mL sterile LB media and recovered for 3 hrs at 34° C. at 250 rpm. The recovered cell culture was plated on kanamycin selective plates and permitted to grow overnight at 34° C. The following day, colonies to be screened were picked and inoculated into 100 µL of kanamycin media on a 96-well plate (Costar 3370; Corning, Corning, N.Y.) and cultured for 3 hrs at 34° C. at 250 rpm. 1 µL of each miniature culture was used as template to detect successful genomic integration of each insert by colony PCR using designed primers. Two primer pairs were used for detection such that if no insert was present, the outermost pair of primers would anneal to the flanking genomic sequence and generate a single ~500 bp product; however, if the insert was present intact at the locus both pairs of detection primers would be able to anneal and generate two products of ~1250 and ~1750 bp (FIG. 1C).

Cell extract preparation.

For rapid prototyping of engineered strains, cells were grown in 1 L of 2×YTPG media (pH 7.2) in a 2.5 L Tunair® shake flask and incubated at 34° C. at 220 rpm. Unless otherwise stated, cultures were inoculated with 1 mM IPTG at an $OD_{600}$ of 0.6 and permitted to continue to grow to an $OD_{600}$ of 3.0. Cells were pelleted by centrifuging for 15 mM at 5000×g at 4° C., washed three times with cold S30 buffer (10 mM tris-acetate pH 8.2, 14 mM magnesium acetate, 60 mM potassium acetate, 2 mM dithiothreitol)[60], and stored at −80° C. To make cell extract, cell pellets were thawed and suspended in 0.8 mL of S30 buffer per gram of wet cell mass and 1.4 mL of cell slurry was transferred into 1.5 mL microtubes. The cells were lysed using a Q125 Sonicator (Qsonica, Newtown, Conn.) with 3.175 mm diameter probe at a 20 kHz frequency and 50% amplitude for three cycles of 45s ON/59s OFF. To minimize heat damage during sonication, samples were placed in an ice-water bath. For each 1.4 mL sample, the input energy was ~844 Joules and was monitored during sonication. Extract was then centrifuged at 12,000×g at 4° C. for 10 min. For strain derivatives of C321.ΔA.759, a run-off reaction (37° C. at 250 rpm for 1 h) and second centrifugation (10,000×g at 4° C. for 10 min) were performed[20]. The supernatant was flash-frozen using liquid nitrogen and stored at −80° C. until use.

CFPS Reaction.

A modified PANOx-SP system was utilized for CFPS reactions testing incorporation of pAcF[2]. Briefly, a 15 µL CFPS reaction in a 1.5 mL microtube was prepared by mixing the following components: 1.2 mM ATP; 0.85 mM each of GTP, UTP, and CTP; 34 µg/mL folinic acid; 170 µg/mL of E. coli tRNA mixture; 13.3 µg/mL plasmid; 16 µg/mL T7 RNA polymerase; 2 mM for each of the 20 standard amino acids; 0.33 mM nicotinamide adenine dinucleotide (NAD); 0.27 mM coenzyme-A (CoA); 1.5 mM spermidine; 1 mM putrescine; 4 mM sodium oxalate; 130 mM potassium glutamate; 10 mM ammonium glutamate; 12 mM magnesium glutamate; 57 mM HEPES, pH 7.2; 33 mM phosphoenolpyruvate (PEP), and 27% v/v of cell extract. For NSAA incorporation, 2 mM pAcF, 1.0 mg/mL pAcFRS, and 10 µg/mL of o-tz-tRNA linear DNA were supplemented to cell-free reactions. o-tRNA linear DNA was amplified from pY71-T7-tz-o-tRNA plasmid as described previously[29] and transcribed during the cell-free reaction. Furthermore, the o-tRNA was expressed in the source strain prior to extract preparation. Each CFPS reaction was incubated for 20 h at 30° C. unless noted otherwise. *E. coli* total tRNA mixture (from strain MRE600) and phosphoenolpyruvate was purchased from Roche Applied Science (Indianapolis, Ind.). ATP, GTP, CTP, UTP, 20 amino acids and other materials were purchased from Sigma (St. Louis, Mo.) without further purification. T7RNAP and pAcFRS was purified in house.

Quantification of Active sfGFP.

CFPS reactions were diluted 1:25 in nanopure water and active full-length sfGFP protein yields were quantified by measuring fluorescence using a Synergy 2 plate reader (BioTek, Winooski, Vt.) with excitation at 485 nm, emission at 528 nm, and cut-off at 510 nm in 96-well half area black plates (Costar 3694; Corning, Corning, N.Y.). sfGFP fluorescence units were converted to concentration using a standard curve established with $^{14}$C-Leu quantified sfGFP as described previously[29].

Quantification of Active mRFP.

CFPS reactions were diluted 1:25 in nanopure water and active mRFP yields were quantified by measuring fluorescence using a Synergy 2 plate reader (Biotek, Winooski, Vt.) with excitation at 503 nm and emission at 607 nm in 96-well half area black plates (Costar 3694; Corning, Corning, N.Y.).

Detection of his-Tagged T7RNAP by Western Blot.

To visualize polymerase overexpression in vivo, cell samples were collected during harvest. Pre-induction cell samples were derived from 1 mL of culture at $OD_{600}$ of 0.6, harvest samples were derived from 200 µL of culture at $OD_{600}$ of 3.0. To prepare samples for gel electrophoresis, cells were pelleted and resuspended in 200 µL of nuclease-free water. 100 µL of this suspension was mixed with 34 µL of 4× NuPAGE® LDS Sample Buffer (Thermo Fisher Scientific, Inc., Waltham, Mass.) and boiled for 10 minutes. Following the boil, samples were spun at >13,500×g. Samples derived from lysates were prepared by diluting 1 µL of extract in 8 µL of nuclease-free water and boiling for 10 minutes with 3 µL of 4× NuPAGE® LDS Sample Buffer. 12 µL of each samples was loaded into 12% Bis-Tris NuPAGE® gel (Thermo Fisher Scientific, Inc., Waltham, Mass.) and run at 130 V for 90 min using 1×MOPS running buffer (diluted from 20×MOPS SDS Running Buffer, Thermo Fisher Scientific, Inc., Waltham, Mass.). For reference, SeeBlue® Plus2 Pre-Stained Protein Standard (Thermo Fisher Scientific, Inc., Waltham, Mass.) was loaded into wells flanking the samples. Following electrophoresis, gels were washed in nanopure water. Proteins were transferred to Immun-Blot® PVDF membrane (Bio-rad, Hercules, Calif.) using a semi-dry protocol in 20% methanol/80% 1× MOPS. Transfer proceeded at 80 mA per gel for 55 min using a Trans-Blot® SD Semi-Dry Transfer Cell (Bio-rad, Hercules, Calif.). Blots were blocked overnight in 5% (m/v) fat-free dry milk at 4° C. Primary antibody (Sigma, Cat. #H1029, St. Louis, Mo.) was diluted 3,000× in PBS and applied to blots for 2 hrs. Secondary antibody (Bio-rad, Hercules, Calif.) was diluted 10,000× in PBS-T and applied to blots for 1 hr. Finally, His-tagged proteins were visualized using the Immun-Blot® Opti-4CN™ Colorimetric kit (Bio-rad, Hercules, Calif.).

Knockout of ompT Locus.

In order to use kanamycin resistance to select for successful knockout of the ompT locus in C321.ΔA.759.T7, the kanR cassette first employed to select for integration of the T7RNAP insert needed to be removed from the genome. This DNA was physically looped out of the genome using selected oligos for MAGE. Cultures were grown in LB media at 32° C. and 250 rpm throughout 8 MAGE cycling steps. Replica plating was used to identify colonies that regained sensitivity to kanamycin, and colony PCR using the protocol described above confirmed that the kanamycin resistance cassette DNA was no longer present in the genome. The kanamycin resistant cassette from pKD4 was then amplified with primers containing up- and downstream homology to the genomic region targeted for deletion in their 5' tails. The knockout construct was given flanking homology such that coordinates 580,650-592,260 in the genome of C321.ΔA.759.T7 would be replaced by the resistance cassette. λHR followed by colony PCR detection of the knockout were performed as described above to yield C321.ΔA.759.T7.ΔompT.

Generation and Verification of OmpT-Resistant T7RNAP-Expressing Strains.

Nucleotide changes designed to introduce mutations of K183 to glycine/leucine and K190 to alanine were installed into C321.ΔA.759.T7's genomic copy of the N-terminally 6His-tagged 1 gene via MAGE using selected oligos. Cultures were grown in selective LB media at 32° C. and 250 rpm throughout 6 MAGE cycling steps as previously described. Putative mutant colonies were picked and cultured as described above prior to screening for the desired mutation. Multiplex allele-specific colony (MASC) PCR was performed to verify mutations[59] using wild-type forward or mutant forward primers and reverse primers. Wild-type and mutant forward primers were identical except at the 3'-ends of the oligonucleotides which featured allele-specific sequence such that stable annealing of the end of the primer should only be possible when paired with the corresponding genomic allele. In this way the mutant allele could be amplified using the mutant forward and reverse primer set but not amplified by the wild-type forward and reverse primer set, and vice versa. The reverse primers were used for detection of both wild-type and mutant alleles.

sfGFP Timecourse.

CFPS reactions were assembled in the wells of a half-area black 96-well plate (Costar 3694; Corning, Corning, N.Y.) as described above. To minimize the effects of evaporation, the volumes of all components were doubled to scale total reaction volume up to 30 µL. To maintain humidity and preserve reaction volume throughout the CFPS reaction, all unused wells were filled with 100 µL nanopure water and the plate was covered with an evaporation lid and finally sealed with Parafilm M® (Bemis, Neenah, Wis.). Reactions were run in a Synergy H1 plate reader (BioTek, Winooski, Vt.) at 30° C., with fluorescence measurements of each experimental well taken every 5 minutes for 20 hrs. Measurements were taken with excitation at 485 nm, emission at 528 nm, and cut-off at 510 nm.

mRNA Radioactive Quantitation.

Radioactive $^3$H-UTP was added into 15 µL CFPS reactions. At each timepoint analyzed, two reactions per condition were sacrificed by flash freezing in liquid nitrogen and stored at −20° C. until measured. To obtain an accurate 0 timepoint, all proteins in each reaction were precipitated with TCA prior to template plasmid addition. Yields were quantified by determining $^3$H-UTP incorporation into mRNA transcripts. Radioactivity of samples was measured using liquid scintillation counting (MicroBeta2, PerkinElmer, Waltham, Mass.).

Autoradiogram Analysis.

For autoradiogram analysis, samples were prepared as described above from 4 µL of each reaction and loaded on 12% Bis-Tris NuPAGE® gel (Thermo Fisher Scientific, Inc., Waltham, Mass.). The gel was soaked in Gel Drying solution (Bio-Rad, Hercules, Calif.) for 30 min, fixed with cellophane films, dried overnight in GelAir Dryer (Bio-Rad, Hercules, Calif.), and exposed for 3 days on Storage Phosphor Screen (GE Healthcare Biosciences, Pittsburgh, Pa.). Autoradiograms were scanned using Typhoon FLA 7000 Imager (GE Healthcare Biosciences, Pittsburgh, Pa.).

ELP Radioactive Quantitation.

Radioactive $^{14}$C-Glycine was added into 15 μL CFPS reactions. After incubation, yields were quantified by determining radioactive $^{14}$C-Gly incorporation into trichloroacetic acid (TCA)-precipitated protein[60]. Radioactivity of TCA-precipitated samples was measured using liquid scintillation counting (MicroBeta2, PerkinElmer, Waltham, Mass.).

Locus DNA Sequencing.

To sequence the genomic T7RNAP inserts, the entire region was PCR amplified using selected end primers. Amplified linear insert DNA was submitted to the NUSeq Core facility along with forward primers spaced ~700 bp apart, and the sequence for each region was determined using traditional Sanger sequencing.

REFERENCES

1. Carlson, E. D., Gan, R., Hodgman, C. E. & Jewett, M. C. Cell-free protein synthesis: applications come of age. Biotechnology advances 30, 1185-1194, doi:10.1016/j.biotechadv.2011.09.016 (2012).
2. Jewett, M. C. & Swartz, J. R. Mimicking the *Escherichia coli* cytoplasmic environment activates long-lived and efficient cell-free protein synthesis. Biotechnology and bioengineering 86, 19-26, doi:10.1002/bit.20026 (2004).
3. Caschera, F. & Noireaux, V. Synthesis of 2.3 mg/ml of protein with an all *Escherichia coli* cell-free transcription-translation system. Biochimie 99, 162-168, doi:10.1016/j.biochi.2013.11.025 (2014).
4. Zawada, J. F. et al. Microscale to manufacturing scale-up of cell-free cytokine production—a new approach for shortening protein production development timelines. Biotechnology and bioengineering 108, 1570-1578, doi:10.1002/bit.23103 (2011).
5. Hong, S. H. et al. Improving Cell-Free Protein Synthesis through Genome Engineering of *Escherichia coli* Lacking Release Factor 1. Chembiochem: a European journal of chemical biology, doi:10.1002/cbic.201402708 (2015).
6. Yang, W. C. et al. Cell-free production of transducible transcription factors for nuclear reprogramming. Biotechnology and bioengineering 104, 1047-1058, doi:10.1002/bit.22517 (2009).
7. Chappell, J., Jensen, K. & Freemont, P. S. Validation of an entirely in vitro approach for rapid prototyping of DNA regulatory elements for synthetic biology. Nucleic acids research 41, 3471-3481, doi:10.1093/nar/gkt052 (2013).
8. Takahashi, M. K. et al. Characterizing and prototyping genetic networks with cell-free transcription-translation reactions. Methods 86, 60-72, doi:10.1016/j.ymeth.2015.05.020 (2015).
9. Karim, A. S. & Jewett, M. C. A cell-free framework for rapid biosynthetic pathway prototyping and enzyme discovery. Metabolic engineering 36, 116-126, doi:10.1016/j.ymben.2016.03.002 (2016).
10. Watanabe, M. et al. Cell-free protein synthesis for structure determination by X-ray crystallography. Methods in molecular biology 607, 149-160, doi:10.1007/978-1-60327-331-2_13 (2010).
11. Martemyanov, K. A., Shirokov, V. A., Kumasov, O. V., Gudkov, A. T. & Spirin, A. S. Cell-free production of biologically active polypeptides: application to the synthesis of antibacterial peptide cecropin. Protein expression and purification 21, 456-461, doi:10.1006/prep.2001.1400 (2001).
12. Renesto, P. & Raoult, D. From genes to proteins: in vitro expression of rickettsial proteins. Annals of the New York Academy of Sciences 990, 642-652 (2003).
13. Xu, Z., Chen, H., Yin, X., Xu, N. & Cen, P. High-level expression of soluble human beta-defensin-2 fused with green fluorescent protein in *Escherichia coli* cell-free system. Applied biochemistry and biotechnology 127, 53-62 (2005).
14. Sullivan, C. J. et al. A cell-free expression and purification process for rapid production of protein biologics. Biotechnology journal 11, 238-248, doi:10.1002/biot.201500214 (2016).
15. Li, J. et al. Cell-free protein synthesis enables high yielding synthesis of an active multicopper oxidase. Biotechnology journal 11, 212-218, doi:10.1002/biot.201500030 (2016).
16. Heinzelman, P., Schoborg, J. A. & Jewett, M. C. pH responsive granulocyte colony-stimulating factor variants with implications for treating Alzheimer's disease and other central nervous system disorders. Protein engineering, design & selection: PEDS 28, 481-489, doi:10.1093/protein/gzv022 (2015).
17. Shin, J. & Noireaux, V. Efficient cell-free expression with the endogenous *E. Coli* RNA polymerase and sigma factor 70. Journal of biological engineering 4, 8, doi:10.1186/1754-1611-4-8 (2010).
18. Shin, J. & Noireaux, V. An *E. coli* cell-free expression toolbox: application to synthetic gene circuits and artificial cells. ACS synthetic biology 1, 29-41, doi:10.1021/sb200016s (2012).
19. Studier, F. W. & Moffatt, B. A. Use of bacteriophage T7 RNA polymerase to direct selective high-level expression of cloned genes. Journal of molecular biology 189, 113-130 (1986).
20. Kwon, Y. C. & Jewett, M. C. High-throughput preparation methods of crude extract for robust cell-free protein synthesis. Scientific reports 5, 8663, doi:10.1038/srep08663 (2015).
21. Des Soye, B. J., Patel, J. R., Isaacs, F. J. & Jewett, M. C. Repurposing the translation apparatus for synthetic biology. Current opinion in chemical biology 28, 83-90, doi:10.1016/j.cbpa.2015.06.008 (2015).
22. Hong, S. H., Kwon, Y. C. & Jewett, M. C. Non-standard amino acid incorporation into proteins using *Escherichia coli* cell-free protein synthesis. Frontiers in chemistry 2, 34, doi:10.3389/fchem.2014.00034 (2014).
23. Dumas, A. e., Lercher, L., Spicer, C. D. & Davis, B. G. Designing logical codon reassignment—Expanding the chemistry in biology. Chemical Science 6, 50-69 (2014).
24. Liu, C. C. & Schultz, P. G. Adding new chemistries to the genetic code. Annual review of biochemistry 79, 413-444, doi:10.1146/annurev.biochem.052308.105824 (2010).
25. Santoro, S. W., Wang, L., Herberich, B., King, D. S. & Schultz, P. G. An efficient system for the evolution of aminoacyl-tRNA synthetase specificity. Nature biotechnology 20, 1044-1048, doi:10.1038/nbt742 (2002).
26. Nehring, S., Budisa, N. & Wiltschi, B. Performance analysis of orthogonal pairs designed for an expanded eukaryotic genetic code. PloS one 7, e31992, doi:10.1371/journal.pone.0031992 (2012).

27. Bundy, B. C. & Swartz, J. R. Site-specific incorporation of p-propargyloxyphenylalanine in a cell-free environment for direct protein-protein click conjugation. Bioconjugate chemistry 21, 255-263, doi:10.1021/bc9002844 (2010).
28. Young, T. S. & Schultz, P. G. Beyond the canonical 20 amino acids: expanding the genetic lexicon. The Journal of biological chemistry 285, 11039-11044, doi:10.1074/jbc.R109.091306 (2010).
29. Hong, S. H. et al. Cell-free protein synthesis from a release factor 1 deficient *Escherichia coli* activates efficient and multiple site-specific nonstandard amino acid incorporation. ACS synthetic biology 3, 398-409, doi:10.1021/sb400140t (2014).
30. Lajoie, M. J. et al. Genomically recoded organisms expand biological functions. Science 342, 357-360, doi:10.1126/science.1241459 (2013).
31. Datsenko, K. A. & Wanner, B. L. One-step inactivation of chromosomal genes in *Escherichia coli* K-12 using PCR products. Proceedings of the National Academy of Sciences of the United States of America 97, 6640-6645, doi:10.1073/pnas.120163297 (2000).
32. Mosberg, J. A., Lajoie, M. J. & Church, G. M. Lambda red recombineering in *Escherichia coli* occurs through a fully single-stranded intermediate. Genetics 186, 791-799, doi:10.1534/genetics.110.120782 (2010).
33. Wang, H. H. et al. Programming cells by multiplex genome engineering and accelerated evolution. Nature 460, 894-898, doi:10.1038/nature08187 (2009).
34. Zawada, J. & Swartz, J. Effects of growth rate on cell extract performance in cell-free protein synthesis. Biotechnology and bioengineering 94, 618-624, doi:10.1002/bit.20831 (2006).
35. Bremer, H. & Dennis, P. *Escherichia coli* and *Salmonella*: Cellular and Molecular Biology. 2 edn, Vol. 1 1553-1569 (ASM Press, 1996).
36. Stefano, J. E. & Gralla, J. Lac UV5 transcription in vitro. Rate limitation subsequent to formation of an RNA polymerase-DNA complex. Biochemistry 18, 1063-1067 (1979).
37. de Boer, H. A., Comstock, L. J. & Vasser, M. The tac promoter: a functional hybrid derived from the tip and lac promoters. Proceedings of the National Academy of Sciences of the United States of America 80, 21-25 (1983).
38. Inouye, S. & Inouye, M. Up-promoter mutations in the lpp gene of *Escherichia coli*. Nucleic acids research 13, 3101-3110 (1985).
39. Espah Borujeni, A., Channarasappa, A. S. & Salis, H. M. Translation rate is controlled by coupled trade-offs between site accessibility, selective RNA unfolding and sliding at upstream standby sites. Nucleic acids research 42, 2646-2659, doi:10.1093/nar/gkt1139 (2014).
40. Salis, H. M., Mirsky, E. A. & Voigt, C. A. Automated design of synthetic ribosome binding sites to control protein expression. Nature biotechnology 27, 946-950, doi:10.1038/nbt.1568 (2009).
41. Effinger, T. & Ehricht, R. Single-step purification of T7 RNA polymerase with a 6-histidine tag. BioTechniques 24, 718-720 (1998).
42. Bryant, J. A., Sellars, L. E., Busby, S. J. & Lee, D. J. Chromosome position effects on gene expression in *Escherichia coli* K-12. Nucleic acids research 42, 11383-11392, doi:10.1093/nar/gku828 (2014).
43. Grodberg, J. & Dunn, J. J. ompT encodes the *Escherichia coli* outer membrane protease that cleaves T7 RNA polymerase during purification. Journal of bacteriology 170, 1245-1253 (1988).
44. Muller, D. K., Martin, C. T. & Coleman, J. E. Processivity of proteolytically modified forms of T7 RNA polymerase. Biochemistry 27, 5763-5771 (1988).
45. Ikeda, R. A. & Richardson, C. C. Enzymatic properties of a proteolytically nicked RNA polymerase of bacteriophage T7. The Journal of biological chemistry 262, 3790-3799 (1987).
46. Ikeda, R. A. & Richardson, C. C. Interactions of a proteolytically nicked RNA polymerase of bacteriophage T7 with its promoter. The Journal of biological chemistry 262, 3800-3808 (1987).
47. Gottesman, S. Proteases and their targets in *Escherichia coli*. Annual review of genetics 30, 465-506, doi:10.1146/annurev.genet.30.1.465 (1996).
48. Hwang, B. Y. et al. Substrate specificity of the *Escherichia coli* outer membrane protease OmpP. Journal of bacteriology 189, 522-530, doi:10.1128/JB.01493-06 (2007).
49. Tunitskaya, V. L. & Kochetkov, S. N. Structural-functional analysis of bacteriophage T7 RNA polymerase. Biochemistry. Biokhimiia 67, 1124-1135 (2002).
50. Petrov, A. S. et al. RNA-magnesium-protein interactions in large ribosomal subunit. The journal of physical chemistry. B 116, 8113-8120, doi:10.1021/jp304723w (2012).
51. Sousa, R. in Encyclopedia of Biological Chemistry Vol. 4 (eds William J Lennarz & M. Daniel Lane) (Elsevier, 2004).
52. Young, T. S., Ahmad, I., Yin, J. A. & Schultz, P. G. An enhanced system for unnatural amino acid mutagenesis in *E. coli*. Journal of molecular biology 395, 361-374, doi:10.1016/j.jmb.2009.10.030 (2010).
53. Wang, L., Zhang, Z., Brock, A. & Schultz, P. G. Addition of the keto functional group to the genetic code of *Escherichia coli*. Proceedings of the National Academy of Sciences of the United States of America 100, 56-61, doi:10.1073/pnas.0234824100 (2003).
54. Raucher, D. & Ryu, J. S. Cell-penetrating peptides: strategies for anticancer treatment. Trends in molecular medicine 21, 560-570, doi:10.1016/j.molmed.2015.06.005 (2015).
55. Catherine, C. et al. Engineering Thermal Properties of Elastin-like Polypeptides by Incorporation of Unnatural Amino Acids in a Cell-free Protein Synthesis System. Biotechnology and Bioprocess Engineering 20, 417-422, doi:10.1007/s12257-015-0190-1 (2015).
56. Wu, I. L. et al. Multiple site-selective insertions of noncanonical amino acids into sequence-repetitive polypeptides. Chembiochem: a European journal of chemical biology 14, 968-978, doi:10.1002/cbic.201300069 (2013).
57. Chen, Y. J. et al. Characterization of 582 natural and synthetic terminators and quantification of their design constraints. Nature methods 10, 659-664, doi:10.1038/nmeth.2515 (2013).
58. Horton, R. M. PCR-mediated recombination and mutagenesis. SOEing together tailor-made genes. Molecular biotechnology 3, 93-99, doi:10.1007/BF02789105 (1995).
59. Wang, H. H. & Church, G. M. Multiplexed genome engineering and genotyping methods applications for synthetic biology and metabolic engineering. Methods in enzymology 498, 409-426, doi:10.1016/B978-0-12-385120-8.00018-8 (2011).
60. Swartz, J. R., Jewett, M. C. & Woodrow, K. A. Cell-free protein synthesis with prokaryotic combined transcription-translation. Methods in molecular biology (Clifton, N.J.) 267, 169-182, doi:10.1385/1-59259-774-2:169 (2004).
61. Lederberg, J. & Lederberg, E. M. Replica plating and indirect selection of bacterial mutants. Journal of bacteriology 63, 399-406 (1952).
62. Davanloo, P., Rosenberg, A. H., Dunn, J. J. & Studier, F. W. Cloning and expression of the gene for bacteriophage T7 RNA polymerase. Proceedings of the National Academy of Sciences of the United States of America 81, 2035-2039 (1984).
63. Fritz, B. R., Jamil, O. K. & Jewett, M. C. Implications of macromolecular crowding and reducing conditions for in vitro ribosome construction. Nucleic acids research 43, 4774-4784, doi:10.1093/nar/gkv329 (2015).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A genomically recoded organism lacking release factor 1 (RF1) and engineered to express a heterologous RNA polymerase, wherein the heterologous RNA polymerase is a variant bacteriophage T7 RNA polymerase that includes a substitution that replaces a basic amino acid selected from K172 and R173 with a non-basic amino acid and/or that includes a substitution that replaces a basic amino acid selected from K179 and K180 with a non-basic amino acid.

2. The organism of claim 1, wherein the organism is a strain of *E. coli*.

3. The organism of claim 1, wherein the heterologous RNA polymerase is expressed via a promoter selected from ptac1 and lpp5.

4. The organism of claim 1, wherein the organism is derived from a C321 strain of *E. coli*.

5. The organism of claim 1, wherein the organism further comprises an orthogonal translation system component that is expressed off a plasmid or that is expressed from the genome of the organism.

6. The organism of claim 5, wherein the orthogonal translation system component is an orthogonal tRNA or an aminoacyl tRNA synthetase.

7. The organism of claim 1, wherein the organism comprises one or more additional genomic modifications that enhance protein synthesis yields and incorporation of multiple identical unnatural amino acids when the organism is utilized to prepare a cell-free extract for protein synthesis.

8. The organism of claim 1, wherein the organism expresses one or more positive effector genes that augment the function of polypeptide synthesis via a plasmid or genomic integration.

9. The organism of claim 8, wherein the positive effector gene encodes a chaperone protein.

10. The organism of claim 8, wherein the positive effector gene is DsbC.

11. A platform for preparing a sequence defined biopolymer or protein in vitro, the platform comprising a cellular extract from the organism of claim 1.

12. The platform of claim 7, wherein the defined biopolymer or protein synthesized in the platform has unnatural amino acids.

13. The platform of claim 7, wherein the defined biopolymer or protein synthesized in the platform has at least 10 unnatural amino acids.

14. A method for performing cell-free protein synthesis of a target protein comprising one or more unnatural amino acids, the method comprising expressing a mRNA encoding the target protein in the platform of claim 11.

15. A genomically recoded organism lacking release factor 1 (RF1) and engineered to express a heterologous RNA polymerase, wherein the heterologous RNA polymerase is inserted at the asl locus of the organism's genome.

16. The organism of claim 15, wherein the organism is a strain of *E. coli*.

17. The organism of claim 15, wherein the heterologous RNA polymerase is expressed via a promoter selected from ptac1 and lpp5.

18. The organism of claim 15, wherein the organism is derived from a C321 strain of *E. coli*.

19. A platform for preparing a sequence defined biopolymer or protein in vitro, the platform comprising a cellular extract from the organism of claim 15.

20. A method for performing cell-free protein synthesis of a target protein comprising one or more unnatural amino acids, the method comprising expressing a mRNA encoding the target protein in the platform of claim 19.

* * * * *

UNITED STATES PATENT AND TRADEMARK OFFICE
CERTIFICATE OF CORRECTION

PATENT NO.        : 10,465,221 B2
APPLICATION NO.   : 15/651484
DATED             : November 5, 2019
INVENTOR(S)       : Jewett et al.

It is certified that error appears in the above-identified patent and that said Letters Patent is hereby corrected as shown below:

In the Claims

Column 61, Line 39, "ptac1" should be --ptacl--.

Column 62, Line 48, "ptac1" should be --ptacl--.

Signed and Sealed this
Third Day of August, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 9

<210> SEQ ID NO 1
<211> LENGTH: 883
<212> TYPE: PRT
<213> ORGANISM: Bacteriophage T7

<400> SEQUENCE: 1

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220
```

-continued

```
Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
            245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His Gly Leu Ser Tyr
            515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
                580                 585                 590

Glu Val Val Thr Val Thr Asp Glu Asn Thr Gly Glu Ile Ser Glu Lys
                595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Tyr Gly
625                 630                 635                 640
```

```
Ser Lys Glu Phe Gly Phe Arg Gln Gln Val Leu Glu Asp Thr Ile Gln
                645                 650                 655
Pro Ala Ile Asp Ser Gly Lys Gly Leu Met Phe Thr Gln Pro Asn Gln
            660                 665                 670
Ala Ala Gly Tyr Met Ala Lys Leu Ile Trp Glu Ser Val Ser Val Thr
        675                 680                 685
Val Val Ala Ala Val Glu Ala Met Asn Trp Leu Lys Ser Ala Ala Lys
    690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
    770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
        835                 840                 845
Phe Ala Asp Gln Leu His Glu Ser Gln Leu Asp Lys Met Pro Ala Leu
    850                 855                 860
Pro Ala Lys Gly Asn Leu Asn Leu Arg Asp Ile Leu Glu Ser Asp Phe
865                 870                 875                 880
Ala Phe Ala

<210> SEQ ID NO 2
<211> LENGTH: 2877
<212> TYPE: DNA
<213> ORGANISM: Bacteriophage T7

<400> SEQUENCE: 2
tcgcgctgca ctggcgtaat gctgaccgga tggctatcgc taatggtctt acgctcaaca    60
ttgataagca acttgacgca atgttaatgg gctgatagtc ttatcttaca ggtcatctgc   120
gggtggcctg ataggtacg atttactaac tggaagaggc actaaatgaa cacgattaac   180
atcgctaaga acgacttctc tgacatcgaa ctggctgcta tcccgttcaa cactctggct   240
gaccattacg gtgagcgttt agctcgcgaa cagttggccc ttgagcatga gtcttacgag   300
atgggtgaag cacgcttccg caagatgttt gagcgtcaac ttaaagctgg tgaggttgcg   360
gataacgctg ccgccaagcc tctcatcact accctactcc ctaagatgat gcacgcatc   420 aacgactggt ttgaggaagt gaaagctaag cgcggcaagc cccgacagc cttccagttc   480 ctgcaagaaa tcaagccgga agccgtagcg tacatcacca ttaagaccac tctggcttgc   540
ctaaccagtg ctgacaatac aaccgttcag gctgtagcaa gcgcaatcgg tcgggccatt   600
gaggacgagg ctcgcttcgg tcgtatccgt gaccttgaag ctaagcactt caagaaaaac   660
gttgaggaac aactcaacaa gcgcgtaggg cacgtctaca agaaagcatt tatgcaagtt   720
```

```
gtcgaggctg acatgctctc taagggtcta ctcggtggcg aggcgtggtc ttcgtggcat    780
aaggaagact ctattcatgt aggagtacgc tgcatcgaga tgctcattga gtcaaccgga    840
atggttagct tacaccgcca aaatgctggc gtagtaggtc aagactctga gactatcgaa    900
ctcgcacctg aatacgctga ggctatcgca acccgtgcag gtgcgctggc tggcatctct    960
ccgatgttcc aaccttgcgt agttcctcct aagccgtgga ctggcattac tggtggtggc   1020
tattgggcta acggtcgtcg tcctctggcg ctggtgcgta ctcacagtaa gaaagcactg   1080
atgcgctacg aagacgttta catgcctgag gtgtacaaag cgattaacat tgcgcaaaac   1140
accgcatgga aaatcaacaa gaaagtccta gcggtcgcca acgtaatcac caagtggaag   1200
cattgtccgg tcgaggacat ccctgcgatt gagcgtgaag aactcccgat gaaaccggaa   1260
gacatcgaca tgaatcctga ggctctcacc gcgtggaaac gtgctgccgc tgctgtgtac   1320
cgcaaggaca gggctcgcaa gtctcgccgt atcagccttg agttcatgct tgagcaagcc   1380
aataagtttg ctaaccataa ggccatctgg ttcccttaca acatggactg gcgcggtcgt   1440
gtttacgccg tgtcaatgtt caacccgcaa ggtaacgata tgaccaaagg actgcttacg   1500
ctggcgaaag gtaaaccaat cggtaaggaa ggttactact ggctgaaaat ccacggtgca   1560
aactgtgcgg tgtcgataa ggttccgttc cctgagcgca tcaagttcat tgaggaaaac   1620
cacgagaaca tcatggcttg cgctaagtct ccactggaga acacttggtg ggctgagcaa   1680
gattctccgt tctgcttcct tgcgttctgc tttgagtacg ctggggtaca gcaccacggc   1740
ctgagctata actgctccct tccgctggcg tttgacgggt cttgctctgg catccagcac   1800
ttctccgcga tgctccgaga tgaggtaggt ggtcgcgcgg ttaacttgct tcctagtgag   1860
accgttcagg acatctacgg gattgttgct aagaaagtca cgagattct acaagcagac   1920 gcaatcaatg ggaccgataa cgaagtagtt accgtgaccg atgagaacac tggtgaaatc   1980
tctgagaaag tcaagctggg cactaaggca ctggctggtc aatggctggc tcacggtgtt   2040
actcgcagtg tgactaagcg ttcagtcatg acgctggctt acgggtccaa agagttcggc   2100
ttccgtcaac aagtgctgga agataccatt cagccagcta ttgattccgg caagggtccg   2160
atgttcactc agccgaatca ggctgctgga tacatggcta agctgatttg ggaatctgtg   2220
agcgtgacgg tggtagctgc ggttgaagca atgaactggc ttaagtctgc tgctaagctg   2280
ctggctgctg aggtcaaaga taagaagact ggagagattc ttcgcaagcg ttgcgctgtg   2340
cattgggtaa ctcctgatgg tttccctgtg tggcaggaat acaagaagcc tattcagacg   2400
cgcttgaacc tgatgttcct cggtcagttc cgcttacagc ctaccattaa caccaacaaa   2460
gatagcgaga ttgatgcaca caaacaggag tctggtatcg ctcctaactt tgtacacagc   2520
caagacggta gccaccttcg taagactgta gtgtgggcac acgagaagta cggaatcgaa   2580
tcttttgcac tgattcacga ctccttcggt accattccgg ctgacgctgc gaacctgttc   2640
aaagcagtgc gcgaaactat ggttgacaca tatgagtctt gtgatgtact ggctgatttc   2700
tacgaccagt tcgctgacca gttgcacgag tctcaattgg acaaaatgcc agcacttccg   2760
gctaaaggta acttgaacct ccgtgacatc ttagagtcgg acttcgcgtt cgcgtaacgc   2820
caaatcaata cgactcacta tagggacaaa aactcaaggt cattcgcaag agtggcc     2877
```

<210> SEQ ID NO 3
<211> LENGTH: 18
<212> TYPE: DNA
<213> ORGANISM: Bacteriophage T7

<400> SEQUENCE: 3
taatacgact cactatag                                                 18

<210> SEQ ID NO 4
<211> LENGTH: 884
<212> TYPE: PRT
<213> ORGANISM: Bacteriophage T3

<400> SEQUENCE: 4

Met Asn Ile Ile Glu Asn Ile Glu Lys Asn Asp Phe Ser Glu Ile Glu
1               5                   10                  15

Leu Ala Ala Ile Pro Phe Asn Thr Leu Ala Asp His Tyr Gly Ser Ala
            20                  25                  30

Leu Ala Lys Glu Gln Leu Ala Leu Glu His Glu Ser Tyr Glu Leu Gly
        35                  40                  45

Glu Arg Arg Phe Leu Lys Met Leu Glu Arg Gln Ala Lys Ala Gly Glu
    50                  55                  60

Ile Ala Asp Asn Ala Ala Ala Lys Pro Leu Leu Ala Thr Leu Leu Pro
65                  70                  75                  80

Lys Leu Thr Thr Arg Ile Val Glu Trp Leu Glu Glu Tyr Ala Ser Lys
                85                  90                  95

Lys Gly Arg Lys Pro Ser Ala Tyr Ala Pro Leu Gln Leu Leu Lys Pro
            100                 105                 110

Glu Ala Ser Ala Phe Ile Thr Leu Lys Val Ile Leu Ala Ser Leu Thr
        115                 120                 125

Ser Thr Asn Met Thr Thr Ile Gln Ala Ala Gly Met Leu Gly Lys
    130                 135                 140

Ala Ile Glu Asp Glu Ala Arg Phe Gly Arg Ile Arg Asp Leu Glu Ala
145                 150                 155                 160

Lys His Phe Lys Lys His Val Glu Glu Gln Leu Asn Lys Arg His Gly
                165                 170                 175

Gln Val Tyr Lys Lys Ala Phe Met Gln Val Val Glu Ala Asp Met Ile
            180                 185                 190

Gly Arg Gly Leu Leu Gly Gly Glu Ala Trp Ser Ser Trp Asp Lys Glu
        195                 200                 205

Thr Thr Met His Val Gly Ile Arg Leu Ile Glu Met Leu Ile Glu Ser
    210                 215                 220

Thr Gly Leu Val Glu Leu Gln Arg His Asn Ala Gly Asn Ala Gly Ser
225                 230                 235                 240

Asp His Glu Ala Leu Gln Leu Ala Gln Glu Tyr Val Asp Val Leu Ala
                245                 250                 255

Lys Arg Ala Gly Ala Leu Ala Gly Ile Ser Pro Met Phe Gln Pro Cys
            260                 265                 270

Val Val Pro Pro Lys Pro Trp Val Ala Ile Thr Gly Gly Gly Tyr Trp
        275                 280                 285

Ala Asn Gly Arg Arg Pro Leu Ala Leu Val Arg Thr His Ser Lys Lys
    290                 295                 300

Gly Leu Met Arg Tyr Glu Asp Val Tyr Met Pro Glu Val Tyr Lys Ala
305                 310                 315                 320

Val Asn Leu Ala Gln Asn Thr Ala Trp Lys Ile Asn Lys Lys Val Leu
                325                 330                 335

Ala Val Val Asn Glu Ile Val Asn Trp Lys Asn Cys Pro Val Ala Asp
            340                 345                 350

```
            Ile Pro Ser Leu Glu Arg Gln Glu Leu Pro Pro Lys Pro Asp Asp Ile
                    355                 360                 365

Asp Thr Asn Glu Ala Ala Leu Lys Glu Trp Lys Lys Ala Ala Ala Gly
                370                 375                 380

Ile Tyr Arg Leu Asp Lys Ala Arg Val Ser Arg Ile Ser Leu Glu
            385                 390                 395                 400

Phe Met Leu Glu Gln Ala Asn Lys Phe Ala Ser Lys Ala Ile Trp
                            405                 410                 415

Phe Pro Tyr Asn Met Asp Trp Arg Gly Arg Val Tyr Ala Val Pro Met
                        420                 425                 430

Phe Asn Pro Gln Gly Asn Asp Met Thr Lys Gly Leu Leu Thr Leu Ala
                    435                 440                 445

Lys Gly Lys Pro Ile Gly Glu Glu Gly Phe Tyr Trp Leu Lys Ile His
                450                 455                 460

Gly Ala Asn Cys Ala Gly Val Asp Lys Val Pro Phe Pro Glu Arg Ile
            465                 470                 475                 480

Ala Phe Ile Glu Lys His Val Asp Asp Ile Leu Ala Cys Ala Lys Asp
                            485                 490                 495

Pro Ile Asn Asn Thr Trp Trp Ala Glu Gln Asp Ser Pro Phe Cys Phe
                        500                 505                 510

Leu Ala Phe Cys Phe Glu Tyr Ala Gly Val Thr His His Gly Leu Ser
                    515                 520                 525

Tyr Asn Cys Ser Leu Pro Leu Ala Phe Asp Gly Ser Cys Ser Gly Ile
                530                 535                 540

Gln His Phe Ser Ala Met Leu Arg Asp Glu Val Gly Gly Arg Ala Val
            545                 550                 555                 560

Asn Leu Leu Pro Ser Glu Thr Val Gln Asp Ile Tyr Gly Ile Val Ala
                            565                 570                 575

Gln Lys Val Asn Glu Ile Leu Lys Gln Asp Ala Ile Asn Gly Thr Pro
                        580                 585                 590

Asn Glu Met Ile Thr Val Thr Asp Lys Asp Thr Gly Glu Ile Ser Glu
                    595                 600                 605

Lys Leu Lys Leu Gly Thr Ser Thr Leu Ala Gln Gln Trp Leu Ala Tyr
                610                 615                 620

Gly Val Thr Arg Ser Val Thr Lys Arg Ser Val Met Thr Leu Ala Tyr
            625                 630                 635                 640

Gly Ser Lys Glu Phe Gly Phe Arg Gln Gln Val Leu Asp Asp Thr Ile
                            645                 650                 655

Gln Pro Ala Ile Asp Ser Gly Lys Gly Leu Met Phe Thr Gln Pro Asn
                        660                 665                 670

Gln Ala Ala Gly Tyr Met Ala Lys Leu Ile Trp Asp Ala Val Ser Val
                    675                 680                 685

Thr Val Val Ala Ala Val Glu Ala Met Asn Trp Leu Lys Ser Ala Ala
                690                 695                 700

Lys Leu Leu Ala Ala Glu Val Lys Asp Lys Thr Lys Glu Ile Leu
            705                 710                 715                 720

Arg His Arg Cys Ala Val His Trp Thr Thr Pro Asp Gly Phe Pro Val
                            725                 730                 735

Trp Gln Glu Tyr Arg Lys Pro Leu Gln Lys Arg Leu Asp Met Ile Phe
                        740                 745                 750

Leu Gly Gln Phe Arg Leu Gln Pro Thr Ile Asn Thr Leu Lys Asp Ser
                    755                 760                 765
```

Gly Ile Asp Ala His Lys Gln Glu Ser Gly Ile Ala Pro Asn Phe Val
770             775                 780

His Ser Gln Asp Gly Ser His Leu Arg Met Thr Val Val Tyr Ala His
785             790                 795                 800

Glu Lys Tyr Gly Ile Glu Ser Phe Ala Leu Ile His Asp Ser Phe Gly
                805                 810                 815

Thr Ile Pro Ala Asp Ala Gly Lys Leu Phe Lys Ala Val Arg Glu Thr
            820                 825                 830

Met Val Ile Thr Tyr Glu Asn Asn Asp Val Leu Ala Asp Phe Tyr Ser
            835                 840                 845

Gln Phe Ala Asp Gln Leu His Glu Thr Gln Leu Asp Lys Met Pro Pro
850                 855                 860

Leu Pro Lys Lys Gly Asn Leu Asn Leu Gln Asp Ile Leu Lys Ser Asp
865                 870                 875                 880

Phe Ala Phe Ala

<210> SEQ ID NO 5
<211> LENGTH: 2896
<212> TYPE: DNA
<213> ORGANISM: Bacteriophage T3

<400> SEQUENCE: 5

```
gatgaggtgc gcattgtggg gcaaaccgtt acacatagac gcataccttg acaagcgtct      60
acaaggctga tagagtcttt tcttacaggt catcatgagg tggcctgaat aggaacgatt     120
tattcacaat gaggtaagca atgaacatca tcgaaaacat cgaaaagaat gacttctcag     180
aaatcgaact ggctgctatc ccgttcaaca cactggctga ccactacgga agcgccttgg     240
ctaaagagca gttggcttta gaacatgagt cttatgagct aggcgagcgc cgcttcctca     300
agatgcttga gcgtcaagcg aaagctggtg agattgcaga caacgcagcc gctaagccgt     360
tactcgctac gcttctccct aagttaacca cacgtatcgt cgagtggctc gaagagtacg     420
catcgaagaa aggccgcaag cctagcgcat acgcaccgct ccagttactc aagccggagg     480
cctccgcgtt tatcaccctg aaagttatcc ttgcgtcact aaccagtacg aacatgacaa     540
ccattcaggc cgctgctggt atgctgggga agccattga ggacgaggca cgatttgggc     600
gcatccgtga cctagaagcg aagcacttca gaagcacgt tgaggaacag cttaacaagc     660
gccacgggca agtctacaag aaagcattta tgcaggtggt cgaggccgat atgattggtc     720
gaggtctgct tggtggcgag gcgtggtcta gctgggataa agaaaccacg atgcacgtag     780
ggattcgcct gattgaaatg ctgattgaat ccacgggtct ggtggaatta cagcgccaca     840
acgcaggtaa cgcaggctct gaccatgagg cactgcaact ggcccaagag tacgtggacg     900
tattagcgaa gcgtgcaggc gctctggcgg gtatctctcc gatgttccag ccgtgtgtcg     960
taccgccgaa accttgggta gcaatcacag ggggcggcta ttgggctaac ggtcgcagac    1020
ctttggcact cgttcgcact cactctaaga agggcttgat gcgctacgaa gacgtttaca    1080
tgccagaagt ctacaaggct gtgaacctcg cgcaaaacac gcatggaaa atcaacaaga    1140
aagttcttgc tgttgtcaat gagattgtta actggaagaa ttgcccggta gcagacattc    1200
catcgctgga gcgccaagag ttaccgccta agcctgacga cattgacacc aacgaggcag    1260
cgctcaagga gtggaagaaa gccgctgctg gtatctatcg cttggacaag gcacgagtgt    1320
ctcgccgtat cagcttagag ttcatgctgg agcaggccaa caagttcgca agtaagaaag    1380
caatctggtt cccttacaac atggactggc gcggtcgtgt gtacgctgtg ccgatgttca    1440
```

```
acccgcaagg caacgacatg acgaaaggtc tgctgaccct tgctaaaggc aagccaatcg    1500
gtgaggaagg tttctactgg ctgaaaatcc acggtgcgaa ctgtgcgggt gttgataagg    1560
ttccattccc ggagcgcatc gcgttcattg agaagcacgt agacgacatt ctggcttgcg    1620
ctaaagaccc aatcaataac acttggtggg ctgagcagga ttcaccgttc tgtttcctcg    1680
cgttttgctt cgagtatgca ggcgttacgc accacggtct gagctacaat tgctctctgc    1740
cgctggcgtt cgacgggtct tgctctggta tccagcactt ctccgcgatg ctccgcgatg    1800
aggtaggcgg tcgtgcggtt aacctgctgc aagcgaaac cgtgcaggac atttacggca     1860
tcgttgcaca gaaagtaaac gagattctca acaggatgc aatcaacggc acgcctaacg     1920
agatgattac cgtgaccgac aaggacaccg gggaaatctc agagaagctc aaacttggaa    1980
cctcaacgct ggcgcaacag tggctggcat atggtgtaac ccgtagcgta actaaacgtt    2040
cggtcatgac gctggcttac ggttccaagg agttcggctt tcgtcaacag gtattggatg    2100
acaccattca gcctgcaatt gacagcggta agggcttgat gttcacccaa ccgaaccaag    2160
cggctggcta tatggctaag ctgatttggg atgcggtaag cgtgaccgta gttgcagcgg    2220
ttgaggcgat gaactggctc aaatctgccg ctaagctgct ggctgctgag gtcaaggaca    2280
agaagaccaa ggagattctg cgccaccgtt gcgcggttca ctggactacg ccggacggct    2340
tcccggtctg gcaggaatac cgcaagccac tccagaagcg tctcgatatg attttcttag    2400
ggcaattccg tctgcaaccg acgattaata ccctcaagga ttcaggcatt gacgcacaca    2460
agcaggagtc tggcatcgct cctaactttg ttcactcaca ggacggtagc cacctccgca    2520
tgacagtcgt ttatgctcac gagaagtatg gcattgagtc ctttgcgctc atccatgaca    2580
gctttgggac tatcccggca gacgctggta agctctttaa ggctgtgcgt gaaacgatgg    2640
ttatcaccta tgagaacaac gatgtgctgg cagacttcta ctctcagttt gccgaccagc    2700
tacacgagac ccaactggac aagatgcctc cgcttccgaa gaaaggaaac ctgaacctgc    2760 aagcacattct caagtctgac tttgcctttg cataacaagc acttagcatt aaccctcact    2820
aacgggagac tacttaaggt ctcccacttt aagacacttt aggtactaag agattaaatt    2880
tatgattaac attaag                                                   2896

<210> SEQ ID NO 6
<211> LENGTH: 18
<212> TYPE: DNA
<213> ORGANISM: Bacteriophage T3

<400> SEQUENCE: 6
aattaaccct cactaaag                                                    18

<210> SEQ ID NO 7
<211> LENGTH: 874
<212> TYPE: PRT
<213> ORGANISM: Bacteriophage SP6

<400> SEQUENCE: 7

Met Gln Asp Leu His Ala Ile Gln Leu Gln Leu Glu Glu Glu Met Phe
1               5                   10                  15

Asn Gly Gly Ile Arg Arg Phe Glu Ala Asp Gln Gln Arg Gln Ile Ala
            20                  25                  30

Ala Gly Ser Glu Ser Asp Thr Ala Trp Asn Arg Arg Leu Leu Ser Glu
        35                  40                  45

Leu Ile Ala Pro Met Ala Glu Gly Ile Gln Ala Tyr Lys Glu Glu Tyr
    50                  55                  60
```

```
Glu Gly Lys Lys Gly Arg Ala Pro Arg Ala Leu Ala Phe Leu Gln Cys
 65                  70                  75                  80

Val Glu Asn Glu Val Ala Ala Tyr Ile Thr Met Lys Val Val Met Asp
                 85                  90                  95

Met Leu Asn Thr Asp Ala Thr Leu Gln Ala Ile Ala Met Ser Val Ala
            100                 105                 110

Glu Arg Ile Glu Asp Gln Val Arg Phe Ser Lys Leu Glu Gly His Ala
        115                 120                 125

Ala Lys Tyr Phe Glu Lys Val Lys Lys Ser Leu Lys Ala Ser Arg Thr
    130                 135                 140

Lys Ser Tyr Arg His Ala His Asn Val Ala Val Ala Glu Lys Ser
145                 150                 155                 160

Val Ala Glu Lys Asp Ala Asp Phe Asp Arg Trp Glu Ala Trp Pro Lys
                165                 170                 175

Glu Thr Gln Leu Gln Ile Gly Thr Thr Leu Leu Glu Ile Leu Glu Gly
            180                 185                 190

Ser Val Phe Tyr Asn Gly Glu Pro Val Phe Met Arg Ala Met Arg Thr
        195                 200                 205

Tyr Gly Gly Lys Thr Ile Tyr Tyr Leu Gln Thr Ser Glu Ser Val Gly
    210                 215                 220

Gln Trp Ile Ser Ala Phe Lys Glu His Val Ala Gln Leu Ser Pro Ala
225                 230                 235                 240

Tyr Ala Pro Cys Val Ile Pro Pro Arg Pro Trp Arg Thr Pro Phe Asn
                245                 250                 255

Gly Gly Phe His Thr Glu Lys Val Ala Ser Arg Ile Arg Leu Val Lys
            260                 265                 270

Gly Asn Arg Glu His Val Arg Lys Leu Thr Gln Lys Gln Met Pro Lys
        275                 280                 285

Val Tyr Lys Ala Ile Asn Ala Leu Gln Asn Thr Gln Trp Gln Ile Asn
    290                 295                 300

Lys Asp Val Leu Ala Val Ile Glu Glu Val Ile Arg Leu Asp Leu Gly
305                 310                 315                 320

Tyr Gly Val Pro Ser Phe Lys Pro Leu Ile Asp Lys Glu Asn Lys Pro
                325                 330                 335

Ala Asn Pro Val Pro Val Glu Phe Gln His Leu Arg Gly Arg Glu Leu
            340                 345                 350

Lys Glu Met Leu Ser Pro Glu Gln Trp Gln Gln Phe Ile Asn Trp Lys
        355                 360                 365

Gly Glu Cys Ala Arg Leu Tyr Thr Ala Glu Thr Lys Arg Gly Ser Lys
    370                 375                 380

Ser Ala Ala Val Val Arg Met Val Gly Gln Ala Arg Lys Tyr Ser Ala
385                 390                 395                 400

Phe Glu Ser Ile Tyr Phe Val Tyr Ala Met Asp Ser Arg Ser Arg Val
                405                 410                 415

Tyr Val Gln Ser Ser Thr Leu Ser Pro Gln Ser Asn Asp Leu Gly Lys
            420                 425                 430

Ala Leu Leu Arg Phe Thr Glu Gly Arg Pro Val Asn Gly Val Glu Ala
        435                 440                 445

Leu Lys Trp Phe Cys Ile Asn Gly Ala Asn Leu Trp Gly Trp Asp Lys
    450                 455                 460
```

```
Lys Thr Phe Asp Val Arg Val Ser Asn Val Leu Asp Glu Glu Phe Gln
465                 470                 475                 480

Asp Met Cys Arg Asp Ile Ala Ala Asp Pro Leu Thr Phe Thr Gln Trp
                485                 490                 495

Ala Lys Ala Asp Ala Pro Tyr Glu Phe Leu Ala Trp Cys Phe Glu Tyr
                500                 505                 510

Ala Gln Tyr Leu Asp Leu Val Asp Glu Gly Arg Ala Asp Glu Phe Arg
            515                 520                 525

Thr His Leu Pro Val His Gln Asp Gly Ser Cys Ser Gly Ile Gln His
            530                 535                 540

Tyr Ser Ala Met Leu Arg Asp Glu Val Gly Ala Lys Ala Val Asn Leu
545                 550                 555                 560

Lys Pro Ser Asp Ala Pro Gln Asp Ile Tyr Gly Ala Val Ala Gln Val
                565                 570                 575

Val Ile Lys Lys Asn Ala Leu Tyr Met Asp Ala Asp Asp Ala Thr Thr
                580                 585                 590

Phe Thr Ser Gly Ser Val Thr Leu Ser Gly Thr Glu Leu Arg Ala Met
            595                 600                 605

Ala Ser Ala Trp Asp Ser Ile Gly Ile Thr Arg Ser Leu Thr Lys Lys
610                 615                 620

Pro Val Met Thr Leu Pro Tyr Gly Ser Thr Arg Leu Thr Cys Arg Glu
625                 630                 635                 640

Ser Val Ile Asp Tyr Ile Val Asp Leu Glu Lys Glu Ala Gln Lys
                645                 650                 655

Ala Val Ala Glu Gly Arg Thr Ala Asn Lys Val His Pro Phe Glu Asp
                660                 665                 670

Asp Arg Gln Asp Tyr Leu Thr Pro Gly Ala Ala Tyr Asn Tyr Met Thr
            675                 680                 685

Ala Leu Ile Trp Pro Ser Ile Ser Glu Val Val Lys Ala Pro Ile Val
            690                 695                 700

Ala Met Lys Met Ile Arg Gln Leu Ala Arg Phe Ala Ala Lys Arg Asn
705                 710                 715                 720

Glu Gly Leu Met Tyr Thr Leu Pro Thr Gly Phe Ile Leu Glu Gln Lys
                725                 730                 735

Ile Met Ala Thr Glu Met Leu Arg Val Arg Thr Cys Leu Met Gly Asp
            740                 745                 750

Ile Lys Met Ser Leu Gln Val Glu Thr Asp Ile Val Asp Glu Ala Ala
            755                 760                 765

Met Met Gly Ala Ala Pro Asn Phe Val His Gly His Asp Ala Ser
770                 775                 780

His Leu Ile Leu Thr Val Cys Glu Leu Val Asp Lys Gly Val Thr Ser
785                 790                 795                 800

Ile Ala Val Ile His Asp Ser Phe Gly Thr His Ala Asp Asn Thr Leu
                805                 810                 815

Thr Leu Arg Val Ala Leu Lys Gly Gln Met Val Ala Met Tyr Ile Asp
            820                 825                 830

Gly Asn Ala Leu Gln Lys Leu Leu Glu Glu His Glu Glu Arg Trp Met
            835                 840                 845

Val Asp Thr Gly Ile Glu Val Pro Gln Gly Glu Phe Asp Leu Asn
850                 855                 860

Glu Ile Met Asp Ser Glu Tyr Val Phe Ala
865                 870
```

<210> SEQ ID NO 8
<211> LENGTH: 2630
<212> TYPE: DNA
<213> ORGANISM: Bacteriophage SP6

<400> SEQUENCE: 8

| | | | | | |
|---|---|---|---|---|---|
| gatgcaagat | ttacacgcta | tccagcttca | attagaagaa | gagatgttta | atggtggcat | 60 |
| tcgtcgcttc | gaagcagatc | aacaacgcca | gattgcagca | ggtagcgaga | gcgacacagc | 120 |
| atggaaccgc | cgcctgttgt | cagaacttat | tgcacctatg | gctgaaggca | ttcaggctta | 180 |
| taaagaagag | tacgaaggta | agaaaggtcg | tgcacctcgc | gcattggctt | tcttacaatg | 240 |
| tgtagaaaat | gaagttgcag | catacatcac | tatgaaagtt | gttatggata | tgctgaatac | 300 |
| ggatgctacc | cttcaggcta | ttgcaatgag | tgtagcagaa | cgcattgaag | accaagtgcg | 360 |
| cttttctaag | ctagaaggtc | acgccgctaa | atactttgag | aaggttaaga | agtcactcaa | 420 |
| ggctagccgt | actaagtcat | atcgtcacgc | tcataacgta | gctgtagttg | ctgaaaaatc | 480 |
| agttgcagaa | aaggacgcgg | actttgaccg | ttgggaggcg | tggccaaaag | aaactcaatt | 540 |
| gcagattggt | actaccttgc | ttgaaatctt | agaaggtagc | gttttctata | atggtgaacc | 600 |
| tgtatttatg | cgtgctatgc | gcacttatgg | cggaaagact | atttactact | acaaacttc | 660 |
| tgaaagtgta | ggccagtgga | ttagcgcatt | caaagagcac | gtagcgcaat | taagcccagc | 720 |
| ttatgcccct | tgcgtaatcc | ctcctcgtcc | ttggagaact | ccatttaatg | gagggttcca | 780 |
| tactgagaag | gtagctagcc | gtatccgtct | tgtaaaaggt | aaccgtgagc | atgtacgcaa | 840 |
| gttgactcaa | aagcaaatgc | caaaggttta | taaggctatc | aacgcattac | aaaatacaca | 900 |
| atggcaaatc | aacaaggatg | tattagcagt | tattgaagaa | gtaatccgct | tagaccttgg | 960 |
| ttatggtgta | ccttccttca | gccactgat | tgacaaggag | aacaagccag | ctaacccggt | 1020 |
| acctgttgaa | ttccaacacc | tgcgcggtcg | tgaactgaaa | gagatgctat | cacctgagca | 1080 |
| gtggcaacaa | ttcattaact | ggaaaggcga | atgcgcgcgc | ctatataccg | cagaaactaa | 1140 |
| gcgcggttca | aagtccgccg | ccgttgttcg | catggtagga | caggcccgta | aatatagcgc | 1200 |
| ctttgaatcc | atttacttcg | tgtacgcaat | ggatagccgc | agccgtgtct | atgtgcaatc | 1260 |
| tagcacgctc | tctccgcagt | ctaacgactt | aggtaaggca | ttactccgct | ttaccgaggg | 1320 |
| acgccctgtg | aatggcgtag | aagcgcttaa | atggttctgc | atcaatggtg | ctaacctttg | 1380 |
| gggatgggac | aagaaaactt | ttgatgtgcg | cgtgtctaac | gtattagatg | aggaattcca | 1440 |
| agatatgtgt | cgagacatcg | ccgcagaccc | tctcacattc | acccaatggg | ctaaagctga | 1500 |
| tgcaccttat | gaattcctcg | cttggtgctt | tgagtatgct | caataccttg | atttggtgga | 1560 |
| tgaaggaagg | gccgacgaat | tccgcactca | cctaccagta | catcaggacg | ggtcttgttc | 1620 |
| aggcattcag | cactatagtg | ctatgcttcg | cgacgaagta | ggggccaaag | ctgttaacct | 1680 |
| gaaaccctcc | gatgcaccgc | aggatatcta | tgggcggtg | gcgcaagtgg | ttatcaagaa | 1740 |
| gaatgcgcta | tatatggatg | cggacgatgc | aaccacgttt | acttctggta | gcgtcacgct | 1800 |
| gtccggtaca | gaactgcgag | caatggctag | cgcatgggat | agtattggta | ttacccgtag | 1860 |
| cttaaccaaa | aagcccgtga | tgaccttgcc | atatggttct | actcgcttaa | cttgccgtga | 1920 |
| atctgtgatt | gattacatcg | tagacttaga | ggaaaaagag | gcgcagaagg | cagtagcaga | 1980 |
| agggcggacg | gcaaacaagg | tacatccttt | tgaagacgat | cgtcaagatt | acttgactcc | 2040 |
| gggcgcagct | tacaactaca | tgacggcact | aatctggcct | tctatttctg | aagtagttaa | 2100 |
| ggcaccgata | gtagctatga | agatgatacg | ccagcttgca | cgctttgcag | cgaaacgtaa | 2160 |

```
tgaaggcctg atgtacaccc tgcctactgg cttcatctta gaacagaaga tcatggcaac   2220
cgagatgcta cgcgtgcgta cctgtctgat gggtgatatc aagatgtccc ttcaggttga   2280
aacggatatc gtagatgaag ccgctatgat gggagcagca gcacctaatt tcgtacacgg   2340
tcatgacgca agtcacctta tccttaccgt atgtgaattg gtagacaagg gcgtaactag   2400
tatcgctgta atccacgact cttttggtac tcatgcagac aacaccctca ctcttagagt   2460
ggcacttaaa gggcagatgg ttgcaatgta tattgatggt aatgcgcttc agaaactact   2520
ggaggagcat gaagagcgct ggatggttga tacaggtatc gaagtacctg agcaagggga   2580
gttcgacctt aacgaaatca tggattctga atacgtattt gcctaataga               2630

<210> SEQ ID NO 9
<211> LENGTH: 16
<212> TYPE: DNA
<213> ORGANISM: Bacteriophage SP6

<400> SEQUENCE: 9
taatccactg tgatat                                                    16
```